(12) United States Patent
Davis et al.

(10) Patent No.: US 11,312,978 B2
(45) Date of Patent: Apr. 26, 2022

(54) BIOCHEMICAL UPGRADING OF HIGH-PROTEIN BIOMASS AND GRAIN PRODUCTS

(71) Applicant: National Technology & Engineering Solutions of Sandia, LLC, Albuquerque, NM (US)

(72) Inventors: Ryan Wesley Davis, San Jose, CA (US); Blake Simmons, San Francisco, CA (US); Mary Bao Tran-Gyamfi, Pleasanton, CA (US); Benjamin Chiau-Pin Wu, San Ramon, CA (US)

(73) Assignee: National Technology & Engineering Solutions of Sandia, LLC, Albuquerque, NM (US)

( * ) Notice: Subject to any disclaimer, the term of this patent is extended or adjusted under 35 U.S.C. 154(b) by 0 days.

(21) Appl. No.: 16/868,670

(22) Filed: May 7, 2020

(65) Prior Publication Data
US 2020/0370071 A1 Nov. 26, 2020

Related U.S. Application Data

(62) Division of application No. 15/447,567, filed on Mar. 2, 2017, now Pat. No. 10,683,519.

(60) Provisional application No. 62/303,282, filed on Mar. 3, 2016.

(51) Int. Cl.
*C12P 7/16* (2006.01)
*C12N 9/04* (2006.01)
*C12P 13/00* (2006.01)

(52) U.S. Cl.
CPC .............. *C12P 7/16* (2013.01); *C12N 9/0006* (2013.01); *C12P 13/001* (2013.01); *C12Y 101/01001* (2013.01); *C12Y 101/01086* (2013.01)

(58) Field of Classification Search
None
See application file for complete search history.

(56) References Cited

U.S. PATENT DOCUMENTS

| | | | |
|---|---|---|---|
| 6,030,587 A | 2/2000 | Haroldsen et al. |
| 6,869,015 B2 | 3/2005 | Cummings et al. |
| 7,022,861 B1 | 4/2006 | McElhanon et al. |
| 7,253,008 B2 | 8/2007 | Rucker et al. |
| 7,264,962 B1 | 9/2007 | Simmons et al. |
| 7,351,380 B2 | 4/2008 | Simmons et al. |
| 7,351,837 B1 | 4/2008 | McElhanon et al. |
| 7,358,221 B1 | 4/2008 | Jamison et al. |
| 7,378,533 B1 | 5/2008 | McElhanon et al. |
| 7,390,377 B1 | 6/2008 | Wallow et al. |
| 7,419,574 B2 | 9/2008 | Cummings et al. |
| 7,556,945 B1 | 7/2009 | Simmons et al. |
| 7,559,961 B2 | 7/2009 | Jimeson et al. |
| 7,560,028 B1 | 7/2009 | Simmons et al. |
| 7,595,349 B1 | 9/2009 | McElhanon et al. |
| 7,608,461 B1 | 10/2009 | Simmons et al. |
| 7,622,596 B1 | 11/2009 | McElhanon et al. |
| 7,666,289 B2 | 2/2010 | Simmons et al. |
| 7,678,256 B2 | 3/2010 | Davalos et al. |
| 7,811,439 B1 | 10/2010 | Simmons et al. |
| 7,985,868 B1 | 7/2011 | Bauer et al. |
| 8,047,978 B1 | 11/2011 | Haroldsen et al. |
| 8,257,568 B1 | 9/2012 | Simmons et al. |
| 8,257,571 B1 | 9/2012 | Cummings et al. |
| 8,481,974 B1 | 7/2013 | Davis et al. |
| 8,808,588 B1 | 8/2014 | Simmons et al. |
| 9,157,130 B2 | 10/2015 | Brennan et al. |
| 9,322,042 B2 | 4/2016 | Sapra et al. |
| 9,376,728 B2 | 6/2016 | Zhang et al. |
| 9,624,482 B2 | 4/2017 | Simmons et al. |
| 9,725,749 B2 | 8/2017 | Chen et al. |
| 9,765,044 B2 | 9/2017 | Socha et al. |
| 9,803,182 B2 | 10/2017 | Gladden et al. |
| 9,862,982 B2 | 1/2018 | Zhang et al. |
| 10,077,454 B1 | 9/2018 | Davis et al. |
| 10,112,916 B2 | 10/2018 | Sathitsuksanoh et al. |
| 10,155,735 B2 | 12/2018 | Socha et al. |
| 10,208,076 B2 | 2/2019 | Singh et al. |
| 10,233,292 B2 | 3/2019 | Singh et al. |
| 2010/0143997 A1 | 6/2010 | Buelter et al. |
| 2013/0288325 A1 | 10/2013 | Liao et al. |

FOREIGN PATENT DOCUMENTS

WO  2012/173660 A2  12/2012

OTHER PUBLICATIONS

U.S. Appl. No. 14/750,993, filed Jun. 25, 2015, Hewson et al.
U.S. Appl. No. 15/066,651, filed Mar. 10, 2016, Wu et al.
Alterthum F et al., "Efficient ethanol production from glucose, lactose, and xylose by recombinant *Escherichia coli*," *Appl. Environ. Microbiol.* 1989;55:1943-8.
Atsumi S et al., "Engineering the isobutanol biosynthetic pathway in *Escherichia coli* by comparison of three aldehyde reductase/alcohol dehydrogenase genes," *Appl. Microbiol. Biotechnol.* 2010;85:651-7.
Atsumi S et al., "Non-fermentative pathways for synthesis of branched-chain higher alcohols as biofuels," *Nature* 2008;451:86-9.
Bastian S et al., "Engineered ketol-acid reductoisomerase and alcohol dehydrogenase enable anaerobic 2-methylpropan-1-ol production at theoretical yield in *Escherichia coli*," *Metab. Eng.* 2011;13(3):345-52.
Bizukojc M et al., "Metabolic modelling of syntrophic-like growth of a 1,3-propanediol producer, *Clostridium butyricum*, and a methanogenic archeon, *Methanosarcina mazei*, under anaerobic conditions," *Bioprocess Biosyst. Eng.* 2010;33:507-23.

(Continued)

*Primary Examiner* — Paul J Holland
(74) *Attorney, Agent, or Firm* — Madelynne J. Farber; Samantha Updegraff

(57) ABSTRACT

The present invention relates to methods of upgrading biomass to provide useful chemical intermediates, fuels, amino acids, nutrients, etc. In particular examples, the biomass is a by-product of ethanol production and is mainly used as high-protein feed. Described herein are methods for upgrading such biomass, such as by implementing pretreatment conditions and by employing fermentation conditions including modified organisms.

10 Claims, 18 Drawing Sheets

Specification includes a Sequence Listing.

(56) References Cited

OTHER PUBLICATIONS

Bothast RJ et al., "Biotechnological processes for conversion of corn into ethanol," *Appl. Microbiol. Biotechnol.* 2005;67:19-25.

Brinkkötter A et al., "Pathways for the utilization of N-acetyl-galactosamine and galactosamine in *Escherichia coli*," *Mol. Microbiol.* 2000;37:125-35.

Brinkmann-Chen S et al., "General approach to reversing ketol-acid reductoisomerase cofactor dependence from NADPH to NADH," *Proc. Acad. Nat'l Sci. USA* 2013;110:10946-51.

Chubukov V et al., "Synthetic and systems biology for microbial production of commodity chemicals," *npj Syst. Biol. Appl.* 2016;2:16009 (11 pp.).

Datsenko KA et al., "One-step inactivation of chromosomal genes in *Escherichia coli* K-12 using PCR products," *Proc. Nat'l Acad. Sci. USA* 2000;97:6640-5.

De La Plaza M et al., "Biochemical and molecular characterization of α-ketoisovalerate decarboxylase, an enzyme involved in the formation of aldehydes from amino acids by *Lactococcus lactis*," *FEMS Microbiol. Lett.* 2004;238:367-74.

Dueber JE et al., "Synthetic protein scaffolds provide modular control over metabolic flux," *Nat. Biotechnol.* 2009;27:753-9.

Friedman M, "Applications of the ninhydrin reaction for analysis of amino acids, peptides, and proteins to agricultural and biomedical sciences," *J. Agric. Food Chem.* 2004;52:385-406.

Garcia-Moscoso JL et al., "Flash hydrolysis of microalgae (*Scenedesmus* sp.) for protein extraction and production of biofuels intermediates," *J. Supercrit. Fluids* 2013;82:183-90.

Garcia-Moscoso JL et al., "Kinetics of peptides and arginine production from microalgae (*Scenedesmus* sp.) by flash hydrolysis," *Ind. Eng. Chem. Res.* 2015;54(7):2048-58.

Goers L et al., "Co-culture systems and technologies: taking synthetic biology to the next level," *J. R. Soc. Interface* 2014;11:20140065 (13 pp.).

Hernández D et al., "Biofuels from microalgae: lipid extraction and methane production from the residual biomass in a biorefinery approach," *Bioresour. Technol.* 2014;170:370-8.

Huang R et al., "PCR-based multiple species cell counting for in vitro mixed culture," *PLoS One* 2015;10:e0126628 (13 pp.).

Huo YX et al., "Conversion of proteins into biofuels by engineering nitrogen flux," *Nat. Biotechnol.* 2011;29:346-51.

Keasling D, "Sustainable production of advanced biofuels," *241st ACS National Meeting & Exposition*, held on Mar. 27-31, 2011 in Anaheim, CA, Abstract 202 (1 p.).

Kim JH et al., "Simultaneous consumption of pentose and hexose sugars: an optimal microbial phenotype for efficient fermentation of lignocellulosic biomass," *Appl. Microbiol. Biotechnol.* 2010;88:1077-85.

Kim Y et al., "Enzyme hydrolysis and ethanol fermentation of liquid hot water and AFEX pretreated distillers' grains at high-solids loadings," *Bioresour. Technol.* 2008;99:5206-15.

Kurokawa M et al., "Correlation between genome reduction and bacterial growth," *DNA Res.* 2016;23:517-25.

Kyrpides NC et al., "Genomic encyclopedia of bacteria and archaea: sequencing a myriad of type strains," *PLoS Biol.* 2014;12:e1001920 (7 pp.).

Lan EI et al., "Microbial synthesis of n-butanol, isobutanol, and other higher alcohols from diverse resources," *Bioresour. Technol.* 2013;135:339-49.

Lau MW et al., "Comparing the fermentation performance of *Escherichia coli* KO11, *Saccharomyces cerevisiae* 424(LNH-ST) and *Zymomonas mobilis* AX101 for cellulosic ethanol production," Biotechnology for Biofuels (2010) 3:1-10.

Li K et al., "An overview of algae bioethanol production," *Int. J. Energy Res.* 2014;38(8):965-77.

Liao JC et al., "Fuelling the future: microbial engineering for the production of sustainable biofuels," *Nat. Rev. Microbiol.* 2016;14:288-304.

Liu F et al., "Bioconversion of distillers' grain hydrolysates to advanced biofuels by an *Escherichia coli* co-culture," *Microb. Cell Fact.* 2017;16:192 (14 pp.).

Liu F et al., "Engineering microbial consortia for bioconversion of multisubstrate biomass streams to biofuels," Chapter 7 (pp. 101-120) in *Biofuels: Challenges and opportunities* (M. Al Qubeissi, ed.), IntechOpen (London, United Kingdom), 2019.

Liu F et al., "Functional assembly of a multi-enzyme methanol oxidation cascade on a surface-displayed trifunctional scaffold for enhanced NADH production," *Chem. Commun.* 2013;49:3766-8.

Liu KS, "Chemical composition of distillers grains, a review," *J. Agric. Food Chem.* 2011;59:1508-26.

López Barreiro D et al., "Assessing microalgae biorefinery routes for the production of biofuels via hydrothermal liquefaction," *Bioresour. Technol.* 2014;174:256-65.

Luque R, "Algal biofuels: the eternal promise?," *Energy Environ. Sci.* 2010;3:254-7.

Ma F et al., "Biodiesel production: a review," *Bioresourc. Technol.* 1999;70:1-15.

Martinez-Amezcua C., et al., Nutritional Characteristics of Corn Distillers Dried Grains with Solubles as Affected by the Amounts of Grains Versus Solubles and Different Processing Techniques, 2007, 86:2624-2630.

Masuko T et al., "Carbohydrate analysis by a phenol-sulfuric acid method in microplate format," *Anal. Biochem.* 2005;339:69-72.

Melis A et al., "Hydrogen production: green algae as a source of energy," *Plant Physiol.* 2001;127(3):740-8.

Naik SN et al., "Production of first and second generation biofuels: a comprehensive review," *Renew. Sustain. Energy Rev.* 2010;14:578-97.

Noureddini H et al., "Dilute-acid pretreatment of distillers' grains and corn fiber," *Bioresour. Technol.* 2010;101:1060-7.

NP-417484. NADPH Dependent Aldehyde Reductase YqhD, 2018, pp. 1-3.

Palmqvist E et al., "Fermentation of lignocellulosic hydrolysates. II: inhibitors and mechanisms of inhibition," *Bioresour. Technol.* 2000;74:25-33.

Park M et al., "Positional assembly of enzymes on bacterial outer membrane vesicles for cascade reactions," *PLoS One* 2014;9:e97103 (6 pp.).

Peralta-Yahya PP et al., "Microbial engineering for the production of advanced biofuels," *Nature* 2012;488(7411):320-8.

Qu Y et al., "Use of a coculture to enable current production by *Geobacter sulfurreducens*," *Appl. Environ. Microbiol.* 2012;78:3484-7.

Raheem A et al., "Thermochemical conversion of microalgal biomass for biofuel production," *Renew. Sustain. Energy Rev.* 2015;49:990-9.

Razeghifard R, "Algal biofuels," *Photosynth. Res.* 2013;117(1-3):207-19.

Ringer M et al., "Large-scale pyrolysis oil production: a technology assessment and economic analysis," *National Renewable Energy Laboratory Technical Report NREL/TP-510-37779*, Nov. 2006, 93 pp.

Sarathy SM et al., "Alcohol combustion chemistry," *Prog. Energy Combust. Sci.* 2014;44:40-102.

Schneider RCS et al., "Potential production of biofuel from microalgae biomass produced in wastewater," in *Biodiesel—Feedstocks, Production and Applications*, Prof. Zhen Fang (ed.), InTech, 2012, 22 pp.

Scott SA et al., "Biodiesel from algae: challenges and prospects," *Curr. Opin. Biotechnol.* 2010;21(3):277-86.

Sharma KK et al., "High lipid induction in microalgae for biodiesel production," *Energies* 2012;5(5):1532-53.

Shi A et al., "Activating transhydrogenase and NAD kinase in combination for improving isobutanol production," *Metab. Eng.* 2013;16:1-10.

Singh J et al., "Commercialization potential of microalgae for biofuels production," *Renew. Sustain. Energy Rev.* 2010;14(9):2596-610.

Smith KM et al., "An evolutionary strategy for isobutanol production strain development in *Escherichia coli*," *Metab. Eng.* 2011;13(6):674-81.

(56) References Cited

OTHER PUBLICATIONS

Studier FW et al., "Understanding the differences between genome sequences of *Escherichia coli* B strains REL606 and BL21(DE3) and comparison of the *E. coli* B and K-12 genomes," *J. Mol. Biol.* 2009;394:653-80.

Sulzenbacher G et al., "Crystal structure of *E. coli* alcohol dehydrogenase YqhD: evidence of a covalently modified NADP coenzyme," *J. Mol. Biol.* 2004;342(2):489-502.

Taherzadeh MJ et al., Acid-Based Hydrolysis Processes for Ethanol from Lignocelullosic Materials: A Review, Bioresources 2007 2(3):472-499.

Tran NH et al., "Catalytic upgrading of biorefinery oil from microalgae," *Fuel* 2010;89:265-74.

Um BH et al., "Effect of sulfuric and phosphoric acid pretreatments on enzymatic hydrolysis of corn stover," *Appl. Biochem. Biotechnol.* 2003;105-108:115-25.

Wildschut J et al., "Catalyst studies on the hydrotreatment of fast pyrolysis oil," *Appl. Catalysis* B 2010;99:298-306.

Wu W, "Fuel ethanol production using novel carbon sources and fermentation medium optimization with response surface methodology," *Int. J. Agric. Biol. Eng.* 2013;6:42-53.

Wu W et al., "Cofactor engineering of ketol-acid reductoisomerase (IlvC) and alcohol dehydrogenase (YqhD) improves the fusel alcohol yield in algal protein anaerobic fermentation," *Algal Res.* 2016;19:162-7.

Wu W et al., "One-pot bioconversion of algae biomass into terpenes for advanced biofuels and bioproducts," *Algal Res.* 2016;17:316-20.

Wu W et al., "Site-saturation mutagenesis of formate dehydrogenase from *Candida bodinii* creating effective NADP+-dependent FDH enzymes," *J. Molec. Catal.* B 2009;61(3-4):157-61.

Zhang H et al., "Engineering *Escherichia coli* coculture systems for the production of biochemical products," *Proc. Nat'l Acad. Sci. USA* 2015;112:8266-71.

Zhou YJ et al., "Production of fatty acid-derived oleochemicals and biofuels by synthetic yeast cell factories," *Nat. Commun.* 2016;7:11709 (9 pp.).

Zhu Y et al., "Dilute-acid pretreatment of corn stover using a high-solids percolation reactor," *Appl. Biochem. Biotechnol.* 2004;117:103-14.

Redox mutants screening

*E. coli* alcohol dehydrogenase YqhD (SEQ ID NO:1)

```
         10         20         30         40         50
MNNFNLHTPT RILFGKGAIA GLREQIPHDA RVLITYGGGS VKKTGVLDQV
         60         70         80         90        100
LDALKGMDVL EFGGIEPNPA YETLMNAVKL VREQKVTFLL AVGGGSVLDG
        110        120        130        140        150
TKFIAAAANY PENIDPWHIL QTGGKEIKSA IPMGCVLTLP ATGSESNAGA
        160        170        180        190        200
VISRKTTGDK QAFHSAHVQP VFAVLDPVYT YTLPPRQVAN GVVDAFVHTV
        210        220        230        240        250
EQYVTKPVDA KIQDRFAEGI LLTLIEDGPK ALKEPENYDV RANVMWAATQ
        260        270        280        290        300
ALNGLIGAGV PQDWATHMLG HELTAMHGLD HAQTLAIVLP ALWNEKRDTK
        310        320        330        340        350
RAKLLQYAER VWNITEGSDD ERIDAAIAAT RNFFEQLGVP THLSDYGLDG
        360        370        380
SSIPALLKKL EEHGMTQLGE NHDITLDVSR RIYEAAR
```

FIG. 10C

YqhD mutant 1 (SEQ ID NO:2)

```
         10         20         30         40         50
MNNFNLHTPT RILFGKGAIA GLREQIPHDA RVLITYGGXS VKKTGVLDQV
         60         70         80         90        100
LDALKGMDVL EFGGIEPNPA YETLMNAVKL VREQKVTFLL AVGGGSVLDG
        110        120        130        140        150
TKFIAAAANY PENIDPWHIL QTGGKEIKSA IPMGCVLTLP ATGSESNAGA
        160        170        180        190        200
VISRKTTGDK QAFHSAHVQP VFAVLDPVYT YTLPPRQVAN GVVDAFVHTV
        210        220        230        240        250
EQYVTKPVDA KIQDRFAEGI LLTLIEDGPK ALKEPENYDV RANVMWAATQ
        260        270        280        290        300
ALNGLIGAGV PQDWATHMLG HELTAMHGLD HAQTLAIVLP ALWNEKRDTK
        310        320        330        340        350
RAKLLQYAER VWNITEGSDD ERIDAAIAAT RNFFEQLGVP THLSDYGLDG
        360        370        380
SSIPALLKKL EEHGMTQLGE NHDITLDVSR RIYEAAR
```

FIG. 10D

YqhD mutant 2 (SEQ ID NO:3)

```
        10         20         30         40         50
MNNFNLHTPT RILFGKGAIA GLREQIPHDA RVLITYGGGX VKKTGVLDQV
        60         70         80         90        100
LDALKGMDVL EFGGIEPNPA YETLMNAVKL VREQKVTFLL AVGGGSVLDG
       110        120        130        140        150
TKFIAAAANY PENIDPWHIL QTGGKEIKSA IPMGCVLTLP ATGSESNAGA
       160        170        180        190        200
VISRKTTGDK QAFHSAHVQP VFAVLDPVYT YTLPPRQVAN GVVDAFVHTV
       210        220        230        240        250
EQYVTKPVDA KIQDRFAEGI LLTLIEDGPK ALKEPENYDV RANVMWAATQ
       260        270        280        290        300
ALNGLIGAGV PQDWATHMLG HELTAMHGLD HAQTLAIVLP ALWNEKRDTK
       310        320        330        340        350
RAKLLQYAER VWNITEGSDD ERIDAAIAAT RNFFEQLGVP THLSDYGLDG
       360        370        380
SSIPALLKKL EEHGMTQLGE NHDITLDVSR RIYEAAR
```

FIG. 10E

YqhD mutant 3 (SEQ ID NO:4)

```
        10         20         30         40         50
MNNFNLHTPT RILFGKGAIA GLREQIPHDA RVLITYGGXX VKKTGVLDQV
        60         70         80         90        100
LDALKGMDVL EFGGIEPNPA YETLMNAVKL VREQKVTFLL AVGGGSVLDG
       110        120        130        140        150
TKFIAAAANY PENIDPWHIL QTGGKEIKSA IPMGCVLTLP ATGSESNAGA
       160        170        180        190        200
VISRKTTGDK QAFHSAHVQP VFAVLDPVYT YTLPPRQVAN GVVDAFVHTV
       210        220        230        240        250
EQYVTKPVDA KIQDRFAEGI LLTLIEDGPK ALKEPENYDV RANVMWAATQ
       260        270        280        290        300
ALNGLIGAGV PQDWATHMLG HELTAMHGLD HAQTLAIVLP ALWNEKRDTK
       310        320        330        340        350
RAKLLQYAER VWNITEGSDD ERIDAAIAAT RNFFEQLGVP THLSDYGLDG
       360        370        380
SSIPALLKKL EEHGMTQLGE NHDITLDVSR RIYEAAR
```

FIG. 10F

YqhD mutant 4 (SEQ ID NO:5)

```
        10         20         30         40         50
MNNFNLHTPT RILFGKGAIA GLREQIPHDA RVLITYXXXX VKKTGVLDQV
        60         70         80         90        100
LDALKGMDVL EFGGIEPNPA YETLMNAVKL VREQKVTFLL AVGGGSVLDG
       110        120        130        140        150
TKFIAAAANY PENIDPWHIL QTGGKEIKSA IPMGCVLTLP ATGSESNAGA
       160        170        180        190        200
VISRKTTGDK QAFHSAHVQP VFAVLDPVYT YTLPPRQVAN GVVDAFVHTV
       210        220        230        240        250
EQYVTKPVDA KIQDRFAEGI LLTLIEDGPK ALKEPENYDV RANVMWAATQ
       260        270        280        290        300
ALNGLIGAGV PQDWATHMLG HELTAMHGLD HAQTLAIVLP ALWNEKRDTK
       310        320        330        340        350
RAKLLQYAER VWNITEGSDD ERIDAAIAAT RNFFEQLGVP THLSDYGLDG
       360        370        380
SSIPALLKKL EEHGMTQLGE NHDITLDVSR RIYEAAR
```

FIG. 10G

*E. coli* ketol-acid reductoisomerase IlvC (SEQ ID NO:6)

```
         10         20         30         40         50
MANYFNTLNL RQQLAQLGKC RFMGRDEFAD GASYLQGKKV VIVGCGAQGL
         60         70         80         90        100
NQGLNMRDSG LDISYALRKE AIAEKRASWR KATENGFKVG TYEELIPQAD
        110        120        130        140        150
LVINLTPDKQ HSDVVRTVQP LMKDGAALGY SHGFNIVEVG EQIRKDITVV
        160        170        180        190        200
MVAPKCPGTE VREEYKRGFG VPTLIAVHPE NDPKGEGMAI AKAWAAATGG
        210        220        230        240        250
HRAGVLESSF VAEVKSDLMG EQTILCGMLQ AGSLLCFDKL VEEGTDPAYA
        260        270        280        290        300
EKLIQFGWET ITEALKQGGI TLMMDRLSNP AKLRAYALSE QLKEIMAPLF
        310        320        330        340        350
QKHMDDIISG EFSSGMMADW ANDDKKLLTW REETGKTAFE TAPQYEGKIG
        360        370        380        390        400
EQEYFDKGVL MIAMVKAGVE LAFETMVDSG IIEESAYYES LHELPLIANT
        410        420        430        440        450
IARKRLYEMN VVISDTAEYG NYLFSYACVP LLKPFMAELQ PGDLGKAIPE
        460        470        480        490
GAVDNGQLRD VNEAIRSHAI EQVGKKLRGY MTDMKRIAVA G
```

FIG. 11A

IlvC mutant (SEQ ID NO:7)

```
         10         20         30         40         50
MANYFNTLNL RQQLAQLGKC RFMGRDEFAD GASYLQGKKV VIVGCGAQGL
         60         70         80         90        100
NQGLNMRDSG LDISYALRKE XIAEKXAXWR KATENGFKVG TYEELIPQAD
        110        120        130        140        150
LVINLTPDKX HSDVVRTVQP LMKDGAALGY SHGFNIVEVG EQIRKXITVV
        160        170        180        190        200
MVAPKCPGTE VREEYKRGFG VPTLIAVHPE NDPKXEGMAI AKAWAAATGG
        210        220        230        240        250
HRAGVLESSF VAEVKSDLMG EQTILCGMLQ AGSLLCFDKL VEEGTDPAYA
        260        270        280        290        300
EKLIQFGWET ITEALKQGGI TLMMDRLSNP AKLRAYALSE QLKEIMAPLF
        310        320        330        340        350
QKHMDDIISG EFSSGMMADW ANDDKKLLTW REETGKTAFE TAPQYEGKIG
        360        370        380        390        400
EQEYFDKGVL MIAMVKAGVE LAFETMVDSG IIEESAYYES LHELPLIANT
        410        420        430        440        450
IARKRLYEMN VVISDTAEYG NYLFSYACVP LLXPFMAELQ PGDLGKAIPE
        460        470        480        490
GAVDNGQLRD VNEAIRSHAI EQVGKKLRGY MTDMKRIAVA G
```

FIG. 11B

SEQUENCE LISTING

<160> NUMBER OF SEQ ID NOS: 43

<210> SEQ ID NO 1
<211> LENGTH: 387
<212> TYPE: PRT

<213> ORGANISM: Escherichia coli

<400> SEQUENCE: 1

```
Met Asn Asn Phe Asn Leu His Thr Pro Thr Arg Ile Leu Phe Gly Lys
 1               5                  10                  15

Gly Ala Ile Ala Gly Leu Arg Glu Gln Ile Pro His Asp Ala Arg Val
                20                  25                  30

Leu Ile Thr Tyr Gly Gly Gly Ser Val Lys Lys Thr Gly Val Leu Asp
            35                  40                  45

Gln Val Leu Asp Ala Leu Lys Gly Met Asp Val Leu Glu Phe Gly Gly
        50                  55                  60

Ile Glu Pro Asn Pro Ala Tyr Glu Thr Leu Met Asn Ala Val Lys Leu
 65                  70                  75                  80

Val Arg Glu Gln Lys Val Thr Phe Leu Leu Ala Val Gly Gly Gly Ser
                85                  90                  95

Val Leu Asp Gly Thr Lys Phe Ile Ala Ala Ala Asn Tyr Pro Glu
                100                 105                 110

Asn Ile Asp Pro Trp His Ile Leu Gln Thr Gly Gly Lys Glu Ile Lys
            115                 120                 125

Ser Ala Ile Pro Met Gly Cys Val Leu Thr Leu Pro Ala Thr Gly Ser
130                 135                 140

Glu Ser Asn Ala Gly Ala Val Ile Ser Arg Lys Thr Thr Gly Asp Lys
145                 150                 155                 160

Gln Ala Phe His Ser Ala His Val Gln Pro Val Phe Ala Val Leu Asp
                165                 170                 175

Pro Val Tyr Thr Tyr Thr Leu Pro Pro Arg Gln Val Ala Asn Gly Val
            180                 185                 190

Val Asp Ala Phe Val His Thr Val Glu Gln Tyr Val Thr Lys Pro Val
        195                 200                 205

Asp Ala Lys Ile Gln Asp Arg Phe Ala Glu Gly Ile Leu Leu Thr Leu
    210                 215                 220

Ile Glu Asp Gly Pro Lys Ala Leu Lys Glu Pro Glu Asn Tyr Asp Val
225                 230                 235                 240

Arg Ala Asn Val Met Trp Ala Ala Thr Gln Ala Leu Asn Gly Leu Ile
                245                 250                 255

Gly Ala Gly Val Pro Gln Asp Trp Ala Thr His Met Leu Gly His Glu
            260                 265                 270

Leu Thr Ala Met His Gly Leu Asp His Ala Gln Thr Leu Ala Ile Val
        275                 280                 285

Leu Pro Ala Leu Trp Asn Glu Lys Arg Asp Thr Lys Arg Ala Lys Leu
    290                 295                 300

Leu Gln Tyr Ala Glu Arg Val Trp Asn Ile Thr Glu Gly Ser Asp Asp
305                 310                 315                 320

Glu Arg Ile Asp Ala Ala Ile Ala Ala Thr Arg Asn Phe Phe Glu Gln
                325                 330                 335

Leu Gly Val Pro Thr His Leu Ser Asp Tyr Gly Leu Asp Gly Ser Ser
            340                 345                 350

Ile Pro Ala Leu Leu Lys Lys Leu Glu Glu His Gly Met Thr Gln Leu
        355                 360                 365

Gly Glu Asn His Asp Ile Thr Leu Asp Val Ser Arg Arg Ile Tyr Glu
    370                 375                 380

Ala Ala Arg
385
```

```
<210> SEQ ID NO 2
<211> LENGTH: 387
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (39)..(39)
<223> OTHER INFORMATION: Xaa at position 39 can be any useful amino acid
      substitution (e.g., Ile, Tyr, Val, Leu, Phe, or any other
      conservative amino acid substitution described in the
      specification)

<400> SEQUENCE: 2
```

Met Asn Asn Phe Asn Leu His Thr Pro Thr Arg Ile Leu Phe Gly Lys
1               5                   10                  15

Gly Ala Ile Ala Gly Leu Arg Glu Gln Ile Pro His Asp Ala Arg Val
            20                  25                  30

Leu Ile Thr Tyr Gly Gly Xaa Ser Val Lys Lys Thr Gly Val Leu Asp
        35                  40                  45

Gln Val Leu Asp Ala Leu Lys Gly Met Asp Val Leu Glu Phe Gly Gly
    50                  55                  60

Ile Glu Pro Asn Pro Ala Tyr Glu Thr Leu Met Asn Ala Val Lys Leu
65                  70                  75                  80

Val Arg Glu Gln Lys Val Thr Phe Leu Leu Ala Val Gly Gly Gly Ser
                85                  90                  95

Val Leu Asp Gly Thr Lys Phe Ile Ala Ala Ala Asn Tyr Pro Glu
            100                 105                 110

Asn Ile Asp Pro Trp His Ile Leu Gln Thr Gly Gly Lys Glu Ile Lys
            115                 120                 125

Ser Ala Ile Pro Met Gly Cys Val Leu Thr Leu Pro Ala Thr Gly Ser
    130                 135                 140

Glu Ser Asn Ala Gly Ala Val Ile Ser Arg Lys Thr Thr Gly Asp Lys
145                 150                 155                 160

Gln Ala Phe His Ser Ala His Val Gln Pro Val Phe Ala Val Leu Asp
                165                 170                 175

Pro Val Tyr Thr Tyr Thr Leu Pro Pro Arg Gln Val Ala Asn Gly Val
            180                 185                 190

Val Asp Ala Phe Val His Thr Val Glu Gln Tyr Val Thr Lys Pro Val
        195                 200                 205

Asp Ala Lys Ile Gln Asp Arg Phe Ala Glu Gly Ile Leu Leu Thr Leu
    210                 215                 220

Ile Glu Asp Gly Pro Lys Ala Leu Lys Glu Pro Glu Asn Tyr Asp Val
225                 230                 235                 240

Arg Ala Asn Val Met Trp Ala Ala Thr Gln Ala Leu Asn Gly Leu Ile
                245                 250                 255

Gly Ala Gly Val Pro Gln Asp Trp Ala Thr His Met Leu Gly His Glu
            260                 265                 270

Leu Thr Ala Met His Gly Leu Asp His Ala Gln Thr Leu Ala Ile Val
        275                 280                 285

Leu Pro Ala Leu Trp Asn Glu Lys Arg Asp Thr Lys Arg Ala Lys Leu
    290                 295                 300

Leu Gln Tyr Ala Glu Arg Val Trp Asn Ile Thr Glu Gly Ser Asp Asp
305                 310                 315                 320

Glu Arg Ile Asp Ala Ala Ile Ala Ala Thr Arg Asn Phe Phe Glu Gln
                325                 330                 335

```
Leu Gly Val Pro Thr His Leu Ser Asp Tyr Gly Leu Asp Gly Ser Ser
            340                 345                 350

Ile Pro Ala Leu Leu Lys Lys Leu Glu Glu His Gly Met Thr Gln Leu
            355                 360                 365

Gly Glu Asn His Asp Ile Thr Leu Asp Val Ser Arg Arg Ile Tyr Glu
    370                 375                 380

Ala Ala Arg
385

<210> SEQ ID NO 3
<211> LENGTH: 387
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (40)..(40)
<223> OTHER INFORMATION: Xaa at position 40 can be any useful amino acid
      substitution (e.g., Pro, Arg, His, Lys, Trp, or any other
      conservative amino acid substitution described in the
      specification)

<400> SEQUENCE: 3

Met Asn Asn Phe Asn Leu His Thr Pro Thr Arg Ile Leu Phe Gly Lys
1               5                   10                  15

Gly Ala Ile Ala Gly Leu Arg Glu Gln Ile Pro His Asp Ala Arg Val
            20                  25                  30

Leu Ile Thr Tyr Gly Gly Gly Xaa Val Lys Lys Thr Gly Val Leu Asp
        35                  40                  45

Gln Val Leu Asp Ala Leu Lys Gly Met Asp Val Leu Glu Phe Gly Gly
    50                  55                  60

Ile Glu Pro Asn Pro Ala Tyr Glu Thr Leu Met Asn Ala Val Lys Leu
65                  70                  75                  80

Val Arg Glu Gln Lys Val Thr Phe Leu Leu Ala Val Gly Gly Gly Ser
                85                  90                  95

Val Leu Asp Gly Thr Lys Phe Ile Ala Ala Ala Asn Tyr Pro Glu
            100                 105                 110

Asn Ile Asp Pro Trp His Ile Leu Gln Thr Gly Gly Lys Glu Ile Lys
        115                 120                 125

Ser Ala Ile Pro Met Gly Cys Val Leu Thr Leu Pro Ala Thr Gly Ser
    130                 135                 140

Glu Ser Asn Ala Gly Ala Val Ile Ser Arg Lys Thr Thr Gly Asp Lys
145                 150                 155                 160

Gln Ala Phe His Ser Ala His Val Gln Pro Val Phe Ala Val Leu Asp
                165                 170                 175

Pro Val Tyr Thr Tyr Thr Leu Pro Pro Arg Gln Val Ala Asn Gly Val
            180                 185                 190

Val Asp Ala Phe Val His Thr Val Glu Gln Tyr Val Thr Lys Pro Val
        195                 200                 205

Asp Ala Lys Ile Gln Asp Arg Phe Ala Glu Gly Ile Leu Leu Thr Leu
    210                 215                 220

Ile Glu Asp Gly Pro Lys Ala Leu Lys Glu Pro Glu Asn Tyr Asp Val
225                 230                 235                 240

Arg Ala Asn Val Met Trp Ala Ala Thr Gln Ala Leu Asn Gly Leu Ile
                245                 250                 255

Gly Ala Gly Val Pro Gln Asp Trp Ala Thr His Met Leu Gly His Glu
```

-continued

```
                260                 265                 270
Leu Thr Ala Met His Gly Leu Asp His Ala Gln Thr Leu Ala Ile Val
        275                 280                 285
Leu Pro Ala Leu Trp Asn Glu Lys Arg Asp Thr Lys Arg Ala Lys Leu
    290                 295                 300
Leu Gln Tyr Ala Glu Arg Val Trp Asn Ile Thr Glu Gly Ser Asp Asp
305                 310                 315                 320
Glu Arg Ile Asp Ala Ala Ile Ala Ala Thr Arg Asn Phe Phe Glu Gln
                325                 330                 335
Leu Gly Val Pro Thr His Leu Ser Asp Tyr Gly Leu Asp Gly Ser Ser
            340                 345                 350
Ile Pro Ala Leu Leu Lys Lys Leu Glu Glu His Gly Met Thr Gln Leu
        355                 360                 365
Gly Glu Asn His Asp Ile Thr Leu Asp Val Ser Arg Arg Ile Tyr Glu
    370                 375                 380
Ala Ala Arg
385

<210> SEQ ID NO 4
<211> LENGTH: 387
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (39)..(40)
<223> OTHER INFORMATION: Xaa at position 39 and 40 can be any useful
      amino acid substitution (e.g., Ile at position 39 and Arg at
      position 40; Tyr at position 39 and His at position 40; as well as
      any other conservative amino acid substitution described in the
      specification)

<400> SEQUENCE: 4

Met Asn Asn Phe Asn Leu His Thr Pro Thr Arg Ile Leu Phe Gly Lys
1               5                   10                  15
Gly Ala Ile Ala Gly Leu Arg Glu Gln Ile Pro His Asp Ala Arg Val
            20                  25                  30
Leu Ile Thr Tyr Gly Gly Xaa Xaa Val Lys Lys Thr Gly Val Leu Asp
        35                  40                  45
Gln Val Leu Asp Ala Leu Lys Gly Met Asp Val Leu Glu Phe Gly Gly
    50                  55                  60
Ile Glu Pro Asn Pro Ala Tyr Glu Thr Leu Met Asn Ala Val Lys Leu
65                  70                  75                  80
Val Arg Glu Gln Lys Val Thr Phe Leu Leu Ala Val Gly Gly Gly Ser
                85                  90                  95
Val Leu Asp Gly Thr Lys Phe Ile Ala Ala Ala Asn Tyr Pro Glu
            100                 105                 110
Asn Ile Asp Pro Trp His Ile Leu Gln Thr Gly Gly Lys Glu Ile Lys
        115                 120                 125
Ser Ala Ile Pro Met Gly Cys Val Leu Thr Leu Pro Ala Thr Gly Ser
    130                 135                 140
Glu Ser Asn Ala Gly Ala Val Ile Ser Arg Lys Thr Thr Gly Asp Lys
145                 150                 155                 160
Gln Ala Phe His Ser Ala His Val Gln Pro Val Phe Ala Val Leu Asp
                165                 170                 175
Pro Val Tyr Thr Tyr Thr Leu Pro Pro Arg Gln Val Ala Asn Gly Val
            180                 185                 190
```

```
Val Asp Ala Phe Val His Thr Val Glu Gln Tyr Val Thr Lys Pro Val
        195                 200                 205

Asp Ala Lys Ile Gln Asp Arg Phe Ala Glu Gly Ile Leu Leu Thr Leu
    210                 215                 220

Ile Glu Asp Gly Pro Lys Ala Leu Lys Glu Pro Glu Asn Tyr Asp Val
225                 230                 235                 240

Arg Ala Asn Val Met Trp Ala Ala Thr Gln Ala Leu Asn Gly Leu Ile
                245                 250                 255

Gly Ala Gly Val Pro Gln Asp Trp Ala Thr His Met Leu Gly His Glu
                260                 265                 270

Leu Thr Ala Met His Gly Leu Asp His Ala Gln Thr Leu Ala Ile Val
                275                 280                 285

Leu Pro Ala Leu Trp Asn Glu Lys Arg Asp Thr Lys Arg Ala Lys Leu
                290                 295                 300

Leu Gln Tyr Ala Glu Arg Val Trp Asn Ile Thr Glu Gly Ser Asp Asp
305                 310                 315                 320

Glu Arg Ile Asp Ala Ala Ile Ala Ala Thr Arg Asn Phe Phe Glu Gln
                325                 330                 335

Leu Gly Val Pro Thr His Leu Ser Asp Tyr Gly Leu Asp Gly Ser Ser
                340                 345                 350

Ile Pro Ala Leu Leu Lys Lys Leu Glu Glu His Gly Met Thr Gln Leu
                355                 360                 365

Gly Glu Asn His Asp Ile Thr Leu Asp Val Ser Arg Arg Ile Tyr Glu
                370                 375                 380

Ala Ala Arg
385

<210> SEQ ID NO 5
<211> LENGTH: 387
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (37)..(38)
<223> OTHER INFORMATION: Gly, Ile, Tyr, Val, Leu, Phe, or any other
      conservative amino acid substitution described in the
      specification
<220> FEATURE:
<221> NAME/KEY: MOD_RES
<222> LOCATION: (39)..(40)
<223> OTHER INFORMATION: Xaa at position 39 and 40 can be any useful
      amino acid substitution (e.g., Ile at position 39 and Arg at
      position 40; Tyr at position 39 and His at position 40; as well as
      any other conservative amino acid substitution described in the
      specification)

<400> SEQUENCE: 5

Met Asn Asn Phe Asn Leu His Thr Pro Thr Arg Ile Leu Phe Gly Lys
1               5                   10                  15

Gly Ala Ile Ala Gly Leu Arg Glu Gln Ile Pro His Asp Ala Arg Val
                20                  25                  30

Leu Ile Thr Tyr Xaa Xaa Xaa Xaa Val Lys Lys Thr Gly Val Leu Asp
                35                  40                  45

Gln Val Leu Asp Ala Leu Lys Gly Met Asp Val Leu Glu Phe Gly Gly
            50                  55                  60

Ile Glu Pro Asn Pro Ala Tyr Glu Thr Leu Met Asn Ala Val Lys Leu
65                  70                  75                  80
```

Val Arg Glu Gln Lys Val Thr Phe Leu Leu Ala Val Gly Gly Ser
                85                  90                  95

Val Leu Asp Gly Thr Lys Phe Ile Ala Ala Ala Asn Tyr Pro Glu
            100                 105                 110

Asn Ile Asp Pro Trp His Ile Leu Gln Thr Gly Gly Lys Glu Ile Lys
            115                 120                 125

Ser Ala Ile Pro Met Gly Cys Val Leu Thr Leu Pro Ala Thr Gly Ser
        130                 135                 140

Glu Ser Asn Ala Gly Ala Val Ile Ser Arg Lys Thr Thr Gly Asp Lys
145                 150                 155                 160

Gln Ala Phe His Ser Ala His Val Gln Pro Val Phe Ala Val Leu Asp
                165                 170                 175

Pro Val Tyr Thr Tyr Thr Leu Pro Pro Arg Gln Val Ala Asn Gly Val
            180                 185                 190

Val Asp Ala Phe Val His Thr Val Glu Gln Tyr Val Thr Lys Pro Val
            195                 200                 205

Asp Ala Lys Ile Gln Asp Arg Phe Ala Glu Gly Ile Leu Leu Thr Leu
        210                 215                 220

Ile Glu Asp Gly Pro Lys Ala Leu Lys Glu Pro Glu Asn Tyr Asp Val
225                 230                 235                 240

Arg Ala Asn Val Met Trp Ala Ala Thr Gln Ala Leu Asn Gly Leu Ile
                245                 250                 255

Gly Ala Gly Val Pro Gln Asp Trp Ala Thr His Met Leu Gly His Glu
            260                 265                 270

Leu Thr Ala Met His Gly Leu Asp His Ala Gln Thr Leu Ala Ile Val
        275                 280                 285

Leu Pro Ala Leu Trp Asn Glu Lys Arg Asp Thr Lys Arg Ala Lys Leu
290                 295                 300

Leu Gln Tyr Ala Glu Arg Val Trp Asn Ile Thr Glu Gly Ser Asp Asp
305                 310                 315                 320

Glu Arg Ile Asp Ala Ala Ile Ala Ala Thr Arg Asn Phe Phe Glu Gln
                325                 330                 335

Leu Gly Val Pro Thr His Leu Ser Asp Tyr Gly Leu Asp Gly Ser Ser
            340                 345                 350

Ile Pro Ala Leu Leu Lys Lys Leu Glu Glu His Gly Met Thr Gln Leu
        355                 360                 365

Gly Glu Asn His Asp Ile Thr Leu Asp Val Ser Arg Arg Ile Tyr Glu
370                 375                 380

Ala Ala Arg
385

<210> SEQ ID NO 6
<211> LENGTH: 491
<212> TYPE: PRT
<213> ORGANISM: Escherichia coli

<400> SEQUENCE: 6

Met Ala Asn Tyr Phe Asn Thr Leu Asn Leu Arg Gln Gln Leu Ala Gln
1               5                   10                  15

Leu Gly Lys Cys Arg Phe Met Gly Arg Asp Glu Phe Ala Asp Gly Ala
            20                  25                  30

Ser Tyr Leu Gln Gly Lys Lys Val Val Ile Val Gly Cys Gly Ala Gln
        35                  40                  45

Gly Leu Asn Gln Gly Leu Asn Met Arg Asp Ser Gly Leu Asp Ile Ser
    50                  55                  60

```
Tyr Ala Leu Arg Lys Glu Ala Ile Ala Glu Lys Arg Ala Ser Trp Arg
 65                  70                  75                  80

Lys Ala Thr Glu Asn Gly Phe Lys Val Gly Thr Tyr Glu Glu Leu Ile
                 85                  90                  95

Pro Gln Ala Asp Leu Val Ile Asn Leu Thr Pro Asp Lys Gln His Ser
                100                 105                 110

Asp Val Val Arg Thr Val Gln Pro Leu Met Lys Asp Gly Ala Ala Leu
                115                 120                 125

Gly Tyr Ser His Gly Phe Asn Ile Val Glu Val Gly Glu Gln Ile Arg
                130                 135                 140

Lys Asp Ile Thr Val Val Met Val Ala Pro Lys Cys Pro Gly Thr Glu
145                 150                 155                 160

Val Arg Glu Glu Tyr Lys Arg Gly Phe Gly Val Pro Thr Leu Ile Ala
                165                 170                 175

Val His Pro Glu Asn Asp Pro Lys Gly Glu Gly Met Ala Ile Ala Lys
                180                 185                 190

Ala Trp Ala Ala Thr Gly Gly His Arg Ala Gly Val Leu Glu Ser
                195                 200                 205

Ser Phe Val Ala Glu Val Lys Ser Asp Leu Met Gly Glu Gln Thr Ile
210                 215                 220

Leu Cys Gly Met Leu Gln Ala Gly Ser Leu Leu Cys Phe Asp Lys Leu
225                 230                 235                 240

Val Glu Glu Gly Thr Asp Pro Ala Tyr Ala Glu Lys Leu Ile Gln Phe
                245                 250                 255

Gly Trp Glu Thr Ile Thr Glu Ala Leu Lys Gln Gly Gly Ile Thr Leu
                260                 265                 270

Met Met Asp Arg Leu Ser Asn Pro Ala Lys Leu Arg Ala Tyr Ala Leu
                275                 280                 285

Ser Glu Gln Leu Lys Glu Ile Met Ala Pro Leu Phe Gln Lys His Met
290                 295                 300

Asp Asp Ile Ile Ser Gly Glu Phe Ser Ser Gly Met Met Ala Asp Trp
305                 310                 315                 320

Ala Asn Asp Asp Lys Lys Leu Leu Thr Trp Arg Glu Glu Thr Gly Lys
                325                 330                 335

Thr Ala Phe Glu Thr Ala Pro Gln Tyr Glu Gly Lys Ile Gly Glu Gln
                340                 345                 350

Glu Tyr Phe Asp Lys Gly Val Leu Met Ile Ala Met Val Lys Ala Gly
                355                 360                 365

Val Glu Leu Ala Phe Glu Thr Met Val Asp Ser Gly Ile Ile Glu Glu
                370                 375                 380

Ser Ala Tyr Tyr Glu Ser Leu His Glu Leu Pro Leu Ile Ala Asn Thr
385                 390                 395                 400

Ile Ala Arg Lys Arg Leu Tyr Glu Met Asn Val Val Ile Ser Asp Thr
                405                 410                 415

Ala Glu Tyr Gly Asn Tyr Leu Phe Ser Tyr Ala Cys Val Pro Leu Leu
                420                 425                 430

Lys Pro Phe Met Ala Glu Leu Gln Pro Gly Asp Leu Gly Lys Ala Ile
                435                 440                 445

Pro Glu Gly Ala Val Asp Asn Gly Gln Leu Arg Asp Val Asn Glu Ala
                450                 455                 460

Ile Arg Ser His Ala Ile Glu Gln Val Gly Lys Lys Leu Arg Gly Tyr
465                 470                 475                 480
```

```
Met Thr Asp Met Lys Arg Ile Ala Val Ala Gly
                485                 490
```

```
<210> SEQ ID NO 7
<211> LENGTH: 491
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (71)..(71)
<223> OTHER INFORMATION: Ser or Thr at position 71
<220> FEATURE:
<221> NAME/KEY: MOD_RES
<222> LOCATION: (76)..(76)
<223> OTHER INFORMATION: Asp or Glu at position 76
<220> FEATURE:
<221> NAME/KEY: MOD_RES
<222> LOCATION: (78)..(78)
<223> OTHER INFORMATION: Asp or Glu at position 78
<220> FEATURE:
<221> NAME/KEY: MOD_RES
<222> LOCATION: (110)..(110)
<223> OTHER INFORMATION: Val or Ala or Leu or Ile at position 110
<220> FEATURE:
<221> NAME/KEY: MOD_RES
<222> LOCATION: (146)..(146)
<223> OTHER INFORMATION: Gly or Ala at position 146
<220> FEATURE:
<221> NAME/KEY: MOD_RES
<222> LOCATION: (185)..(185)
<223> OTHER INFORMATION: Arg or Lys at position 185
<220> FEATURE:
<221> NAME/KEY: MOD_RES
<222> LOCATION: (433)..(433)
<223> OTHER INFORMATION: Glu or Asp at position 433

<400> SEQUENCE: 7

Met Ala Asn Tyr Phe Asn Thr Leu Asn Leu Arg Gln Gln Leu Ala Gln
1               5                   10                  15

Leu Gly Lys Cys Arg Phe Met Gly Arg Asp Glu Phe Ala Asp Gly Ala
            20                  25                  30

Ser Tyr Leu Gln Gly Lys Lys Val Ile Val Gly Cys Gly Ala Gln
        35                  40                  45

Gly Leu Asn Gln Gly Leu Asn Met Arg Asp Ser Gly Leu Asp Ile Ser
    50                  55                  60

Tyr Ala Leu Arg Lys Glu Xaa Ile Ala Glu Lys Xaa Ala Xaa Trp Arg
65                  70                  75                  80

Lys Ala Thr Glu Asn Gly Phe Lys Val Gly Thr Tyr Glu Glu Leu Ile
                85                  90                  95

Pro Gln Ala Asp Leu Val Ile Asn Leu Thr Pro Asp Lys Xaa His Ser
            100                 105                 110

Asp Val Val Arg Thr Val Gln Pro Leu Met Lys Asp Gly Ala Ala Leu
        115                 120                 125

Gly Tyr Ser His Gly Phe Asn Ile Val Glu Val Gly Glu Gln Ile Arg
    130                 135                 140

Lys Xaa Ile Thr Val Val Met Val Ala Pro Lys Cys Pro Gly Thr Glu
145                 150                 155                 160

Val Arg Glu Glu Tyr Lys Arg Gly Phe Gly Val Pro Thr Leu Ile Ala
                165                 170                 175

Val His Pro Glu Asn Asp Pro Lys Xaa Glu Gly Met Ala Ile Ala Lys
            180                 185                 190

Ala Trp Ala Ala Ala Thr Gly Gly His Arg Ala Gly Val Leu Glu Ser
        195                 200                 205
```

Ser Phe Val Ala Glu Val Lys Ser Asp Leu Met Gly Glu Gln Thr Ile
    210                 215                 220

Leu Cys Gly Met Leu Gln Ala Gly Ser Leu Leu Cys Phe Asp Lys Leu
225                 230                 235                 240

Val Glu Glu Gly Thr Asp Pro Ala Tyr Ala Glu Lys Leu Ile Gln Phe
                245                 250                 255

Gly Trp Glu Thr Ile Thr Glu Ala Leu Lys Gln Gly Gly Ile Thr Leu
                260                 265                 270

Met Met Asp Arg Leu Ser Asn Pro Ala Lys Leu Arg Ala Tyr Ala Leu
            275                 280                 285

Ser Glu Gln Leu Lys Glu Ile Met Ala Pro Leu Phe Gln Lys His Met
    290                 295                 300

Asp Asp Ile Ile Ser Gly Glu Phe Ser Ser Gly Met Met Ala Asp Trp
305                 310                 315                 320

Ala Asn Asp Asp Lys Lys Leu Leu Thr Trp Arg Glu Glu Thr Gly Lys
                325                 330                 335

Thr Ala Phe Glu Thr Ala Pro Gln Tyr Glu Gly Lys Ile Gly Glu Gln
                340                 345                 350

Glu Tyr Phe Asp Lys Gly Val Leu Met Ile Ala Met Val Lys Ala Gly
            355                 360                 365

Val Glu Leu Ala Phe Glu Thr Met Val Asp Ser Gly Ile Ile Glu Glu
    370                 375                 380

Ser Ala Tyr Tyr Glu Ser Leu His Glu Leu Pro Leu Ile Ala Asn Thr
385                 390                 395                 400

Ile Ala Arg Lys Arg Leu Tyr Glu Met Asn Val Val Ile Ser Asp Thr
                405                 410                 415

Ala Glu Tyr Gly Asn Tyr Leu Phe Ser Tyr Ala Cys Val Pro Leu Leu
                420                 425                 430

Xaa Pro Phe Met Ala Glu Leu Gln Pro Gly Asp Leu Gly Lys Ala Ile
            435                 440                 445

Pro Glu Gly Ala Val Asp Asn Gly Gln Leu Arg Asp Val Asn Glu Ala
    450                 455                 460

Ile Arg Ser His Ala Ile Glu Gln Val Gly Lys Lys Leu Arg Gly Tyr
465                 470                 475                 480

Met Thr Asp Met Lys Arg Ile Ala Val Ala Gly
                485                 490

<210> SEQ ID NO 8

<400> SEQUENCE: 8

000

<210> SEQ ID NO 9

<400> SEQUENCE: 9

000

<210> SEQ ID NO 10
<211> LENGTH: 41
<212> TYPE: DNA
<213> ORGANISM: Artificial Sequence
<220> FEATURE:
<223> OTHER INFORMATION: Synthetic construct

<400> SEQUENCE: 10
ctcagcgaat tcatgaacaa ctttaatctg cacaccccaa c           41

<210> SEQ ID NO 11
<211> LENGTH: 35
<212> TYPE: DNA
<213> ORGANISM: Artificial Sequence
<220> FEATURE:
<223> OTHER INFORMATION: Synthetic construct

<400> SEQUENCE: 11
tgacctggat ccttagcggg cggcttcgta tatac                  35

<210> SEQ ID NO 12
<211> LENGTH: 43
<212> TYPE: DNA
<213> ORGANISM: Artificial Sequence
<220> FEATURE:
<223> OTHER INFORMATION: Synthetic construct

<400> SEQUENCE: 12
ctcagcgaat tcatggctaa ctacttcaat acactgaatc tgc          43

<210> SEQ ID NO 13
<211> LENGTH: 37
<212> TYPE: DNA
<213> ORGANISM: Artificial Sequence
<220> FEATURE:
<223> OTHER INFORMATION: Synthetic construct

<400> SEQUENCE: 13
tgacctggat ccttaacccg caacagcaat acgtttc                 37

<210> SEQ ID NO 14
<211> LENGTH: 48
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (25)..(27)
<223> OTHER INFORMATION: n can be any nucleic acid to create mutant
      library S40

<400> SEQUENCE: 14
gtattgatta cctacggcgg cggcnnngtg aaaaaaaccg gcgttctc     48

<210> SEQ ID NO 15
<211> LENGTH: 48
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (22)..(24)
<223> OTHER INFORMATION: n can be any nucleic acid to create mutant
      library S40

<400> SEQUENCE: 15
gagaacgccg gtttttttca cnnngccgcc gccgtaggta atcaatac    48

<210> SEQ ID NO 16
<211> LENGTH: 48
<212> TYPE: DNA
<213> ORGANISM: Artificial Sequence
<220> FEATURE:
<223> OTHER INFORMATION: Synthetic construct

```
<220> FEATURE:
<221> NAME/KEY: misc_feature
<222> LOCATION: (22)..(27)
<223> OTHER INFORMATION: n can be any nucleic acid to create mutant
      library G39S40

<400> SEQUENCE: 16
gtattgatta cctacggcgg cnnnnnngtg aaaaaaaccg gcgttctc                    48

<210> SEQ ID NO 17
<211> LENGTH: 48
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (22)..(27)
<223> OTHER INFORMATION: n can be any nucleic acid to create mutant
      library G39S40

<400> SEQUENCE: 17
gagaacgccg gttttttttca cnnnnnngcc gccgtaggta atcaatac                   48

<210> SEQ ID NO 18
<211> LENGTH: 45
<212> TYPE: DNA
<213> ORGANISM: Artificial Sequence
<220> FEATURE:
<223> OTHER INFORMATION: Synthetic construct

<400> SEQUENCE: 18
gtattgatta cctacggcgg cccggtgaaa aaaaccggcg ttctc                       45

<210> SEQ ID NO 19
<211> LENGTH: 45
<212> TYPE: DNA
<213> ORGANISM: Artificial Sequence
<220> FEATURE:
<223> OTHER INFORMATION: Synthetic construct

<400> SEQUENCE: 19
gagaacgccg gttttttttca ccgggccgcc gtaggtaatc aatac                      45

<210> SEQ ID NO 20
<211> LENGTH: 45
<212> TYPE: DNA
<213> ORGANISM: Artificial Sequence
<220> FEATURE:
<223> OTHER INFORMATION: Synthetic construct

<400> SEQUENCE: 20
gtattgatta cctacggcgg ccgtgtgaaa aaaaccggcg ttctc                       45

<210> SEQ ID NO 21
<211> LENGTH: 45
<212> TYPE: DNA
<213> ORGANISM: Artificial Sequence
<220> FEATURE:
<223> OTHER INFORMATION: Synthetic construct

<400> SEQUENCE: 21
gagaacgccg gttttttttca ccgtgccgcc gtaggtaatc aatac                      45

<210> SEQ ID NO 22
<211> LENGTH: 48
<212> TYPE: DNA
```

```
<213> ORGANISM: Artificial Sequence
<220> FEATURE:
<223> OTHER INFORMATION: Synthetic construct

<400> SEQUENCE: 22
gtattgatta cctacggcgg catccgtgtg aaaaaaaccg gcgttctc            48

<210> SEQ ID NO 23
<211> LENGTH: 48
<212> TYPE: DNA
<213> ORGANISM: Artificial Sequence
<220> FEATURE:
<223> OTHER INFORMATION: Synthetic construct

<400> SEQUENCE: 23
gagaacgccg gttttttca cacggatgcc gccgtaggta atcaatac             48

<210> SEQ ID NO 24
<211> LENGTH: 48
<212> TYPE: DNA
<213> ORGANISM: Artificial Sequence
<220> FEATURE:
<223> OTHER INFORMATION: Synthetic construct

<400> SEQUENCE: 24
gtattgatta cctacggcgg ctatcatgtg aaaaaaaccg gcgttctc            48

<210> SEQ ID NO 25
<211> LENGTH: 48
<212> TYPE: DNA
<213> ORGANISM: Artificial Sequence
<220> FEATURE:
<223> OTHER INFORMATION: Synthetic construct

<400> SEQUENCE: 25
gagaacgccg gttttttca catgatagcc gccgtaggta atcaatac             48

<210> SEQ ID NO 26
<211> LENGTH: 36
<212> TYPE: DNA
<213> ORGANISM: Artificial Sequence
<220> FEATURE:
<223> OTHER INFORMATION: Synthetic construct

<400> SEQUENCE: 26
cgtaaagaat cgattgccga aaggatgcg gattgg                          36

<210> SEQ ID NO 27
<211> LENGTH: 36
<212> TYPE: DNA
<213> ORGANISM: Artificial Sequence
<220> FEATURE:
<223> OTHER INFORMATION: Synthetic construct

<400> SEQUENCE: 27
ccaatccgca tccttctcgg caatcgattc tttacg                         36

<210> SEQ ID NO 28
<211> LENGTH: 24
<212> TYPE: DNA
<213> ORGANISM: Artificial Sequence
<220> FEATURE:
<223> OTHER INFORMATION: Synthetic construct

<400> SEQUENCE: 28
cggacaaggc gcactctgat gtag                                      24
```

<210> SEQ ID NO 29
<211> LENGTH: 24
<212> TYPE: DNA
<213> ORGANISM: Artificial Sequence
<220> FEATURE:
<223> OTHER INFORMATION: Synthetic construct

<400> SEQUENCE: 29
ctacatcaga gtgcgccttg tccg                                    24

<210> SEQ ID NO 30
<211> LENGTH: 24
<212> TYPE: DNA
<213> ORGANISM: Artificial Sequence
<220> FEATURE:
<223> OTHER INFORMATION: Synthetic construct

<400> SEQUENCE: 30
cggacaaggt gcactctgat gtag                                    24

<210> SEQ ID NO 31
<211> LENGTH: 24
<212> TYPE: DNA
<213> ORGANISM: Artificial Sequence
<220> FEATURE:
<223> OTHER INFORMATION: Synthetic construct

<400> SEQUENCE: 31
ctacatcaga gtgcaccttg tccg                                    24

<210> SEQ ID NO 32
<211> LENGTH: 60
<212> TYPE: DNA
<213> ORGANISM: Artificial Sequence
<220> FEATURE:
<223> OTHER INFORMATION: Synthetic construct

<400> SEQUENCE: 32
gaaagctctc taggtcgacg aggaatcacc atggctaact acttcaatac actgaatctg    60

<210> SEQ ID NO 33
<211> LENGTH: 60
<212> TYPE: DNA
<213> ORGANISM: Artificial Sequence
<220> FEATURE:
<223> OTHER INFORMATION: Synthetic construct

<400> SEQUENCE: 33
gtacttaggc atggtatatc tccttccggg ttaacccgca acagcaatac gtttcatatc    60

<210> SEQ ID NO 34
<211> LENGTH: 60
<212> TYPE: DNA
<213> ORGANISM: Artificial Sequence
<220> FEATURE:
<223> OTHER INFORMATION: Synthetic construct

<400> SEQUENCE: 34
gatatgaaac gtattgctgt tgcgggttaa cccggaagga gatataccat gcctaagtac    60

<210> SEQ ID NO 35
<211> LENGTH: 60
<212> TYPE: DNA
<213> ORGANISM: Artificial Sequence
<220> FEATURE:

<223> OTHER INFORMATION: Synthetic construct

<400> SEQUENCE: 35
ggatttgtcc tactcaggag agcgttcacc gacaaacaac agataaaacg aaaggcccag    60

<210> SEQ ID NO 36
<211> LENGTH: 60
<212> TYPE: DNA
<213> ORGANISM: Artificial Sequence
<220> FEATURE:
<223> OTHER INFORMATION: Synthetic construct

<400> SEQUENCE: 36
ctgggccttt cgttttatct gttgtttgtc ggtgaacgct ctcctgagta ggacaaatcc    60

<210> SEQ ID NO 37
<211> LENGTH: 60
<212> TYPE: DNA
<213> ORGANISM: Artificial Sequence
<220> FEATURE:
<223> OTHER INFORMATION: Synthetic construct

<400> SEQUENCE: 37
cagattcagt gtattgaagt agttagccat ggtgattcct cgtcgaccta gagagctttc    60

<210> SEQ ID NO 38
<211> LENGTH: 50
<212> TYPE: DNA
<213> ORGANISM: Artificial Sequence
<220> FEATURE:
<223> OTHER INFORMATION: Synthetic construct

<400> SEQUENCE: 38
ggagaaaggt cacatgaaca actttaatct gcacacccca acccgcattc                50

<210> SEQ ID NO 39
<211> LENGTH: 48
<212> TYPE: DNA
<213> ORGANISM: Artificial Sequence
<220> FEATURE:
<223> OTHER INFORMATION: Synthetic construct

<400> SEQUENCE: 39
ctctagcacg cgtaccatgg gatccttagc gggcggcttc gtatatac                  48

<210> SEQ ID NO 40
<211> LENGTH: 48
<212> TYPE: DNA
<213> ORGANISM: Artificial Sequence
<220> FEATURE:
<223> OTHER INFORMATION: Synthetic construct

<400> SEQUENCE: 40
gtatatacga agccgcccgc taaggatccc atggtacgcg tgctagag                  48

<210> SEQ ID NO 41
<211> LENGTH: 60
<212> TYPE: DNA
<213> ORGANISM: Artificial Sequence
<220> FEATURE:
<223> OTHER INFORMATION: Synthetic construct

<400> SEQUENCE: 41
catgataata atggtttctt agacgtcagg tggcactttt cggggaaatg tgcgcggaac    60

```
<210> SEQ ID NO 42
<211> LENGTH: 60
<212> TYPE: DNA
<213> ORGANISM: Artificial Sequence
<220> FEATURE:
<223> OTHER INFORMATION: Synthetic construct

<400> SEQUENCE: 42
gttccgcgca catttccccg aaaagtgcca cctgacgtct aagaaaccat tattatcatg    60

<210> SEQ ID NO 43
<211> LENGTH: 50
<212> TYPE: DNA
<213> ORGANISM: Artificial Sequence
<220> FEATURE:
<223> OTHER INFORMATION: Synthetic construct

<400> SEQUENCE: 43
gaatgcgggt tggggtgtgc agattaaagt tgttcatgtg acctttctcc                50
```

BIOCHEMICAL UPGRADING OF HIGH-PROTEIN BIOMASS AND GRAIN PRODUCTS

CROSS-REFERENCE TO RELATED APPLICATION

This application is a divisional application of parent patent application U.S. patent application Ser. No. 15/447,567, filed Mar. 2, 2017 and entitled "BIOCHEMICAL UPGRADING OF HIGH-PROTEIN BIOMASS AND GRAIN PRODUCTS", which claims priority to U.S. Provisional Patent Application Ser. No. 62/303,282, filed on Mar. 3, 2016, entitled "BIOCHEMICAL UPGRADING OF HIGH-PROTEIN BIOMASS AND GRAIN PRODUCTS". The present application claims the priority of its parent application, which is incorporated herein by reference in its entirety for any purpose.

STATEMENT OF GOVERNMENT INTEREST

This invention was made with Government support under contract no. DE-NA0003525 awarded by the U.S. Department of Energy to National Technology & Engineering Solutions of Sandia, LLC. The Government has certain rights in the invention.

REFERENCE TO A SEQUENCE LISTING APPENDIX

A sequence listing appendix including an ASCII formatted file accompanies this application. The appendix includes a file named "SD13872_1_Sequence_Listing_ST25.txt," created on May 17, 2017 (size of 34.1 kilobytes), which is hereby incorporated by reference in its entirety.

FIELD OF THE INVENTION

The present invention relates to methods of upgrading biomass to provide useful chemical intermediates, fuels, amino acids, nutrients, etc. In particular examples, the biomass is a by-product of ethanol production and is mainly used as high-protein feed. Described herein are methods for upgrading such biomass, such as by implementing pre-treatment conditions and by employing fermentation conditions including modified organisms.

BACKGROUND OF THE INVENTION

Production of distillers dried grains (DDGs), the primary co-product of residue from corn ethanol production, has dramatically increased since about 2002. Despite potential utility for this product for animal feed blending, market adoption of the feedstock has been limited due to inconsistent composition and potential toxicity to livestock. Such co-products, as well as other biomass products, can contain high value components that are difficult to recover and isolate. Accordingly, there is a need for methods and tools to facilitate such isolation in an effective and/or efficient manner.

SUMMARY OF THE INVENTION

The present invention relates to methods of upgrading biomass (e.g., distillers grains, oilseed meals, etc.) in order to provide higher value products, such as bioethanol, chemical intermediates, and valuable amino acids. In particular examples, the methods herein are employed with distillers dried grains (DDGs), a primary co-product from corn ethanol production with minimal market adoption. As described herein, we have developed a process for biochemical upgrading of DDGs for production of mixed alcohols (e.g., $C_{2-6}$ alcohols) for fuels and industrial chemicals, as well as high value amino acids (e.g., Lys, Met, His, Trp) for feed blending applications (e.g., as a fish meal replacement).

The methods herein include a pre-treatment step, as well as one or more fermentation step(s). In one non-limiting example, the pre-treatment step generally employs dilute acid hydrolysis, and the fermentation steps employ $E.\ coli$ fermentation modules, yielding about 40% of the organic basis to mixed alcohols and recovery of major nutrients (nitrogen and phosphorous) as struvite.

Fermentation can be inhibited by the presence of several chemical constituents. For instance, the presence of excess alcohol in the fermentation product can inhibit the functionality of the organism to, e.g., break down amino acids. In another non-limiting instance, cofactor imbalance can limit fermentation, e.g., in which the lack of a particular cofactor can result in limited yield of desired fermentation products. Thus, in some non-limiting methods herein, the biomass is treated in a manner to promote, rather than inhibit, fermentation, e.g., by providing two fermentation steps, in which the first step includes removal of excess alcohol and the second step includes break-down of proteins or amino acids; and, e.g., by providing a genetically modified organism suited for employing a cofactor that does not limit fermentation, such as an organism that is selected by direct evolution to have a non-native cofactor specificity.

The present invention also relates to genetically modified organisms (e.g., for employment in any fermentation step described herein). In particular, we describe two types of genetically modified $E.\ coli$ strains that were optimized for conversion of hydrolyzed carbohydrates and proteins, respectively.

The methods herein can be optimized to recover any useful component (e.g., biocomponent, intermediate, etc.). In one non-limiting example, the fermentation liquor was extracted with ethyl acetate to recover the mixed alcohols at about 90% yield, and the extraction solvent was recovered by distillation. Further lyophilization of the extracted fermentation liquor yielded a crystalline powder enriched with high value amino acids. Additional details follow.

Definitions

As used herein, the term "about" means +/−10% of any recited value. As used herein, this term modifies any recited value, range of values, or endpoints of one or more ranges.

The terms "polynucleotide" and "nucleic acid," used interchangeably herein, refer to a polymeric form of nucleotides of any length, either ribonucleotides or deoxyribonucleotides. Thus, this term includes, but is not limited to, single-stranded (e.g., sense or antisense), double-stranded, or multi-stranded ribonucleic acids (RNAs), deoxyribonucleic acids (DNAs), threose nucleic acids (TNAs), glycol nucleic acids (GNAs), peptide nucleic acids (PNAs), locked nucleic acids (LNAs), or hybrids thereof, genomic DNA, cDNA, DNA-RNA hybrids, or a polymer comprising purine and pyrimidine bases or other natural, chemically or biochemically modified, non-natural, or derivatized nucleotide bases. Polynucleotides can have any useful two-dimensional or three-dimensional structure or motif, such as regions including one or more duplex, triplex, quadruplex, hairpin, and/or pseudoknot structures or motifs.

The term "modified," as used in reference to nucleic acids, means a nucleic acid sequence including one or more modifications to the nucleobase, nucleoside, nucleotide, phosphate group, sugar group, and/or internucleoside linkage (e.g., phosphodiester backbone, linking phosphate, or a phosphodiester linkage).

The term "modified," as used in reference to amino acids, means an amino acid including one or more modifications, such as a post-translation modification (e.g., acetylation, methylation, phosphorylation, ubiquitination, sumoylation, ribosylation, glycosylation, acylation, or isomerization), or including a non-natural amino acid.

The term "modified," as used in reference to a protein, means a polypeptide sequence including one or more amino acid substitution, as compared to the reference sequence for the protein.

"Complementarity" or "complementary" or "complement" refers to the ability of a nucleic acid to form hydrogen bond(s) with another nucleic acid sequence by either traditional Watson-Crick or other non-traditional types, e.g., form Watson-Crick base pairs and/or G/U base pairs, "anneal", or "hybridize," to another nucleic acid in a sequence-specific, antiparallel, manner (i.e., a nucleic acid specifically binds to a complementary nucleic acid) under the appropriate in vitro and/or in vivo conditions of temperature and solution ionic strength. As is known in the art, standard Watson-Crick base-pairing includes: adenine (A) pairing with thymidine (T), adenine (A) pairing with uracil (U), and guanine (G) pairing with cytosine (C). In addition, it is also known in the art that for hybridization between two RNA molecules (e.g., dsRNA), guanine (G) base pairs with uracil (U). A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence. "Substantially complementary" or "sufficient complementarity" as used herein refers to a degree of complementarity that is at least 60%, 65%, 70%, 75%, 80%, 85%, 90%, 95%. 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions.

As used herein, "stringent conditions" for hybridization refer to conditions under which a nucleic acid having complementarity to a target sequence predominantly hybridizes with the target sequence, and substantially does not hybridize to non-target sequences. Stringent conditions are generally sequence-dependent and vary depending on a number of factors. In general, the longer the sequence, the higher the temperature at which the sequence specifically hybridizes to its target sequence. Non-limiting examples of stringent conditions are described in detail in Tijssen (1993), Laboratory Techniques In Biochemistry And Molecular Biology-Hybridization With Nucleic Acid Probes Part 1, Second Chapter "Overview of principles of hybridization and the strategy of nucleic acid probe assay", Elsevier, N.Y.

"Hybridization" refers to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence specific manner. The complex may comprise two strands forming a duplex structure, three or more strands forming a multi stranded complex, a single self-hybridizing strand, or any combination of these. A hybridization reaction may constitute a step in a more extensive process, such as the initiation of PCR, or the cleavage of a polynucleotide by an enzyme. A sequence capable of hybridizing with a given sequence is referred to as the "complement" of the given sequence. Hybridization and washing conditions are well known and exemplified in Sambrook J, Fritsch E F, and Maniatis T, "Molecular Cloning: A Laboratory Manual," Second Edition, Cold Spring Harbor Laboratory Press, Cold Spring Harbor (1989), particularly Chapter 11 and Table 11.1 therein; and Sambrook J and Russell W, "Molecular Cloning: A Laboratory Manual," Third Edition, Cold Spring Harbor Laboratory Press, Cold Spring Harbor (2001). The conditions of temperature and ionic strength determine the "stringency" of the hybridization.

Hybridization requires that the two nucleic acids contain complementary sequences, although mismatches between bases are possible. The conditions appropriate for hybridization between two nucleic acids depend on the length of the nucleic acids and the degree of complementation, variables well known in the art. The greater the degree of complementation between two nucleotide sequences, the greater the value of the melting temperature (Tm) for hybrids of nucleic acids having those sequences. For hybridizations between nucleic acids with short stretches of complementarity (e.g., complementarity over 35 or less, 30 or less, 25 or less, 22 or less, 20 or less, or 18 or less nucleotides) the position of mismatches becomes important (see Sambrook et al., supra, 11.7-11.8). Typically, the length for a hybridizable nucleic acid is at least about 10 nucleotides. Illustrative minimum lengths for a hybridizable nucleic acid are: at least about 15 nucleotides; at least about 20 nucleotides; at least about 22 nucleotides; at least about 25 nucleotides; and at least about 30 nucleotides). Furthermore, the skilled artisan will recognize that the temperature and wash solution salt concentration may be adjusted as necessary according to factors such as length of the region of complementation and the degree of complementation.

It is understood in the art that the sequence of polynucleotide need not be 100% complementary to that of its target nucleic acid to be specifically hybridizable or hybridizable. Moreover, a polynucleotide may hybridize over one or more segments such that intervening or adjacent segments are not involved in the hybridization event (e.g., a loop structure or hairpin structure). A polynucleotide can comprise at least 70%, at least 80%, at least 90%, at least 95%, at least 99%, or 100% sequence complementarity to a target region within the target nucleic acid sequence to which they are targeted. For example, an antisense nucleic acid in which 18 of 20 nucleotides of the antisense compound are complementary to a target region, and would therefore specifically hybridize, would represent 90 percent complementarity. In this example, the remaining noncomplementary nucleotides may be clustered or interspersed with complementary nucleotides and need not be contiguous to each other or to complementary nucleotides. Percent complementarity between particular stretches of nucleic acid sequences within nucleic acids can be determined routinely using BLAST programs (basic local alignment search tools) and PowerBLAST programs known in the art (Altschul S F et al., *J. Mol. Biol.* 1990; 215:403-10; Zhang J et al., *Genome Res.* 1997; 7:649-56) or by using the Gap program (Wisconsin Sequence Analysis Package, Version 8 for Unix, Genetics Computer Group, University Research Park, Madison Wis.), using default settings, which uses the algorithm of Smith T F et al., *Adv. Appl. Math.* 1981; 2(4):482-9).

By "protein," "peptide," or "polypeptide," as used interchangeably, is meant any chain of more than two amino acids, regardless of post-translational modification (e.g., glycosylation or phosphorylation), constituting all or part of a naturally occurring polypeptide or peptide, or constituting a non-naturally occurring polypeptide or peptide, which can include coded amino acids, non-coded amino acids, modified amino acids (e.g., chemically and/or biologically modified amino acids), and/or modified backbones.

The term "fragment" is meant a portion of a nucleic acid or a polypeptide that is at least one nucleotide or one amino acid shorter than the reference sequence. This portion contains, preferably, at least about 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, 1000, 1250, 1500, 1750, 1800 or more nucleotides; or 10, 20, 30, 40, 50, 60, 70, 80, 90, 100, 150, 200, 250, 300, 350, 400, 450, 500, 550, 600, 640 amino acids or more. In another example, any polypeptide fragment can include a stretch of at least about 5 (e.g., about 10, about 20, about 30, about 40, about 50, or about 100) amino acids that are at least about 40% (e.g., about 50%, about 60%, about 70%, about 80%, about 90%, about 95%, about 87%, about 98%, about 99%, or about 100%) identical to any of the sequences described herein can be utilized in accordance with the invention. In certain embodiments, a polypeptide to be utilized in accordance with the invention includes 2, 3, 4, 5, 6, 7, 8, 9, 10, or more mutations (e.g., one or more conservative amino acid substitutions, as described herein). In yet another example, any nucleic acid fragment can include a stretch of at least about 5 (e.g., about 7, about 8, about 10, about 12, about 14, about 18, about 20, about 24, about 28, about 30, or more) nucleotides that are at least about 40% (about 50%, about 60%, about 70%, about 80%, about 90%, about 95%, about 87%, about 98%, about 99%, or about 100%) identical to any of the sequences described herein can be utilized in accordance with the invention.

The term "conservative amino acid substitution" refers to the interchangeability in proteins of amino acid residues having similar side chains (e.g., of similar size, charge, and/or polarity). For example, a group of amino acids having aliphatic side chains consists of glycine (Gly, G), alanine (Ala, A), valine (Val, V), leucine (Leu, L), and isoleucine (Ile, I); a group of amino acids having aliphatic-hydroxyl side chains consists of serine (Ser, S) and threonine (Thr, T); a group of amino acids having amide containing side chains consisting of asparagine (Asn, N) and glutamine (Gln, Q); a group of amino acids having aromatic side chains consists of phenylalanine (Phe, F), tyrosine (Tyr, Y), and tryptophan (Trp, W); a group of amino acids having basic side chains consists of lysine (Lys, K), arginine (Arg, R), and histidine (His, H); a group of amino acids having acidic side chains consists of glutamic acid (Glu, E) and aspartic acid (Asp, D); and a group of amino acids having sulfur containing side chains consists of cysteine (Cys, C) and methionine (Met, M). Exemplary conservative amino acid substitution groups are valine-leucine-isoleucine, phenylalanine-tyrosine, lysine-arginine, alanine-valine, glycine-serine, glutamate-aspartate, and asparagine-glutamine.

As used herein, when a polypeptide or nucleic acid sequence is referred to as having "at least X % sequence identity" to a reference sequence, it is meant that at least X percent of the amino acids or nucleotides in the polypeptide or nucleic acid are identical to those of the reference sequence when the sequences are optimally aligned. An optimal alignment of sequences can be determined in various ways that are within the skill in the art, for instance, the Smith Waterman alignment algorithm (Smith T F et al., *J. Mol. Biol.* 1981; 147:195-7) and BLAST (Basic Local Alignment Search Tool; Altschul S F et al., *J. Mol. Biol.* 1990; 215:403-10). These and other alignment algorithms are accessible using publicly available computer software such as "Best Fit" (Smith T F et al., *Adv. Appl. Math.* 1981; 2(4):482-9) as incorporated into GeneMatcher Plus™ (Schwarz and Dayhof, "Atlas of Protein Sequence and Structure," ed. Dayhoff, M. O., pp. 353-358, 1979), BLAST, BLAST-2, BLAST-P, BLAST-N, BLAST-X, WU-BLAST-2, ALIGN, ALIGN-2, CLUSTAL, T-COFFEE, MUSCLE, MAFFT, or Megalign (DNASTAR). In addition, those skilled in the art can determine appropriate parameters for measuring alignment, including any algorithms needed to achieve optimal alignment over the length of the sequences being compared. In general, for polypeptides, the length of comparison sequences can be at least five amino acids, preferably 10, 20, 30, 40, 50, 60, 70, 80, 90, 100, 125, 150, 175, 200, 250, 300, 400, 500, 600, 700, or more amino acids, up to the entire length of the polypeptide. For nucleic acids, the length of comparison sequences can generally be at least 10, 20, 30, 40, 50, 60, 70, 80, 90, 100, 125, 150, 175, 200, 250, 300, 400, 500, 600, 700, 800, 900, 1000, 1100, 1200, 1300, 1400, 1500, 1600, 1700, 1800, 1900, 2000, 2100, or more nucleotides, up to the entire length of the nucleic acid molecule. It is understood that for the purposes of determining sequence identity when comparing a DNA sequence to an RNA sequence, a thymine nucleotide is equivalent to an uracil nucleotide.

By "substantial identity" or "substantially identical" is meant a polypeptide or nucleic acid sequence that has the same polypeptide or nucleic acid sequence, respectively, as a reference sequence, or has a specified percentage of amino acid residues or nucleotides, respectively, that are the same at the corresponding location within a reference sequence when the two sequences are optimally aligned. For example, an amino acid sequence that is "substantially identical" to a reference sequence has at least about 50%, 60%, 70%, 75%, 80%, 85%, 90%, 95%, 96%, 97%, 98%, 99%, or 100% sequence identity to the reference amino acid sequence. For polypeptides, the length of comparison sequences will generally be at least 5, 6, 7, 8, 9, 10, 11, 12, 13, 14, 15, 16, 17, 18, 19, 20, 25, 50, 75, 90, 100, 150, 200, 250, 300, or 350 contiguous amino acids (e.g., a full-length sequence). For nucleic acids, the length of comparison sequences will generally be at least 5, 10, 11, 12, 13, 14, 15, 16, 17, 18, 19, 20, 21, 22, 23, 24, or 25 contiguous nucleotides (e.g., the full-length nucleotide sequence). Sequence identity may be measured using sequence analysis software on the default setting (e.g., Sequence Analysis Software Package of the Genetics Computer Group, University of Wisconsin Biotechnology Center, 1710 University Avenue, Madison, Wis., 53705). Such software may match similar sequences by assigning degrees of homology to various substitutions, deletions, and other modifications.

A "vector" or "expression vector" is a replicon, such as plasmid, phage, virus, or cosmid, to which another nucleic acid segment, i.e., an "insert", may be attached so as to bring about the replication of the attached segment in a cell.

An "expression cassette" comprises a nucleic acid coding sequence operably linked, as defined herein, to a promoter sequence, as defined herein.

"Operably linked" or "operatively linked" or "operatively associated with," as used interchangeably, refers to a juxtaposition wherein the components so described are in a relationship permitting them to function in their intended manner. For instance, a promoter is operably linked to a coding sequence if the promoter affects its transcription or expression. A nucleic acid molecule is operatively linked or operably linked to, or operably associated with, an expression control sequence when the expression control sequence controls and regulates the transcription and translation of nucleic acid sequence. The term "operatively linked" includes having an appropriate start signal (e.g., ATG) in front of the nucleic acid sequence to be expressed and maintaining the correct reading frame to permit expression of the nucleic acid sequence under the control of the expression control sequence and production of the desired product encoded by the nucleic acid sequence. If a gene that one desires to insert into a recombinant DNA molecule does not contain an appropriate start signal, such a start signal can be inserted in front of the gene.

As used herein, the terms "top," "bottom," "upper," "lower," "above," and "below" are used to provide a relative relationship between structures. The use of these terms does not indicate or require that a particular structure must be located at a particular location in the apparatus.

Other features and advantages of the invention will be apparent from the following description and the claims.

BRIEF DESCRIPTION OF THE DRAWINGS

FIGS. 10A-10G shows the effects of cofactor engineering for E. coli alcohol dehydrogenase (YqhD). Provided are (A) an image showing structural alignment of the NADP-binding pocket for YqhD and (B) a graph showing mutant enzyme activity employing cofactor NADH, as compared to WT YqhD. Also provided are polypeptide sequences for E. coli YqhD, including sequences for (C) wild-type (SEQ ID NO:1) having Gly at positions 37-39 and Ser at position 40; (D) YqhD mutant 1 including a mutation at position 39 (SEQ ID NO:2), in which Xaa at position 39 can be any useful amino acid substitution (e.g., Ile, Tyr, Val, Leu, Phe, or any other conservative amino acid substitution described herein); (E) YqhD mutant 2 including a mutation at position 40 (SEQ ID NO:3), in which Xaa at position 40 can be any useful amino acid substitution (e.g., Pro, Arg, His, Lys, Trp, or any other conservative amino acid substitution described herein); (F) YqhD mutant 3 including a mutation at both positions 39 and 40 (SEQ ID NO:4), in which Xaa at position 39 and 40 can be any useful amino acid substitution (e.g., Ile at position 39 and Arg at position 40; Tyr at position 39 and His at position 40; as well as any other conservative amino acid substitution described herein); and (G) YqhD mutant 3 including a mutation at positions 39 and 40 (SEQ ID NO:5) with an optional substitution at positions 37 and 38, in which Xaa at position 39 and 40 can be any useful amino acid substitution (e.g., Ile at position 39 and Arg at position 40; Tyr at position 39 and His at position 40; as well as any other conservative amino acid substitution described herein). In some instances, the mutant (e.g., of SEQ ID NO:2-5) includes Gly, Ile, Tyr, Val, Leu, Phe, or any other conservative amino acid substitution described herein, for positions 37, 38, and 39; and Ser, Pro, Arg, His, Lys, Trp, or any other conservative amino acid substitution described herein for position 40 (e.g., in which position 39 and/or 40 includes an amino acid substitution as compared to the wild-type sequence, e.g., SEQ ID NO:1).

FIGS. 11A-11B provides polypeptide sequences for E. coli ketol-acid reductoisomerase IlvC, including sequences for (A) wild-type (SEQ ID NO:6) having Ala at position 71, Arg at position 76, Ser at position 78, Gln at position 110, Asp at position 146, Gly at position 185, and Lys at position 433; and (B) IlvC mutant including a mutation at positions 71, 76, 78, and/or 110 (SEQ ID NO:7). Exemplary substitutions include Ser or Thr at position 71, Asp or Glu at position 76, Asp or Glu at position 78, and/or Val or Ala or Leu or Ile at position 110, as well as any other conservative amino acid substitution described herein. Optionally, SEQ ID NO:7 can include other substitutions, including Gly or Ala at position 146, Arg or Lys at position 185, and/or Glu or Asp at position 433.

DETAILED DESCRIPTION OF THE INVENTION

The present invention relates to the upgrading biomass (e.g., high-protein biomass) into ethanol and other useful intermediates, such as amino acids, bioresidue, etc. Such intermediates, in turn, can be suitable for any useful industrial process, such as downstream refining, e.g., using known petrochemical facilities and processes. In particular embodiments, an exemplary process of the invention combines pre-treatment of the biomass to solubilize and hydrolyze the carbohydrate and protein fractions; followed by fermentation and optional distillation/extraction to recover useful alcohols, amino acids, etc. In some embodiments, the process employs biochemical steps to effectively solubilize, hydrolyze, and/or degrade components of the biomass (e.g., by employing a genetically engineered organism, such as any herein).

Figure 1A:
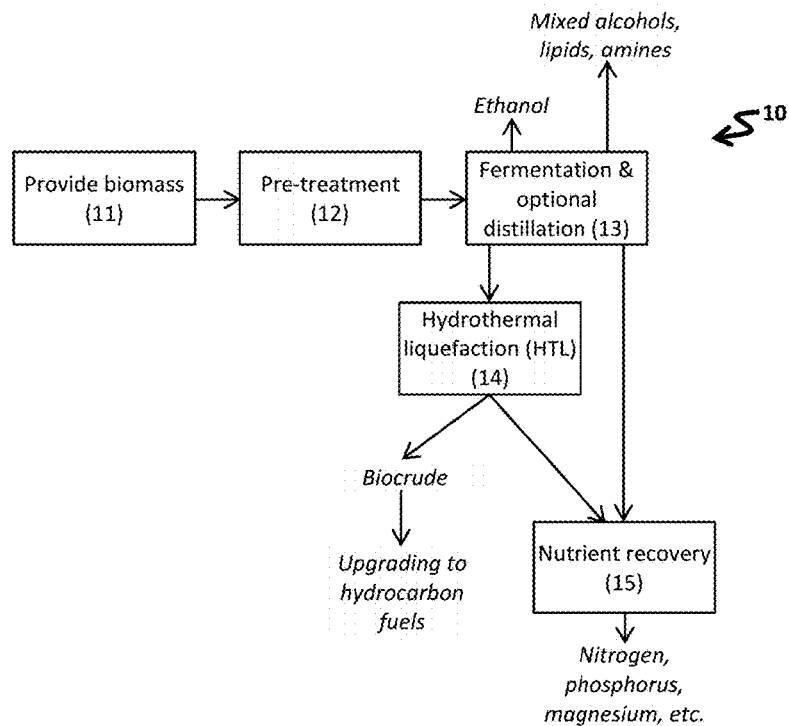
FIGS. 1A-1C shows exemplary process flow diagrams for upgrading biomass. Provided are (A) an exemplary process 10 including processing pathways and (B) another exemplary process 100 including a pre-treatment step 121,122 prior to each fermentation step 131,132. The unit operations of the process are depicted as designated boxes, where inputs and outputs are designated by arrows leading either into or away from a box, respectively. Also provided is (C) an exemplary process 1000 with an optional second pre-treatment step 1022.

An exemplary process 10 is shown in FIG. 1A. A biomass 11 is provided, typically including fractions of proteins, carbohydrates, and/or lipids (collectively, biocomponents). Further treatment steps can be employed to breakdown these biocomponents into useful residuals. Exemplary steps include pre-treatment 12 (e.g., employing dilute acid and/or enzymes in sequential or simultaneous steps) to hydrolyze and/or solubilize the biocomponents (e.g., such as to provide one or more sugars, including glucose, xylose, arabinose, etc.); as well as fermentation and optional distillation 13 to degrade the biocomponents into one or more alcohols (e.g., ethanol, 1-propanol, isobutanol, 1-butanol, 2-methyl-1-butanol, 3-methyl-1-butanol, 2-phenylethanol, isopentanol, etc.), amino acids, and amines.

Fermentation is typically employed to degrade sugars, carbohydrates, and proteins into further, smaller chemical components, such as alcohols, amino acids, and amines. In use, fermentation employs one or more organisms, such as bacteria or yeast, to degrade these biocomponents. Exemplary organisms are described herein (e.g., bacteria such as *E. coli*, as well as mutant forms that are selected to degrade sugars, carbohydrates, and/or proteins in a selective, specific, and/or useful manner). Typically, such organisms do not degrade lipids. Thus, conventional fermentation is usually conducted in aqueous, non-lipid samples. In some embodiments of the invention herein, organisms can be genetically modified to convert lipids. In other embodiments of the invention herein, the fermentation step includes use of one or more lipids, lipid vesicles, and/or lipid micelles within the fermentation broth.

After fermentation, one or more by-products (e.g., minerals, nutrients, water, etc.) can be optionally removed from any of the fractions. Nutrients, by-products, and water can be extracted within any point of the processing stream and with any useful mixture obtained within the processing stream. Such extraction steps can include removal of by-products from the fermentation broth or a portion thereof, delivery of nitrogen (N) and/or phosphorous (P) sources (e.g., as a salt, a mineral, etc.), and/or delivery of water. Any fractions obtained from these biocomponents can be processed to recovery nutrients (e.g., N and/or P) in any useful form, such as a protonated form (e.g., ammonia for capturing N), an oxide form (e.g., phosphate for capturing P), a salt form, and/or a mineral (e.g., struvite for capturing N and P).

In other examples, after the fermentation step, the aqueous and non-aqueous (e.g., lipid) fractions are phase-separated and processed in parallel steps. For instance, the non-aqueous fraction, including a bioresidue (e.g., a low nitrogen organic residue) composed of one or more lipids, can be treated by way of hydrothermal liquefaction (HTL) 14 to provide a biocrude oil. Any solid residuals, such as ash or char, can be removed after liquefaction. Any liquid residuals can be further processed to recover 15 any useful nutrients.

In another example, the aqueous fraction (e.g., including water-soluble components) can be distilled to remove alcohols (e.g., along with neutral lipids). Optionally, such fractions or extracted fractions can be further processed to recover any useful nutrients 15 (e.g., for recovering nitrogen and/or phosphorus) or usable water 16 (e.g., for use in multi-pass recycle operations) in the aqueous phase, as well as to extract any lipids present in the aqueous phase.

Any useful thermochemical process can be employed to process a bioresidue into a biocrude oil. Exemplary thermochemical processes include liquefaction, pyrolysis, gasification, and/or combustion in the optional presence of one or more catalysts. Experimental conditions (e.g., temperature, pressure, air composition, reactants, reagents, etc.) can be optimized in any useful manner to achieve the desired biocrude oil with appropriate viscosity, color, oxygen content, nitrogen content, etc. In addition, the biocrude oil can be further upgraded into biofuels, such as by use of hydrotreatment (e.g., as described herein).

Figure 1B:
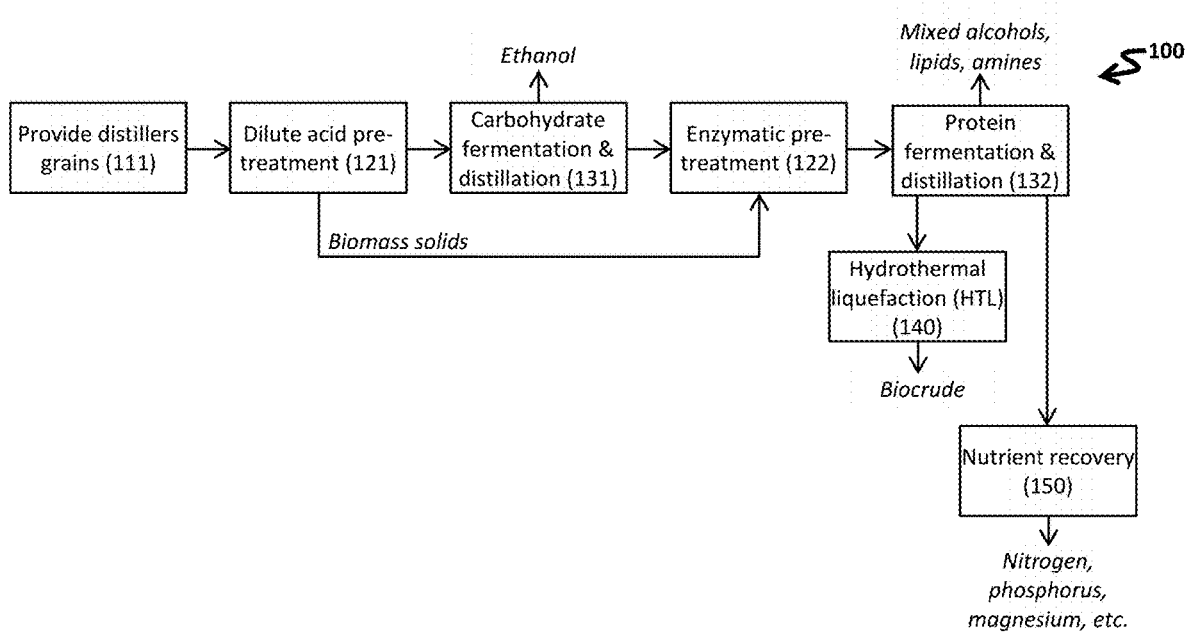

Yet another upgrading process 100 is shown in FIG. 1B, which provides a pre-treatment step 121,122 prior to each fermentation step 131,132. Overall, the exemplary non-limiting process 100 includes providing 111 a biomass (e.g., distillers grain); pre-treating 121 the biomass (e.g., with a dilute acid pre-treatment) and optionally separating a biomass solid; fermenting 131 the carbohydrate fraction (e.g., including one or more sugars) of the biocomponents with a genetically engineered organism useful for degrading carbohydrates (e.g., thereby producing ethanol) with optional distillation (e.g., of the produced ethanol); pre-treating 122 the biomass (e.g., with one or more enzymes); fermenting 132 the protein fraction (e.g., including one or more proteins, peptides, and/or amino acids) of the biocomponents with a genetically engineered organism useful for degrading amino acids (e.g., thereby producing one or more mixed alcohols, lipids, amino acids, and/or amines) with optional distillation (e.g., of the produced mixed alcohols); liquefying 140 any residual or fraction of a fermentation product (e.g., by way of hydrothermal liquefaction, thereby producing a biocrude); and recovering 150 any residual or fraction of a fermentation product (e.g., thereby producing a nutrient, such as nitrogen, phosphorous, magnesium etc.).

Pre-treatment can be employed to release various biocomponents from biomass that can be difficult to process. In addition, the process can include separated fermentation steps, in which each step can be optimized or selected to degrade a particular type of biocomponent. As seen in FIG.

1B, the process 100 includes a first fermentation step 131 useful for degrading sugar and carbohydrate components, thereby producing ethanol; and a second fermentation step 132 useful for degrading protein and amino acid components, thereby producing mixed alcohols, amines, and released amino acids.

Each pre-treatment step can be optionally followed by a separation step, such as by separating one or more solid components from a liquid portion. The liquid portion can be further processed (e.g., by fermentation), and the separated solid components can be re-introduced into the process at a later step in the processing pathway (e.g., enzymatic pre-treatment).

Figure 1C:
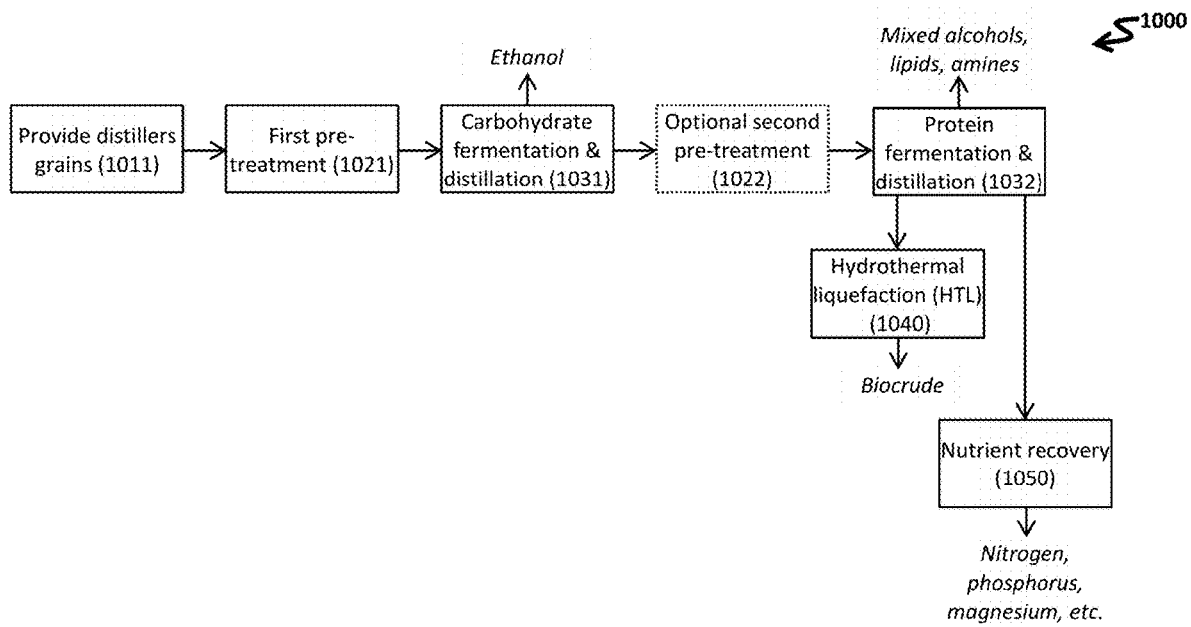

A second pre-treatment step can be optional. FIG. 1C shows another exemplary upgrading process 1000 that includes providing 1011 a biomass (e.g., distillers grain); pre-treating 1021 the biomass (e.g., with a dilute acid pre-treatment); fermenting 1031 the carbohydrate fraction (e.g., including one or more sugars) with optional distillation (e.g., of the produced ethanol); optionally pre-treating 1022 the biomass (e.g., with one or more enzymes); fermenting 1032 the protein fraction (e.g., including one or more proteins, peptides, and/or amino acids) with optional distillation (e.g., of the produced mixed alcohols); liquefying 1040 any residual or fraction of a fermentation product (e.g., by way of hydrothermal liquefaction, thereby producing a biocrude); and recovering 1050 any residual or fraction of a fermentation product (e.g., thereby producing a nutrient, such as nitrogen, phosphorous, magnesium etc.)

Figure 2:
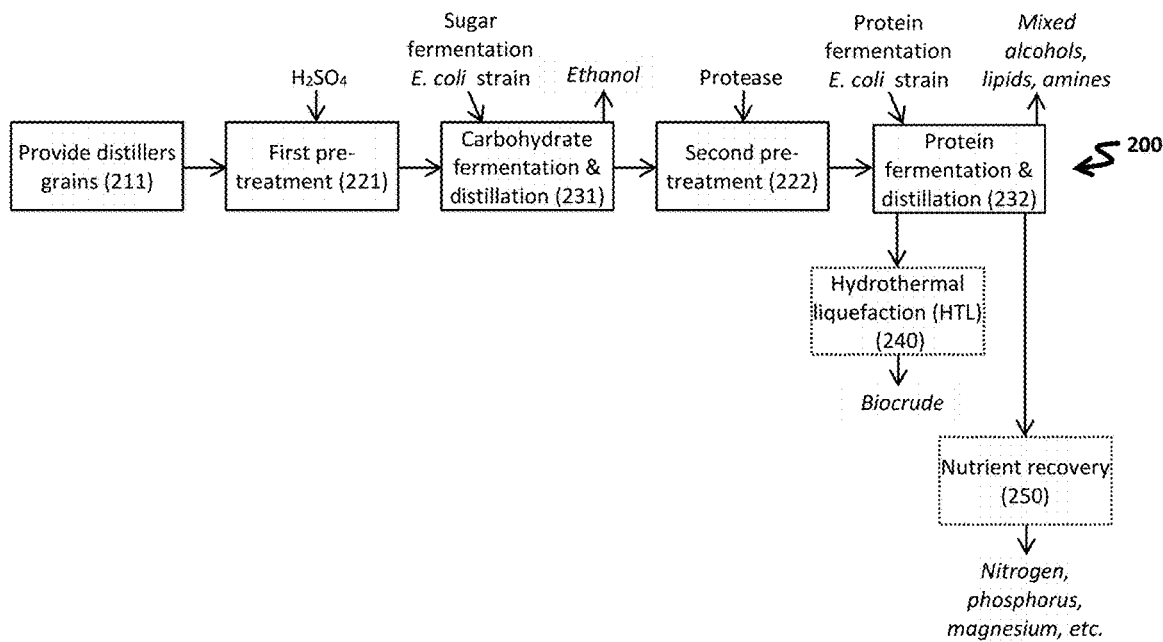
FIG. 2 shows another exemplary process flow diagram. Provided is an exemplary process 200 including inputs and outputs designated by arrows leading either into or away from a box, respectively.

Another exemplary conversion process 200 is shown in FIG. 2, which provides various inputs and outputs during the process. As can be seen, the process 200 includes a first step of providing 211 a biomass (e.g., distillers grain), which can then be pre-treated 221. This pre-treatment step 221 can include any useful input, e.g., water, one or more acids (e.g., dilute or strong $H_2SO_4$), a neutralizer (e.g., a base, such as NaOH), and/or one or more enzymes (e.g., a protease or a protease cocktail). The fermentation step 231 results in conversion of carbohydrates into one or more smaller or simpler components (e.g., alcohols) by employing an organism strain useful for sugar fermentation. A second pretreatment step 222 generally includes one or more enzymes, and a second fermentation step 232 results in conversion of proteins into one or more smaller or simpler components (e.g., alcohols, amino acids, ketoacids, and/or amines) by employing an organism strain useful for protein fermentation. Such smaller or simpler components can be further purified (e.g., extracted, distilled, precipitated, etc.) to provide pharmaceutical intermediates, chemicals, chemical/biochemical precursors, building blocks, reagents, and/or intermediates.

A distillation step (e.g., conducted after one fermentation step or after each fermentation step) can result in the separation of volatile fraction(s) from the less volatile fraction(s), resulting in, e.g., a fraction including one or more alcohols or mixtures thereof, and another fraction including a predominantly non-aqueous, lipid phase (e.g., a bioresidue). The fraction including alcohol(s) can be further purified to provide bioethanol.

Optionally, the bioresidue can be thermally treated at a temperature sufficient to separate volatile lipids from solid residuals, such as by way of hydrothermal liquefaction 240, to produce a liquefied mixture. This liquefied mixture can include biocrude oil, ash, biochar, and other components. The biocrude oil, in turn, can be further processed, e.g., by way of hydrotreatment with an input of hydrogen, to produce any useful biofuel, such as biodiesel, naphtha, or light hydrocarbons. Other components from the liquefied mixture can be phase separated to extract the solid residuals. This liquid phase can be further processed for nutrient and water recovery 250.

Any useful biomass can be employed. Exemplary biomass include distillers grains or co-products (e.g., wet distillers grains (WDGs), dried distillers grains (DDGs), dried distillers grains with solubles (DDGS), fatty acids from oil hydrolysis, lipids from evaporation of thin stillage, syrup, distillers grains, distillers grains with or without solubles, solids from a mash before fermentation, solids from a whole stillage after fermentation, biodiesel, and acyl glycerides), oilseed meals (e.g., soybean meal or canola meal), feeds (e.g., alfalfa meal, cottonseed meal, DDGS, rice bran, or wheat bran), yeast (e.g., extracts), algae (e.g., Nannochloropsis, wastewater algae, or any described herein), cereal by-products (e.g., whey), etc.

Pre-Treatment of the Biomass

Pre-treatment can be used to convert constituents within the biomass into various biocomponents (e.g., proteins, carbohydrates, fatty acids, and/or lipids). Such biocomponents can be pre-treated to obtain more solubilized or hydrolyzed constituents, such as amino acids or sugars (e.g., glucose). For instance, carbohydrates within the biomass can be pre-treated and, thereby, be converted into a sugar and/or an alcohol, such as glucose, fucose, galactose, xylose, mannose, mannitol, ethanol, butanol, and/or pentanol. In another instance, proteins within the biomass can be treated and, thereby, hydrolyzed and converted into amino acids. Such amino acids, in turn, can be fermented to produce one or more mixed alcohols and amines. In addition, one or more extraction techniques can be applied to separate the protein/carbohydrate fraction from other constituents. Such extraction techniques can include, e.g., use of one or more ionic liquids to selectively extract a particular fraction.

Pre-treatment can include the use of one or more acids, bases, oxidizers, reducers, and/or enzymes. Exemplary pre-treatment conditions include strong and/or dilute acid hydrolysis (e.g., with $H_2SO_4$ and/or HCl), base hydrolysis or neutralization (e.g., with NaOH), heat treatment, sonication, and/or enzyme degradation (e.g., with one or more proteases, such as endoproteases, exoproteases, serine proteases (e.g., subtilisin, also known as alcalase), aminopeptidases, carboxypeptidases, endoglucanases, cellobiohydrolases, glycoside hydrolases (e.g., lysozyme), endoglucanases, glucanases, endoxyalanases, pectinases, sulfatases (e.g., arylsulfatases), cellulases, xylanases, as well as mixtures thereof, such that available as commercially available Pronase®, a mixture of proteolytic enzymes that are produced in the culture supernatant of *Streptomyces griseus* K-1).

Fermentation

Fermentation conditions generally include the use of one or more organisms to convert starting reactants (e.g., biocomponents, such as carbohydrates, proteins, sugars, amino acids, etc.) into alcohol and other co-products. Fermentation can include degradation of carbohydrates into alcohol in the presence of one or more organisms. Such conditions can also release mixed alcohols and nitrogen from degradation of protein, which can contain up to about 90% of the nitrogen in a biomass. In this manner, fermentation provides useful biofuels and intermediates (e.g., alcohols). Furthermore, released nitrogen can be recovered and recycled.

For fermentation, any useful organisms can be employed, such as one or more bacteria (e.g., *Escherichia*, such as *E. coli*; *Zymobacter*, such as *Z. palmae*; or *Zymomonas*, such as *Z. mobilis*) and one or more yeast (e.g., *Saccharomyces*, such as *S. cerevisiae*), including mutant forms thereof, including those that deaminate protein hydrolysates (e.g., into ketoacids, tricarboxylic acid cycle intermediates, etc.), that convert proteins to alcohols (e.g., to C4 or C5 alcohols), and/or that lack one or more quorum-sensing genes (e.g., genes luxS or lsrA), such as those described in Atsumi S et al., "Non-fermentative pathways for synthesis of branched-chain higher alcohols as biofuels," Nature 2008; 451:86-90; and Huo Y X et al., "Conversion of proteins into biofuels by engineering nitrogen flux," Nat. Biotechnol. 2011; 29(4): 346-51, which is incorporated herein by reference in its entirety; yeast (e.g., Saccharomyces, such as S. cerevisiae and S. uvarum); and fungi (e.g., Aspergillus, such as A. niger, A. terreus, and A. fumigatus).

In one instance, fermentation is conducted in the presence of one or more organisms useful for sugar or carbohydrate fermentation. Such organisms can include those selected by directed evolution to employ any useful sugar substrate, to have enhanced alcohol tolerance, and/or to have increased activity. Exemplary organisms include E. coli KO11, E. coli LY01, E. coli SZ110, E. coli LY168, Z. mobilis mobilis AX101, S. cerevisiae 424A (LNH-ST), and S. cerevisiae ATCC 96581.

In another instance, fermentation is conducted in the presence of one or more organisms useful for protein fermentation. Such organism can include those selected by directed evolution to switch cofactor specificity, to deaminate protein hydrolysates, and/or to reduce competing pathways. Exemplary organisms include those having mutants forms of one or more enzymes, such as YqhD and/or IlvC mutants to switch cofactor specificity, transhydrogenase overexpression in E. coli PntAB, alcohol dehydrogenase mutants (e.g., mutants of AdhE, AdhP, EutG, YiaY, YqhD, and/or YjgB), and/or ketol-acid isomerase mutants (e.g., mutants of IlvC, IlvD, IlvH, and/or IlvA), as well as any described in Brinkmann-Chen S et al., "General approach to reversing ketol-acid reductoisomerase cofactor dependence from NADPH to NADH," Proc. Nat'l Acad. Sci. USA 2013; 110(27):10946-51; and Bastian S et al., "Engineered ketol-acid reductoisomerase and alcohol dehydrogenase enable anaerobic 2-methylpropan-1-ol production at theoretical yield in Escherichia coli," Metab. Eng. 2011; 13(3):345-52, each of which is incorporated herein by reference in its entirety.

Exemplary mutants include an YqhD mutant (e.g., a mutant having a polypeptide sequence with at least one amino acid substitution, as compared to wild-type YqhD (e.g., such as SEQ ID NO:1 in FIG. 10C). In one non-limiting example, the YqhD mutant has a polypeptide sequence of SEQ ID NO:2 (FIG. 10D), or a fragment thereof, in which Xaa at position 39 is Ile, Tyr, Val, Leu, Phe, or any other conservative amino acid substitution described herein. In another non-limiting example, the YqhD mutant has a polypeptide sequence of SEQ ID NO:3 (FIG. 10E), or a fragment thereof, in which Xaa at position 40 is Pro, Arg, His, Lys, Trp or any other conservative amino acid substitution described herein.

In yet another non-limiting example, the YqhD mutant has a polypeptide sequence of SEQ ID NO:4 (FIG. 10F), or a fragment thereof, in which Xaa at position 39 is Ile, Tyr, Val, Leu, Phe, or any other conservative amino acid substitution described herein; and in which Xaa at position 40 is Pro, Arg, His, Lys, Trp or any other conservative amino acid substitution described herein. In another embodiment, the mutant includes Ile at position 39 and Arg at position 40; Ile at position 39 and Lys at position 40; Ile at position 39 and His at position 40; Val at position 39 and Arg at position 40; Val at position 39 and Lys at position 40; Val at position 39 and His at position 40; Leu at position 39 and Arg at position 40; Leu at position 39 and Lys at position 40; Leu at position 39 and His at position 40; Tyr at position 39 and His at position 40; Phe at position 39 and His at position 40; Phe at position 39 and Lys at position 40; Phe at position 39 and Arg at position 40; Trp at position 39 and Arg at position 40; Trp at position 39 and Lys at position 40; Trp at position 39 and His at position 40; Ser at position 39 and His at position 40; or Ser at position 39 and Thr at position 40.

In another non-limiting example, the YqhD mutant has a polypeptide sequence of SEQ ID NO:5 (FIG. 10G), or a fragment thereof, in which one or more amino acid substitutions are present at positions 37, 38, 39, and/or 40. In one embodiment, the mutant includes one of the following amino acids, independently, at position 37, 38, and 39: Gly, Ile, Tyr, Val, Leu, Phe, or any other conservative amino acid substitution described herein. In another embodiment, the mutant includes one of the following amino acids at position 40: Ser, Pro, Arg, His, Lys, Trp, or any other conservative amino acid substitution described herein.

Other exemplary mutants include an IlvC mutant (e.g., a mutant having a polypeptide sequence with at least one amino acid substitution, as compared to wild-type IlvC (e.g., such as SEQ ID NO:6 in FIG. 11A). In one non-limiting embodiment, the IlvC mutant has a polypeptide sequence of SEQ ID NO:7 (FIG. 11B), or a fragment thereof, in which one or more amino acid substitutions are present at positions 71, 76, 78, 110, 146, 185, and/or 433.

The mutants can have any useful characteristic provided during selective evolution. In one non-limiting instance, the mutant can have increased reactivity with nicotinamide adenine dinucleotide (NADH), as compared to a wild-type reference protein. In another instance, the mutant can have increased reactivity NADH over nicotinamide adenine dinucleotide phosphate (NADPH), as compared to a wild-type reference protein. In yet another instance, the mutant can have increased specificity for NADH over NADPH, as compared to a wild-type reference protein.

Figure 3A:
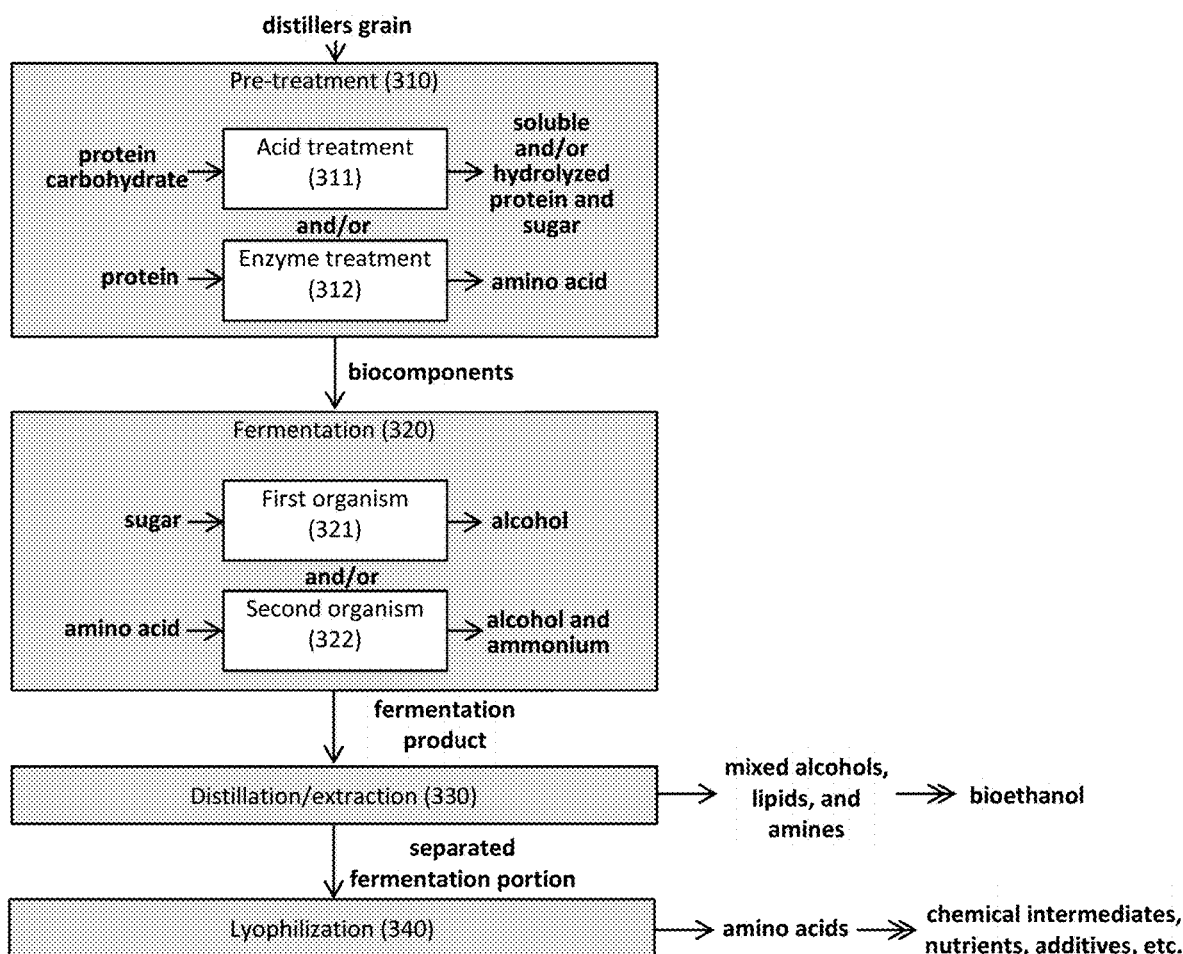
FIGS. 3A-3D shows exemplary processes with various sub-steps. Provided are (A) an exemplary process including sub-steps for the pre-treatment 310 and fermentation 320 steps; (B) an exemplary process including a distillation/extraction step 3005 between the pre-treatment 3003 and fermentation 3004 steps; (C) another exemplary process including a first pre-treatment step 3103 and a subsequent distillation/extraction step 3105 to separate a biomass solid (e.g., a bioresidue); and (D) yet another exemplary process including distillation/extraction steps 3505,3605 subsequent to each fermentation step 3504,3604.

FIG. 3A shows a portion of an exemplary process including a pre-treatment step 310, a fermentation step 320, a distillation/extraction step 330, and a lyophilization step 340. Each of these steps, in turn, can include one or more other sub-steps. For instance, pre-treatment 310 can include acid treatment 311 in order to degrade proteins and carbohydrates into soluble and/or hydrolyzed protein and sugar; as well as enzyme treatment 312 in order to degrade proteins into amino acids. Each of these components (e.g., proteins, carbohydrates, sugars, amino acids, etc.) obtained from the pre-treatment step is considered a biocomponent. In some instances, pre-treatment 310 results in solubilization of useful biocomponents, as well as separation of biomass solids.

Fermentation can include use of one or more organisms configured to facilitate degradation (e.g., specific or non-specific degradation) of one or more biocomponents. As can be seen, an exemplary fermentation step 320 includes use of at least two organisms, in which a first organism 321 is useful for degradation of sugar into alcohol and in which a second organism 322 is useful for degradation of amino acid into an alcohol (e.g., $R^4OH$, in which $R^4$ is an optionally substituted alkyl, such as an optionally substituted $C_{2-10}$ alkyl) and an amine (e.g., $N^+R^1R^2R^3R^4$ or $NR^1R^2R^3$, in which each of $R^2$, $R^3$, and $R^4$ is, independently, H or an optionally substituted alkyl). The fermentation step 320 results in a fermentation product, which can include a mixture of alcohols, amino acids, amines, and/or lipids.

Figure 8:
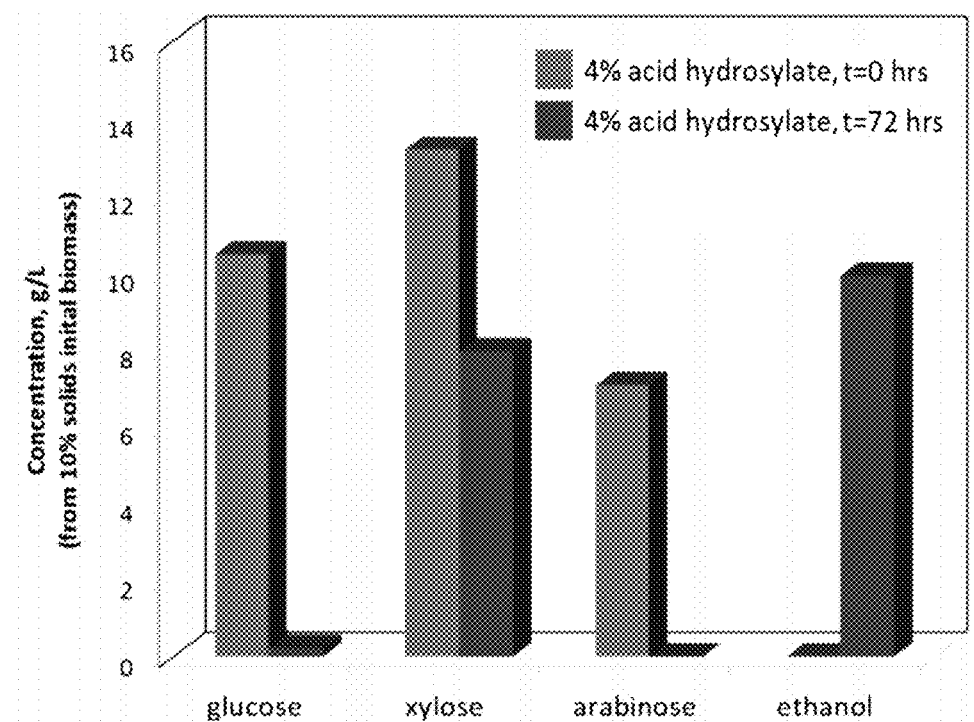
FIG. 8 shows carbohydrate hydrolysis and ethanol yields, in which the process included dilute acid pre-treatment and fermentation.
Figure 9:
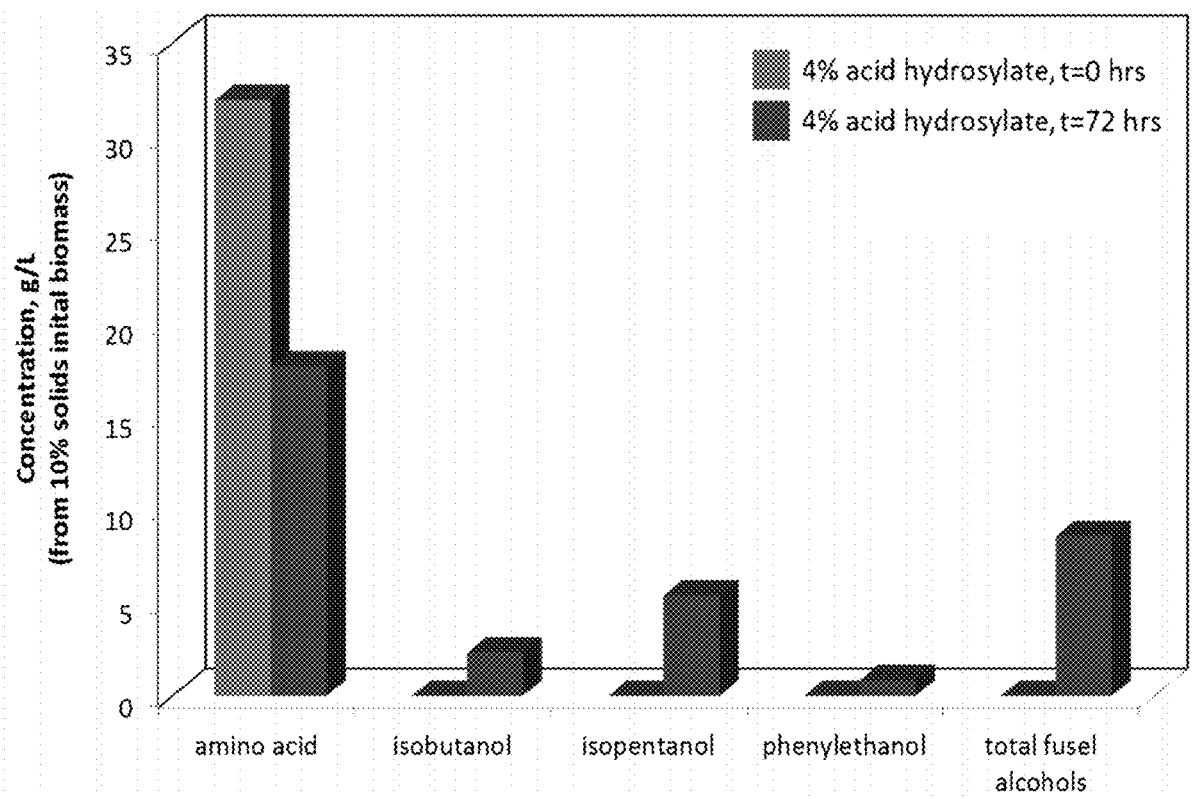
FIG. 9 shows protein hydrolysis and fusel alcohol yields, in which the process included dilute acid pre-treatment, enzymatic pre-treatment (e.g., protease digestion), and fermentation.

After distillation/extraction 330, various fractions of the mixture can be separated into different components, including a first fraction including mostly lipids and lipid products (e.g., a bioresidue); a second fraction including mixed alcohols and, optionally, neutral lipids; and a third fraction including amines and/or amino acids. The first fraction can be further processed (e.g., by way of liquefaction and/or pyrolysis) to produce a biocrude oil, which can be treated to form a biofuel. The second fraction can be further purified into, e.g., bioethanol. The third fraction can be further processed to isolate high-value amino acids. In some embodiments, the pre-treatment and fermentation conditions herein can provide enhanced alcohol yield (see, e.g., FIG. 8), as well as enhanced amino acid degradation and enhanced fusel alcohol yield (FIG. 9).

The pre-treatment, distillation/extraction, and fermentation steps can be conducted in any useful order. For instance, the fermentation step can be conducted prior to distillation/extraction, meaning that lipids, proteins, and carbohydrates, as well as derived components thereof, are present during fermentation.

Figure 3B:
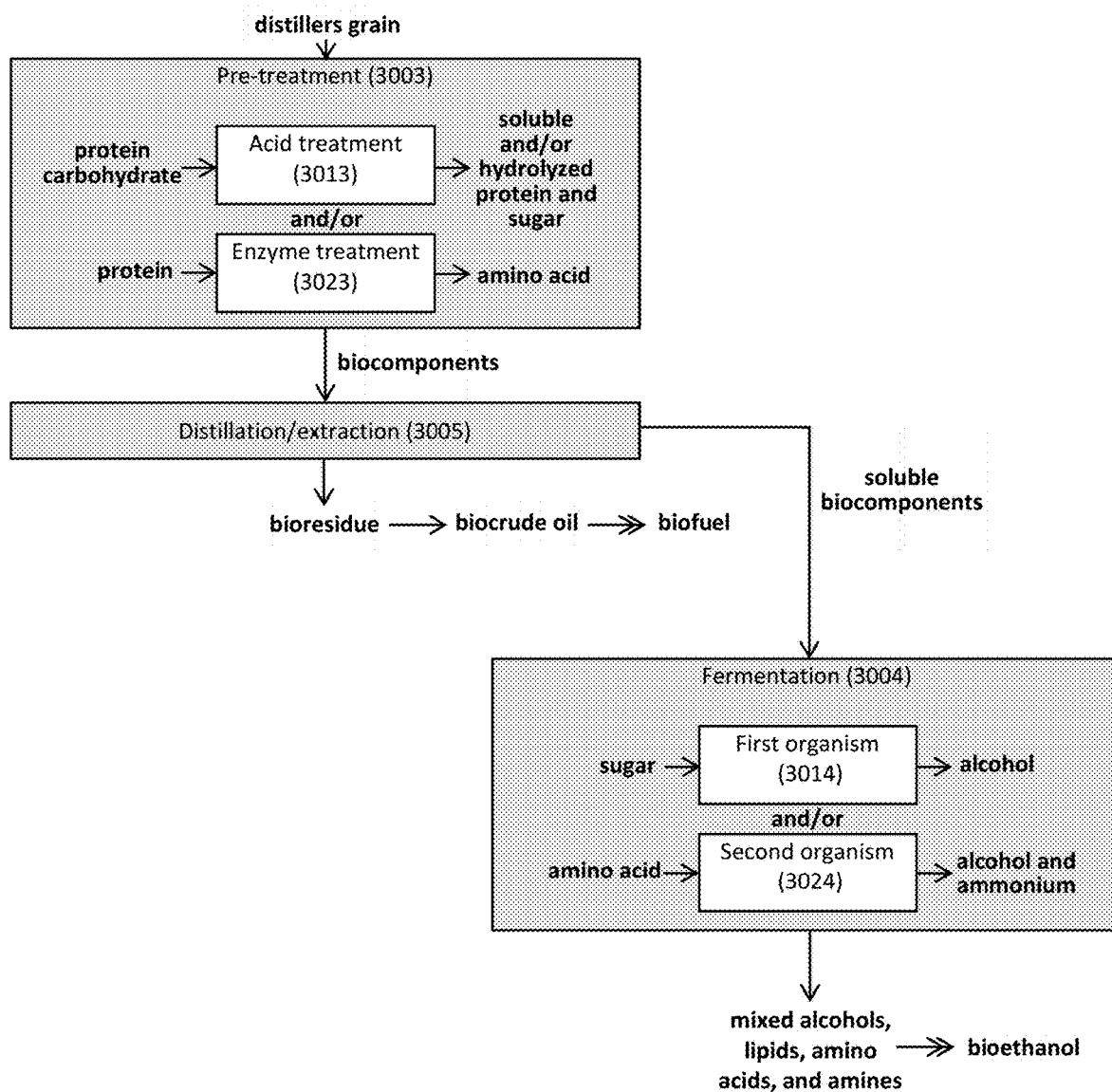

Alternatively, the distillation/extraction step can be conducted prior to fermentation, meaning that the lipid fraction will be omitted from the fermentation step. FIG. 3B shows a portion of an exemplary process including a pre-treatment step 3003, a distillation/extraction step 3005, and a fermentation step 3004. Pre-treatment 3003 can include the sub-steps of acid treatment 3013 in order to degrade proteins and carbohydrates into soluble and/or hydrolyzed protein and sugar; as well as enzyme treatment 3023 in order to degrade proteins into amino acids, thereby providing one or more biocomponents.

Next, a distillation/extraction 3005 step is conducted to provide a first fraction including mostly lipids and lipid products (e.g., a bioresidue) and a second fraction including soluble biocomponents. The first fraction can be further processed (e.g., by way of liquefaction and/or pyrolysis) to produce a biocrude oil, which can be treated to form a biofuel. The second fraction can be fermented and further purified into, e.g., bioethanol. As can be seen, an exemplary fermentation step 3004 includes use of at least two organisms, in which a first organism 3014 is useful for degradation of sugar into alcohol and in which a second organism 3024 is useful for degradation of amino acid into alcohol and an amine (e.g., including ammonium).

Figure 3C:
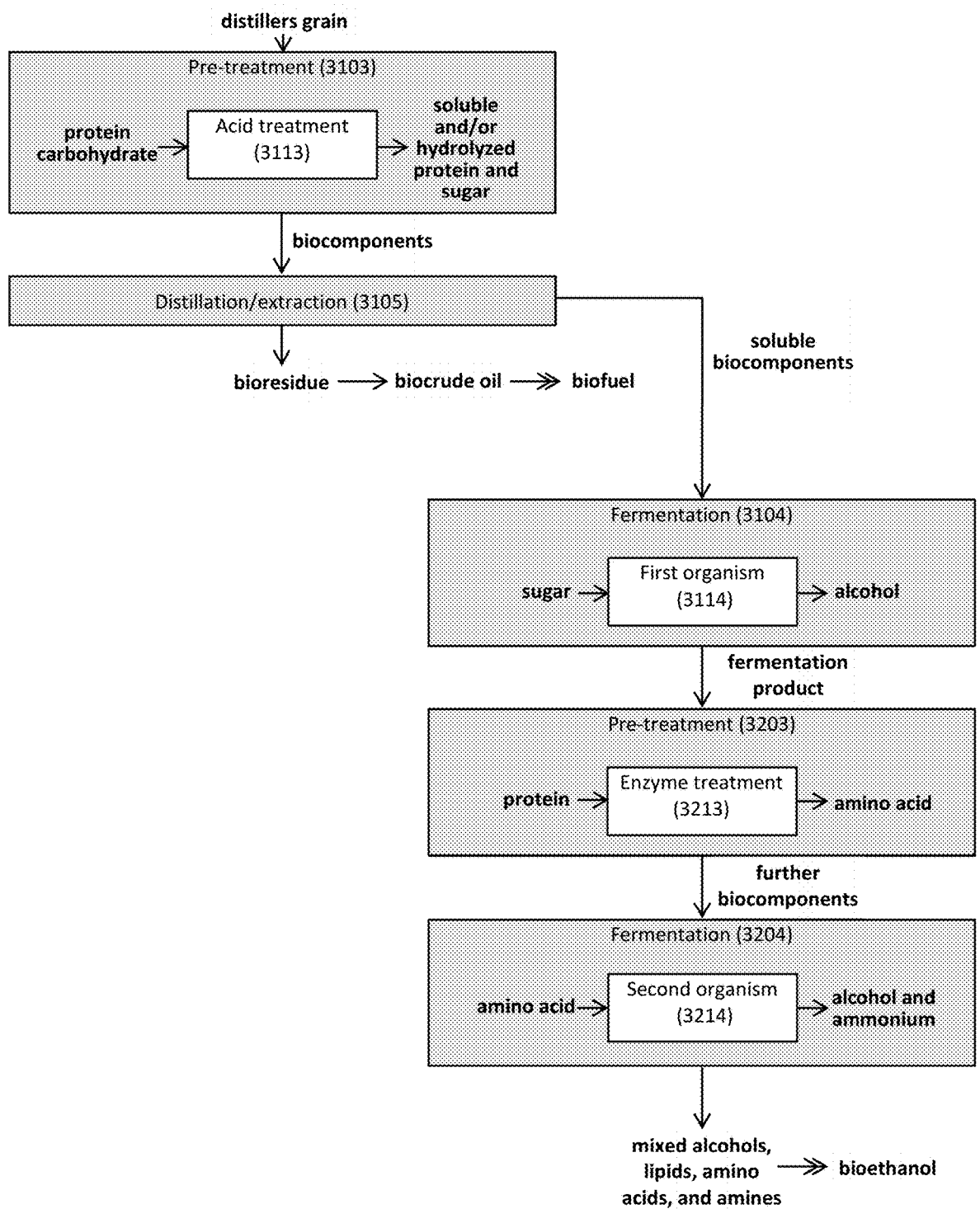

The process can include a pre-treatment step that precedes each fermentation step. FIG. 3C shows a portion of an exemplary process including a first pre-treatment step 3103, a distillation/extraction step 3105, and a first fermentation step 3104. Pre-treatment 3103 can include acid treatment 3113 in order to degrade proteins and carbohydrates into soluble and/or hydrolyzed protein and sugar, followed by fermentation 3104 with a first organism 3114 that is useful for degradation of sugar into alcohol.

The process can be followed by a second pre-treatment step 3203 and a second fermentation step 3214. Pre-treatment 3203 can include enzyme treatment 3213 in order to degrade proteins into amino acids, thereby providing one or more biocomponent, followed by fermentation 3204 with a second organism 3214 that is useful for degradation of amino acid into alcohol and an amine (e.g., an ammonium).

Figure 3D:
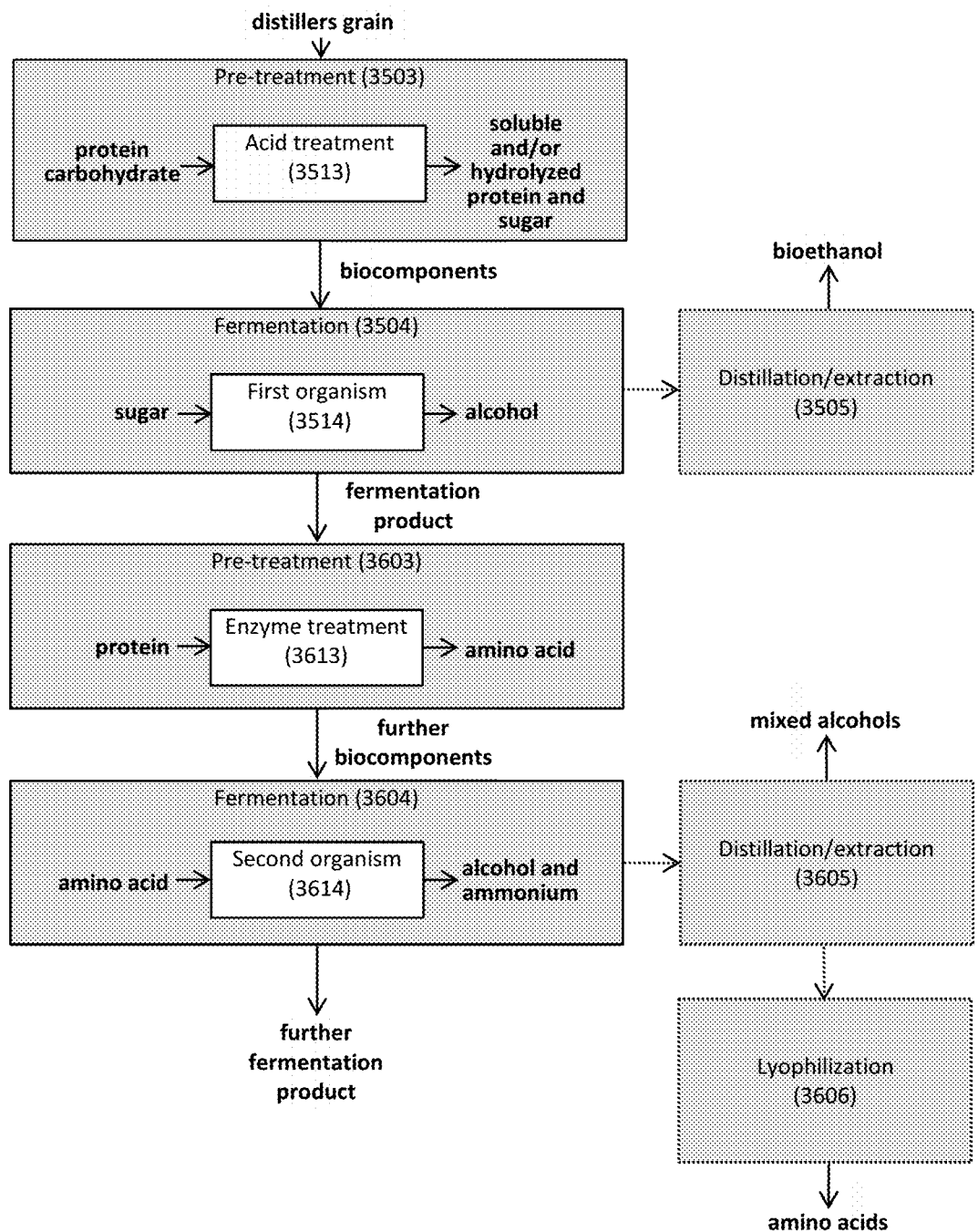

Distillation/extraction steps can be conducted at any useful time during the process. FIG. 3D shows a portion of an exemplary process including a first pre-treatment step 3503, a first fermentation step 3504, a second pre-treatment step 3603, and a second fermentation step 3604.

Pre-treatment steps 3503,3603 can include acid treatment 3513 in order to degrade proteins and carbohydrates into soluble and/or hydrolyzed protein and sugar; or enzyme treatment 3613 in order to degrade proteins into amino acids. Fermentation steps 3504,3604 can include use of a first organism 3514 that is useful for degradation of sugar into alcohol and a second organism 3614 that is useful for degradation of amino acid into alcohol and an amine (e.g., an ammonium). Optionally, a first distillation/extraction step 3505 can be conducted after the first fermentation step 3504, thereby isolating bioethanol and removing this potentially inhibitory product from the fermentation product. In another example, a second distillation/extraction step 3605 can be conducted after the second fermentation step 3604, thereby isolating mixed alcohols from the fermentation product. In yet another example, a further separation step (e.g., a lyophilization step 3606) can be employed to isolate amino acids from the fermentation product.

Distillation/Extraction

The alcohol fermentation products, lipids, and amino acids from the biomass can be captured by distillation and solvent co-extraction. Retaining the lipids through the protein fermentation has been demonstrated to increase yield by reducing product inhibition by phase segregation into lipid microparticles, which can be extracted by lipophilic solvents, such as hexane and ethyl acetate, avoiding high energy fractional distillation of the more than $C_2$ alcohol (e.g., $C_{2-10}$ alcohol) and lipid products.

Any useful distillation and extraction techniques can be employed, including flash extraction, ionic liquid extraction, etc., to isolate one or more biocrude oil, aqueous phases, aqueous co-products, nutrients, etc.

Thermal Conversion, Liquefaction or Pyrolysis

High-temperature treatment (e.g., liquefaction or pyrolysis) can be used to separate or convert particular components of the biomass solids, bioresidue, etc. Exemplary thermal conversion conditions include use of catalysts, use of hydrogen (e.g., in hydrotreatment), use of water (e.g., in liquefaction, including sub-critical or super-critical water), use of aerobic conditions, use of anaerobic conditions (e.g., in pyrolysis), use of high pressure (e.g., of from about 2,000 psi to about 3,000 psi), and/or use of high temperatures (e.g., of from about 200° C. to about 800° C.) to decompose the bioresidue into small molecules, which in turn can react and repolymerize to form oily compounds within a biocrude oil.

In one instance, the thermal conversion condition includes liquefaction, which is generally conducted in the presence of water. By using high temperature and/or high pressure conditions, water becomes a reactive compound that converts the bioresidue into a biocrude oil. Exemplary liquefaction conditions include a wet biomass (e.g., more about 70% moisture), a temperature of from about 200° C. to about 500° C., and a pressure of from about 4 to about 25 MPa.

In another instance, the thermal conversion condition includes pyrolysis, which is generally conducted in the absence of water and in anaerobic conditions. Exemplary pyrolysis conditions include a dry biomass (e.g., less than about 5% moisture), a temperature of from about 200° C. to about 750° C., and a pressure of from about 0.1 to about 0.5 MPa.

Exemplary thermal conversion conditions are described in Ma F et al., "Biodiesel production: a review," *Bioresourc. Technol.* 1999; 70:1-15; Naik S N et al., "Production of first and second generation biofuels: a comprehensive review," *Renew. Sustain. Energy Rev.* 2010; 14:578-97; Raheem A et al., "Thermochemical conversion of microalgal biomass for biofuel production," *Renew. Sustain. Energy Rev.* 2015;

49:990-9; Ringer M et al., "Large-scale pyrolysis oil production: a technology assessment and economic analysis," *National Renewable Energy Laboratory Technical Report NREL/TP*-510-37779, November 2006, 93 pp.; and Schneider R C S et al., "Potential production of biofuel from microalgae biomass produced in wastewater," in *Biodiesel—Feedstocks, Production and Applications*, Prof. Zhen Fang (ed.), InTech, 2012, 22 pp., each of which is incorporated herein by reference in its entirety.

Any of the liquefaction steps herein can be replaced by any other thermal conversion step (e.g., pyrolysis) in which high temperature conditions are employed to thermally degrade a bioresidue.

Hydrotreatment

Hydrotreatment is generally used to convert compositions into useful intermediate products or end-use products. Such hydrotreatment generally includes use of high temperatures to institute any useful chemical change, e.g., to break apart triglycerides; to form low molecular weight carbon species, such as optionally substituted alkanes, cycloalkanes, or aryls; to saturate carbon chains with hydrogen; to denitrogenate species; and/or to deoxygenate species to form alkanes, such as n-alkanes. For instance, hydrotreatment can be used to upgrade biocrude oil into biofuels, biochar, or ash; as well as to convert aqueous co-products into biogas. Biocrude oil produced from the post-fermentation residuals by HTL is indicated to have ~50% reduction in nitrogen (primary and secondary amines), thus making it acceptable for hydrotreatment using the existing petrochemical infrastructure.

Hydrotreatment can include isomerization, hydrocracking, distillation, hydrodeoxygenation, catalytic processing (e.g., such as use of one or more catalysts to remove nitrogen, oxygen, and/or sulfur from the biocrude oil under any useful condition, such as a pressure of from about 5 MPa to about 15 MPa and a temperature of from about 200° C. to about 450° C.), liquefaction (e.g., such as hydrothermal liquefaction (HTL) or catalytic liquefaction of a biocrude oil into a biofuel or a biofuel intermediate by use of an operating temperature of from about 100° C. to about 500° C.), transesterification (e.g., treatment of biocrude oil with an alcohol and an optional catalyst to produce methyl ester biodiesel), and/or catalytic hydrothermal gasification (CHG) (e.g., of an aqueous co-product into biogas).

The hydrotreatment process can employ any useful catalyst (e.g., a metal catalyst, such a copper-based catalyst (e.g., CuCr, CuO), a nickel-based catalyst (e.g., NiMo), a ruthenium-based catalyst, a palladium-based catalyst (e.g., Pd/C), a platinum-based catalyst, a rhenium-based catalyst, or a cobalt-based catalyst (e.g., CoMo)) in the presence of any carrier (e.g., a zeolite, an alumina, etc.); any useful reagent, such as hydrogen (e.g., $H_2$) or water (e.g., supercritical water); any useful pressure, e.g., such as from about 3 MPa to about 30 MPa (e.g., from about 5 MPa to about 20 MPa); and/or any useful temperature, e.g., such as from about 100° C. to about 500° C. (e.g., from about 250° C. to about 350° C.). Further exemplary hydrotreatment conditions are described in Ma F et al., "Biodiesel production: a review," *Bioresourc. Technol.* 1999; 70:1-15; Tran N H et al., "Catalytic upgrading of biorefinery oil from micro-algae," *Fuels* 2010; 89:265-74; and Wildschut J et al., "Catalyst studies on the hydrotreatment of fast pyrolysis oil," *Appl. Catalysis B* 2010; 99:298-306, each of which is incorporated herein by reference in its entirety.

Exemplary biofuels formed by hydrotreatment include naphtha, biodiesel (e.g., including one or more unsaturated fatty acids or fatty acid esters, such as of from about 10% to about 35% of a long chain fatty acid having a $C_{13}$-$C_{21}$ tail, such as a palmitic fatty acid ($C_{16}$ tail), linoleic fatty acid ($C_{18}$ tail), oleic fatty acid ($C_{18}$ tail), and/or stearic fatty acid ($C_{18}$ tail)), green diesel, renewable aviation fuel, hydrocarbons (e.g., light hydrocarbons), alcohol (e.g., ethanol; propanol, such as 1-propanol; butanol, such as n-butanol, isobutanol, 2-butanol, 3-butanol, 2-methyl-1-butanol, 3-methyl-1-butanol, etc.), and/or a biogas (e.g., hydrogen or methane). Other products formed by hydrotreatment include solid residuals (e.g., biochar and ash), aqueous co-products (e.g., ketoacids, amines, nutrients, etc.), as well as other useful co-products (e.g., animal feed, fertilizer, glycerine, biopolymers, etc.).

Phase Separation

Phase separation steps can be employed to separate components of a liquefied mixture, fermentation broth, aqueous fraction, a non-aqueous fraction, alcohol fraction, etc. Such steps include any that separate liquid from solid phases, as well as separate two or more phases that can be differentiated based on solubility, miscibility, etc. (e.g., as those present in non-aqueous phases, aqueous phases, lipophilic phases, etc.) in any useful solvent (e.g., an organic solvent, an aqueous solvent, water, buffer, etc.). Phase separation techniques include flash separation (e.g., separation of liquefied mixture into biocrude oil, solid residuals, aqueous phase, and/or aqueous co-products), acid absorption (e.g., absorption of acid in a matrix to provide recovered nutrients and water for recycled use), filtration, distillation, solvent extraction, ion liquid extraction, etc. The resultant products and co-products can include one or more intermediate products that can optionally be processed to form useful end-use products.

EXAMPLES

Example 1: Biochemical Upgrading of Dried Distillers Grains

Dried distillers grains are a high-protein biomass that is recalcitrant to further processing. The methods described herein provide a process to upgrade this biomass into useful intermediates and by-products. In one embodiment, the method includes an integrated sugar and protein fermentation process, with pre-treatment steps to facilitate fermentation. The method can include use of a dilute acid (e.g., use of 2-10% $H_2SO_4$ at a temperature of from about 90° C. to 145° C. for any useful incubation period, such as about 30 minutes to 6 hours) prior to use of a sugar fermentation strain (e.g., *E. coli* K011) to convert sugars into ethanol. The method can also include use of an enzyme (e.g., about 0.5 g/L to 2 g/L of a protease or protease cocktail at a temperature of from about 37° C. to 55° C. for any useful incubation period, such as from about 12 to 48 hours) prior to use of a protein fermentation strain (e.g., *E. coli* YH83 with one or more additional mutated variations) to convert amino acids to alcohols (e.g., more than $C_2$ alcohols, such as $C_{3-10}$ alcohols) and amines (e.g., $NH_4$).

Figure 4A:
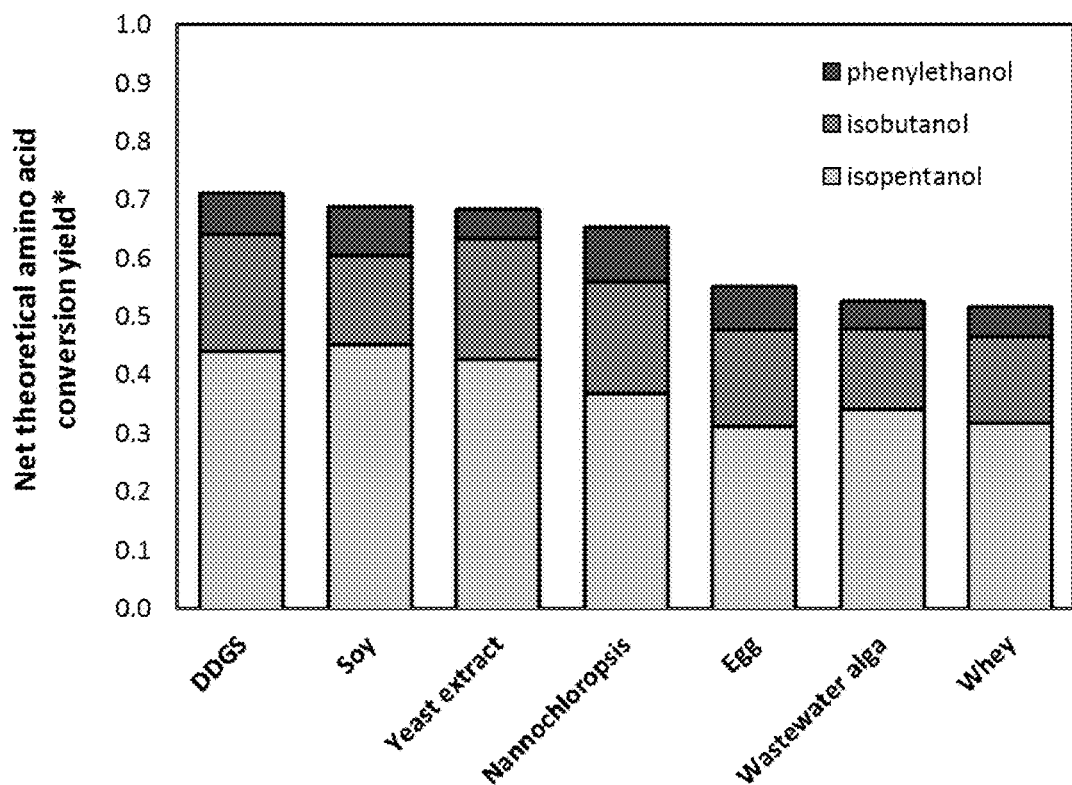
FIGS. 4A-4B shows comparative technoeconomic potential of various high-protein feedstocks, including dried distillers grains with solubles (DDGS). Provided are (A) a comparison of net theoretical amino acid yields for various biomass and (B) a comparison of unutilized high value amino acids for various biomass. The asterisk in (A) indicates that remineralized ammonia (as $NH_4MgPO_4$) was included in the mass balance.
Figure 4B:
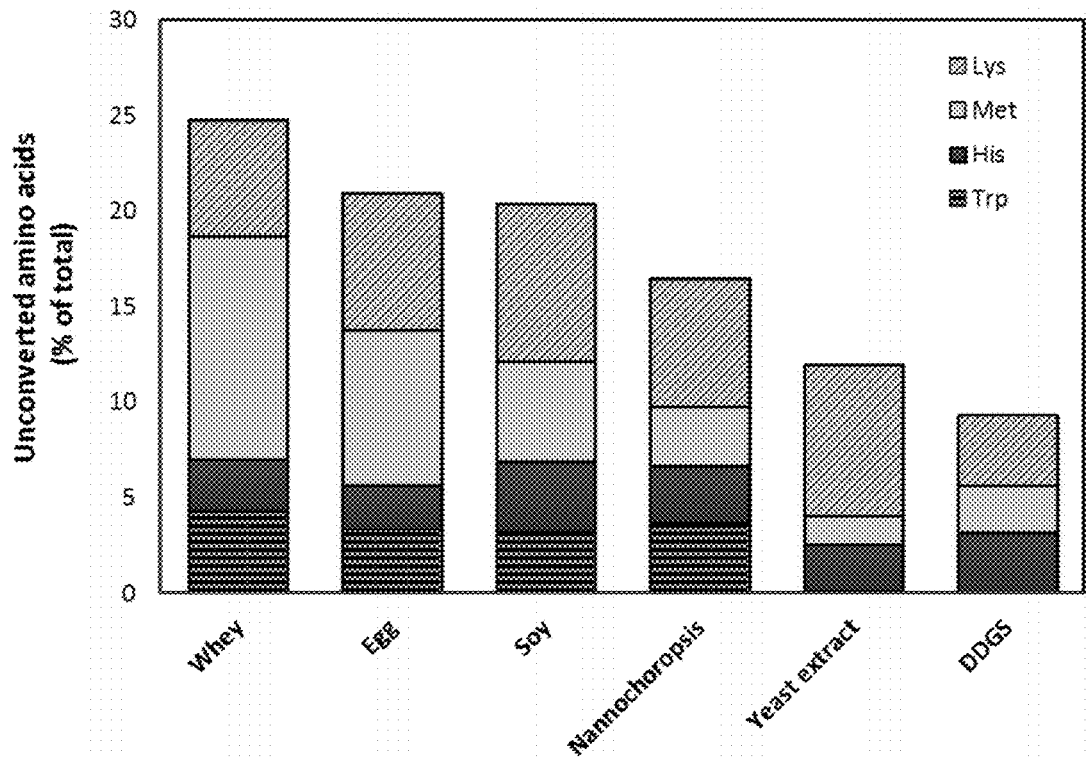

Any useful biomass can be processed. In particular, high-protein biomass can be particularly beneficial. Exemplary biomass include dried distillers grains with solubles (DDGS), soy products (e.g., soy meal), yeast products (e.g., yeast extract), whey, algae (e.g., microalgae, macroalgae, diatoms, green algae, yellow algae, phytoplankton, plankton, protists, haptophytes, chlorophyta, and/or cyanobacteria), etc. FIGS. 4A-4B provides the potential conversion yield of various biomass, as well as the potential yield of unutilized high value amino acids. As an initial step, processing methods in this Example were employed with DDGS samples.

Figure 5:
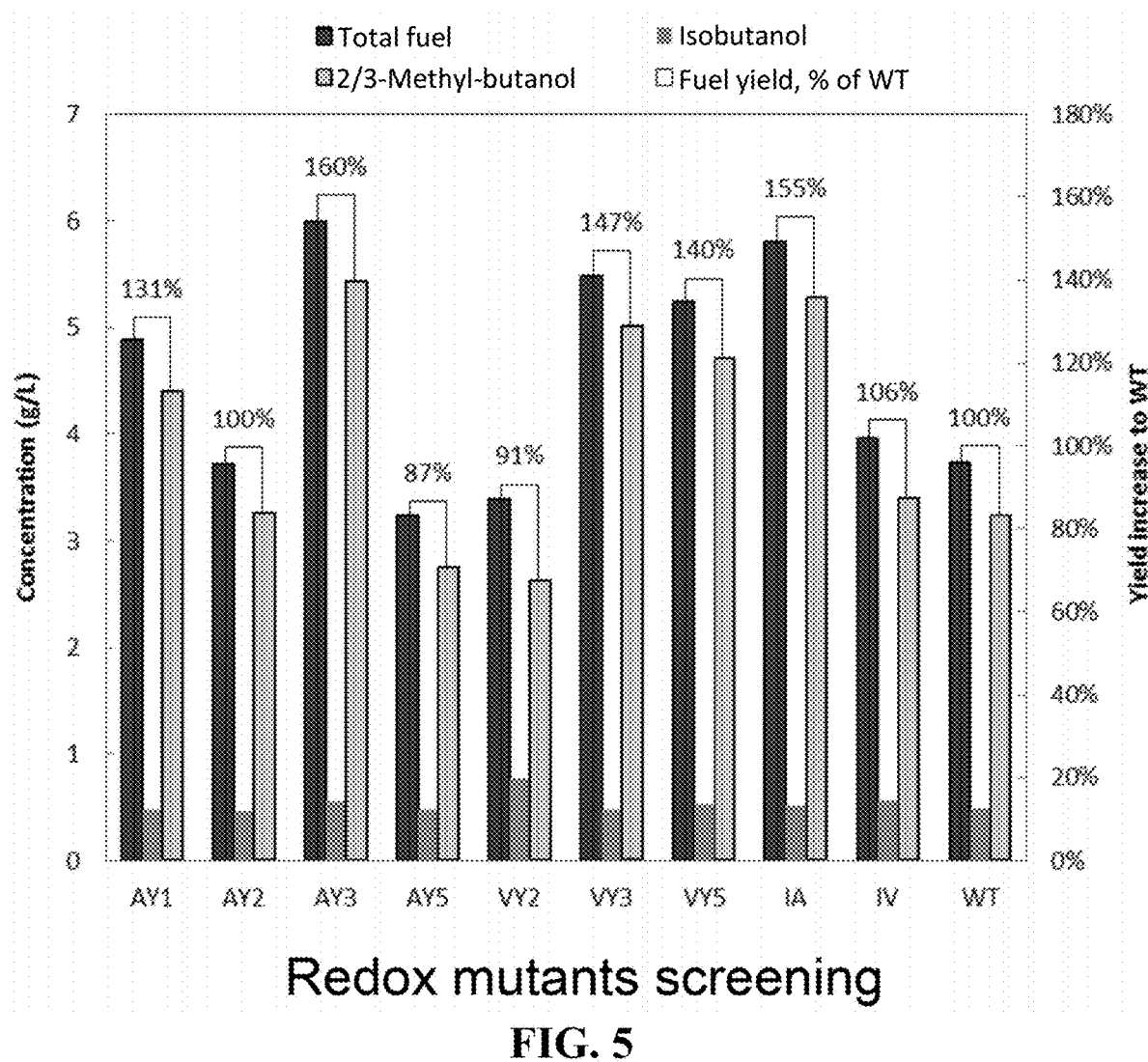
FIG. 5 shows the effect of redox cofactor engineering to produce various genetically engineered organism strains. Provided is a graph showing the concentration of fusel butanol produced by various redox mutant strains in the presence of an amino acid mixture. Redox mutant strains include AY1, AY2, AY3, AY5, VY2, VY3, VY5, IA, and IV, as described herein, which were compared to the wild-type (WT) strain.

Fermentation strains were developed and identified. As seen in FIG. 5, genetic engineering of *E. coli* resulted in organisms with high activity under anaerobic or microaerobic conditions. Our approach focused on, in part, altering the cofactor specificity of two enzymes in the pathway that provides isobutanol. In particular, two enzymes in the keto-acid pathway were modified: ketol-acid reductoisomerase IlvC and alcohol dehydrogenase YqhD. Generally, the wild-type strain employs a NADPH cofactor having a 2'-phosphate group. Modifications for the mutants were optimized to provide increased activity in the presence of a non-native NADH cofactor, as compared to the wild-type strain.

Mutant strains included AY1 (replacing IlvC with mutant A combined with replacing YqhD with mutant Y1), AY2 (replacing IlvC with mutant A combined with replacing YqhD with mutant Y2), AY3 (replacing IlvC with mutant A combined with replacing YqhD with mutant Y3), AY5 (replacing IlvC with mutant A combined with replacing YqhD with mutant Y5), VY2 (replacing IlvC with mutant V combined with replacing YqhD with mutant Y2), VY3 (replacing IlvC with mutant V combined with replacing YqhD with mutant Y3), VY5 (replacing IlvC with mutant V combined with replacing YqhD with mutant Y5), IA (replacing IlvC with mutant A), and IV (replacing IlvC with mutant V). Additional details for these mutant strains are described herein. In particular, five new *E. coli* strains showed increased conversion yield, as compared to the wild-type YH83 strain.

Figure 6:
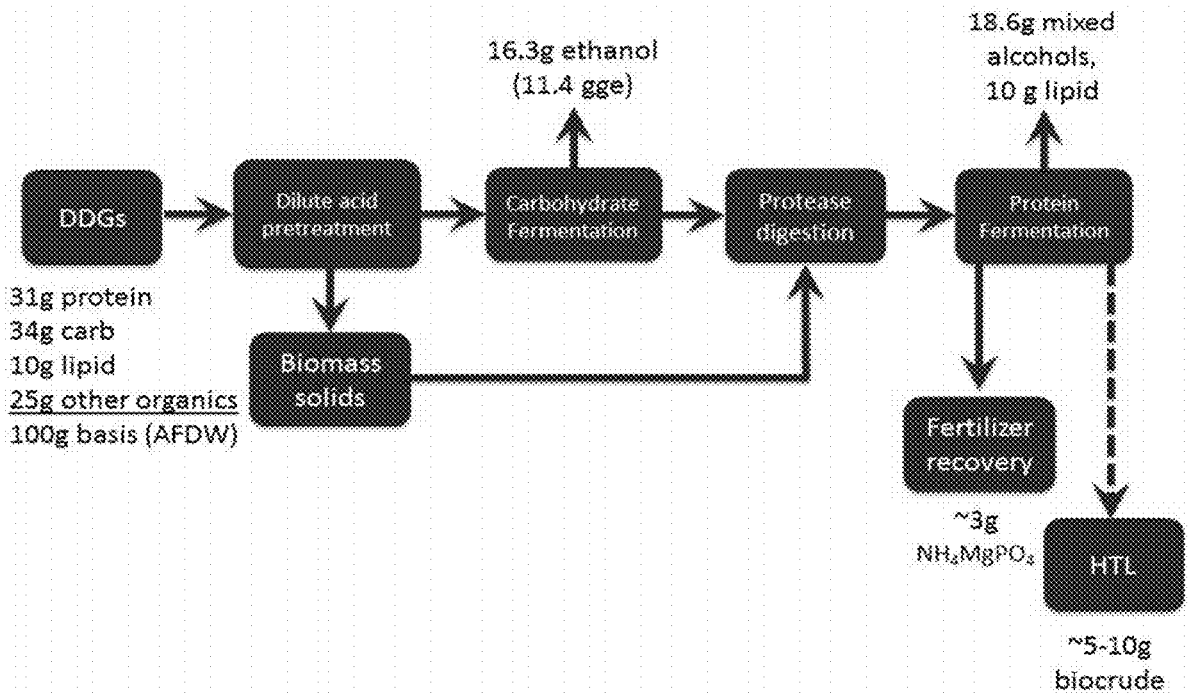
FIG. 6 shows an exemplary process flow diagram for upgrading biomass, such as DDGs.
Figure 7:
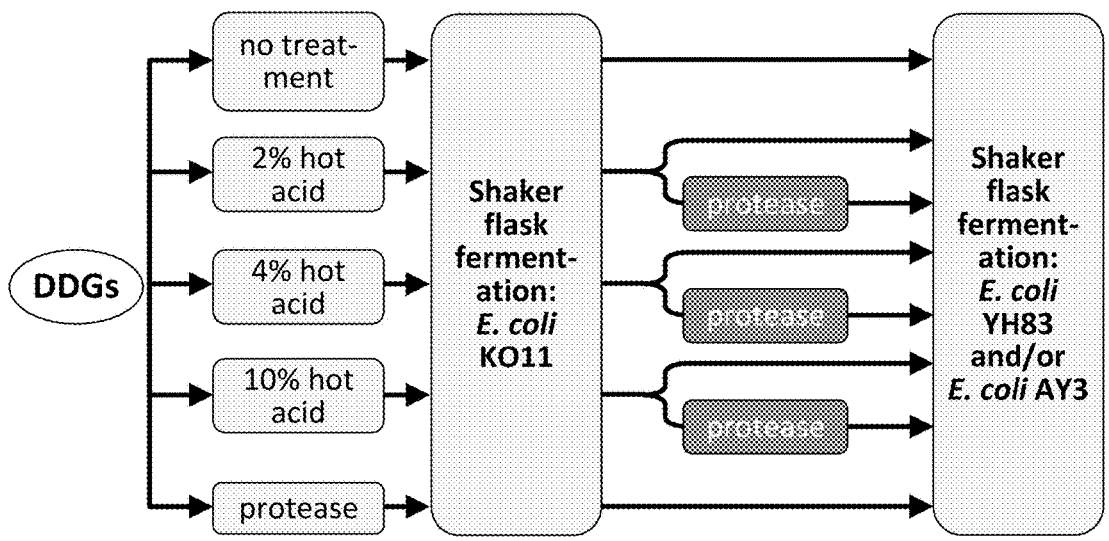
FIG. 7 shows another exemplary process flow diagram for further optimization.

FIG. 6 shows an exemplary process flow for use with modified fermentation stains. This exemplary process can be optimized by varying the dilute acid pre-treatment conditions, by employing enzymatic pre-treatment at particular points of the process, and by separating the two fermentation steps, in which each step uses a different strain (see, e.g., FIG. 7).

Dilute acid pre-treatment and fermentation achieved enhanced bioconversion of carbohydrates (e.g., sugars) into ethanol. As seen in FIG. 8, dilute acid hydrolysis pre-treatment resulted in more than 90% hydrolysis of various carbohydrates, including glucose, xylose, and arabinose. After treatment with 4% hot acid for 72 hours, the concentrations of these three representative sugars were decreased, and the concentration of ethanol increased at a theoretical conversion yield of about 60.7%. Improved xylose degradation can be promoted in any useful manner, e.g., by increasing the incubation temperature, increasing the concentration of the acid during pre-treatment, including a pre-treatment step with basic conditions (e.g., in the presence of NaOH or KOH), and/or by including one or more enzymes to cleave xylose, such as an isomerase, a reductase, etc.

Enzymatic pre-treatment and fermentation achieved enhanced bioconversion of proteins into fusel alcohol (e.g., more than $C_2$ alcohols, such as isobutanol, isopentanol, and/or phenylethanol) and amines. Enzymatic pre-treatment combined with dilute acid pre-treatment resulted in more than 90% hydrolysis of various carbohydrates. Furthermore, as seen in FIG. 9, after treatment for 72 hours, the concentration of amino acids was decreased, and the concentration of various fusel alcohols increased at a theoretical conversion yield of about 40.8%. Improved resistance to product inhibition can be promoted in any useful manner, e.g., by employing one or more separation or extraction steps; or by employing one or more lipids to promote vesicle formation.

Example 2: Cofactor Engineering to Improve the Fusel Alcohol Yield

Algal protein, as well as other high-protein feedstock, can be feasibly converted into fusel butanol with an engineered *E. coli* strain. In particular, algal protein has been used for producing fuel compounds, but the titer of fusel butanol is generally relatively low. One possible reason is cofactor imbalance during the algal protein fermentation.

To resolve this problem, a direct evolution approach was applied to switch the cofactor specificity of two enzymes (IlvC and YqhD) in the isobutanol pathway. These two enzymes rely on native cofactor NADPH in this pathway. Cofactor switching can allow for reactivity in the presence of a non-native cofactor (NADH), even if the native cofactor (NADPH) is lacking (e.g., such as in microaerobic or anaerobic conditions). Through high throughput screening, more than 20 YqhD mutants showed the activity with NADH.

Five YqhD mutants were selected and then combined with one of two IlvC mutants to reengineer the production strain. Upon combining the beneficial mutations of IlvC and YqhD, the engineered *E. coli* strain AY3 provided an optimized performance, in which fusel butanol yield increased by about 60%, as compared to wild-type *E. coli*, under anaerobic fermentation with an amino acid mixture. When applied to algal protein hydrolysates, the engineered AY3 strain produced from about 38% to 100% more fusel butanol in the fermentation broth, as compared to wild-type. This study provides a promising approach to improve bioconversion of algal protein into fusel butanol (e.g., as advanced fuel compounds) and amino acids (e.g., for further processing as nutrients or chemical intermediates). Additional details for this study are provided in Example 3. The following materials and methods were employed for this study.

Strains and plasmids: The mutant *E. coli* strain YH83 (BW25113/F' [traD36, proAB+, lacI$^q$ ZAM15] ΔglnAΔgdhAΔluxSΔlsrA) containing plasmids pYX68, pYX90, and pYX97 was generously provided by Professor James C Liao from University of California, Los Angeles (UCLA) (see, e.g., Huo Y X et al., *Nat. Biotechnol.* 2011; 29(4):346-51). The strain was engineered for bioconversion of protein hydrolysates into isobutanol. Plasmids pYX90 and pYX97 contained IlvC and YqhD, which use NADPH as the cofactor. Plasmid pBbE1a and the *E. coli* strain DH1 were used for the expression and screening of mutant libraries of enzyme YqhD, as well as for the creation of IlvC mutants.

Selection of cofactor binding sites: The amino acids for mutation in YqhD were selected by inspecting the cofactor NADPH binding site. Autodock 4 was used to investigate the cofactor-enzyme interaction. The protein X-ray structure of *E. coli* K-12 YqhD (Entry No. 1OJ7) containing cofactor NADPH was extracted from RCSB Protein Data Bank.

Mutant library construction, expression, and high-throughput screening: Plasmid pBbE1a was generously provided by Dr. Taek Soon Lee from Joint BioEnergy Institute. Genes IlvC and YqhD were amplified from plasmids (pYX90 and pYX97), and then sub-cloned into vector pBbE1a under restriction cutting sites (EcoRI and BamHI) to achieve vectors pBbE1a-IlvC and pBbE1a-YqhD, respectively. Saturation mutagenesis was applied to create a recombinant mutant library of enzyme YqhD, following the description in the previous study (see, e.g., Wu W et al., "Site-saturation mutagenesis of formate dehydrogenase from *Candida bodinii* creating effective NADP$^+$-dependent FDH enzymes," *J. Molec. Catal. B* 2009; 61(3-4):157-61).

For the recombinant library of YqhD, primers with degenerate codons were used to create mutations at the selected amino acid sites. High fidelity DNA polymerase fusion Q5 (New England BioLabs, Inc. (NEB), Ipswich, Mass.) was used to generate the library and to express library members in *E. coli* DH1. Strains containing YqhD mutants were diluted properly and spread onto Luria-Bertani (LB) plates supplemented with ampicillin (100 µg/mL) for the following library screening.

According to the previous study (see, e.g., Bastian S et al., *Metab. Eng.* 2011; 13(3):345-52), the two mutant IlvCs (A71S, R76D, S78D Q110V/Q110A) switched the cofactor specificity from NADPH to NADH with the relatively high activity with NADH. Site mutagenesis (point mutation) was used to create two mutants of enzyme IlvC at the four target amino sites mentioned above. An iterative strategy was used to create all four sites of mutations. High fidelity DNA polymerase fusion Q5 was again used to create point mutations of IlvC in the vector pBbE1a-IlvC, as described before (see, e.g., Wu W et al., *J. Molec. Catal. B* 2009; 61(3-4): 157-61). Mutations were confirmed through DNA sequencing. All the primers used herein are listed in Table 1, below.

TABLE 1

Primers and mutants for YqhD and IlvC

| Name | Sequence | SEQ ID NO: | Notes |
|---|---|---|---|
| YqhD-pBbE1a-F | 5-CTC AGC GAA TTC ATG AAC AAC TTT AAT CTG CAC ACC CCA AC-3 | 10 | Clone YqhD into pBbE1a |
| YqhD-pBbE1a-R | 5-TGACCTGGATCCTTA GCG GGC GGC TTC GTA TAT AC-3 | 11 | |
| IlvC-pBbE1a-F | 5-CTC AGC GAA TTC ATG GCT AAC TAC TTC AAT ACA CTG AAT CTG C-3 | 12 | Clone IlvC into pBbE1a |
| IlvC-pBbE1a-R | 5-TGACCTGGATCC TTA ACC CGC AAC AGC AAT ACG TTT C-3 | 13 | |
| YqhD-S40-F | 5-GTATTGATTACCTACGGCGGC GGC <u>NNN</u> GTG AAA AAA ACC GGC GTT CTC-3 | 14 | Create mutant library S40 |
| YqhdS40-R | 5-GAG AAC GCC GGT TTT TTT CAC <u>NNN</u> GCC GCC GCC GTA GGT AAT CAA TAC-3 | 15 | |
| YqhD-G39S40-F | 5-GTATTGATTACCTACGGCGGC <u>NNN NNN</u> GTG AAA AAA ACC GGC GTT CTC-3 | 16 | Create mutant library G39S40 |
| Yqhd-G39S40-R | 5-GAG AAC GCC GGT TTT TTT CAC <u>NNN NNN</u> GCC GCC GTA GGT AAT CAA TAC-3 | 17 | |
| YqhD-S40P-F | 5-GTATTGATTACCTACGGCGGC <u>CCG</u> GTG AAA AAA ACC GGC GTT CTC-3 | 18 | Mutant Y1 (S40P) |
| Yqhd-S40P-R | 5-GAG AAC GCC GGT TTT TTT CAC <u>CGG</u> GCC GCC GTA GGT AAT CAA TAC-3 | 19 | |
| YqhD-S40R-F | 5-GTATTGATTACCTACGGCGGC <u>CGT</u> GTG AAA AAA ACC GGC GTT CTC-3 | 20 | Mutant Y2 (S40P) |
| Yqhd-S40R-R | 5-GAG AAC GCC GGT TTT TTT CAC <u>CGT</u> GCC GCC GTA GGT AAT CAA TAC-3 | 21 | |
| YqhD-G39I/S40R-F | 5-GTATTGATTACCTACGGCGGC <u>ATCCGT</u> GTG AAA AAA ACC GGC GTT CTC-3 | 22 | Mutant Y3 (G39I/S40R) |
| YqhD-G39I/S40R-R | 5-GAG AAC GCC GGT TTT TTT CAC <u>ACG GAT</u> GCC GCC GTA GGT AAT CAA TAC-3 | 23 | |
| YqhD-G39Y/S40H-F | 5-GTATTGATTACCTACGGCGGC <u>TATCAT</u> GTG AAA AAA ACC GGC GTT CTC-3 | 24 | Mutant Y5 (G39Y/S40H) |
| Yqhd-G39Y/S40H-R | 5-GAG AAC GCC GGT TTT TTT CAC <u>ATG ATA</u> GCC GCC GTA GGT AAT CAA TAC-3 | 25 | |
| IlvCA71SR76DS78D-F | 5-CGT AAA GAA *T*CG ATT GCC GAG AAG GAT GCG GAT TGG-3 | 26 | |
| IlvCA71SR76DS78D-R | 5-CCA ATC CGC ATC CTT CTC GGC AAT CGA TTC TTT ACG-3 | 27 | |
| ilvCQ110A-F | 5-CGG ACA AGG CGC ACT CTG ATG TAG-3 | 28 | Mutant A (A71S/R76/ S78D/Q110) |
| ilvCQ110A-R | 5-CTA CAT CAG AGT GCG CCT TGT CCG-3 | 29 | |
| ilvCQ110V-F | 5-CGG ACA AGG TGC ACT CTG ATG TAG-3 | 30 | Mutant V (A71S/R76D/ S78D/Q110) |
| ilvCQ110V-R | 5-CTA CAT CAG AGT GCA CCT TGT CCG-3 | 31 | |
| ILVC-Pyx90-Gib-F1 | 5-GAA AGC TCT CTA GGT CGA CGA GGA ATC ACC ATG GCT AAC TAC TTC AAT ACA CTG AAT CTG-3 | 32 | Replace IlvC with mutant A or V |
| ILVC-Pyx90-Gib-R1 | 5-GTA CTT AGG CAT GGT ATA TCT CCT TCC GGG TTA ACC CGC AAC AGC AAT ACG TTT CAT ATC-3 | 33 | |
| ILVD-AvTA-pYX90-Gib-F2 | 5-GAT ATG AAA CGT ATT GCT GTT GCG GGT TAA CCC GGA AGG AGA TAT ACC ATG CCT AAG TAC-3 | 34 | |
| ILVD-AvTA-pYX90-Gib-R2 | 5-GGA TTT GTC CTA CTC AGG AGA GCG TTC ACC GAC AAA CAA CAG ATA AAA CGA AAG GCC CAG-3 | 35 | |

TABLE 1-continued

Primers and mutants for YqhD and IlvC

| Name | Sequence | SEQ ID NO: | Notes |
|---|---|---|---|
| Spec-alsS-pYX90-Gib-F3 | 5-CTG GGC CTT TCG TTT TAT CTG TTG TTT GTC GGT GAA CGC TCT CCT GAG TAG GAC AAA TCC-3 | 36 | |
| Spec-alsS-pYX90-Gib-R3 | 5-CAG ATT CAG TGT ATT GAA GTA GTT AGC CAT GGT GAT TCC TCG TCG ACC TAG AGA GCT TTC-3 | 37 | |
| YqhD-Pyx97-Gib-F1 | 5-GGA GAA AGG TCA CAT GAA CAA CTT TAA TCT GCA CAC CCC AAC CCG CAT TC-3 | 38 | Replace YqhD with mutant |
| YqhD-Pyx97-Gib-R1 | 5-CTC TAG CAC GCG TAC CAT GGG ATC CTT AGC GGG CGG CTT CGT ATA TAC-3 | 39 | Y1, Y2, Y3, or Y5 |
| ColE-Amp-pYX97-Gib-F2 | 5-GTA TAT ACG AAG CCG CCC GCT AAG GAT CCC ATG GTA CGC GTG CTA GAG-3 | 40 | |
| ColE-Amp-pYX97-Gib-R2 | 5-CAT GAT AAT AAT GGT TTC TTA GAC GTC AGG TGG CAC TTT TCG GGG AAA TGT GCG CGG AAC-3 | 41 | |
| LeuDH-KivD-pYX97-F3 | 5-GTT CCG CGC ACA TTT CCC CGA AAA GTG CCA CCT GAC GTC TAA GAA ACC ATT ATT ATC ATG-3 | 42 | |
| LeuDH-KivD-pYX97-R3 | 5-GAA TGC GGG TTG GGG TGT GCA GAT TAA AGT TGT TCA TGT GAC CTT TCT CC-3 | 43 | |

Single colonies of YqhD mutant and wild-type were cultured into 96-well plates. Each well contained 200 µl of LB medium with corresponding antibiotics. Cultures were incubated at 300 rpm and at 37° C. overnight (16 hours) and induced by 1.0 mM isopropyl β-d-1-thiogalactopyranoside (IPTG) for another 24 hours at 250 rpm, 30° C. in a humidified shaker. Cells were harvested by centrifugation (3000 rpm, 4° C., 15 min.) and stored at −20° C. before conducting assays. For high-throughput screening assays, E. coli cells were lysed with 200 µl of 50 mM MOPS (pH 7.0) containing 1 mg/ml of lysozyme (Sigma-Aldrich Corp., St. Louis, Mo.) and 20 U/ml of DNase (NEB) at 4° C. for 6 hours under gentle shaking. Lysed cells were spun down, and 100 µl of the cell free extract was transferred into another 96 well plate. YqhD and its mutant activity assay buffer contained 50 µl of 0.25 mM NADH, 10 µl of isobutyraldehyde, and 40 µl of MOPS (pH 7.0). Consumption of NADH was monitored at 340 nm in a plate reader (Molecular Devices, LLC, Sunnyvale, Calif.).

Plasmids and strain construction for anaerobic bioconversion of algal protein hydrolysates: Positive hits with high activity with NADH were selected to replace the wild-type YqhD gene in plasmid pYX97. Two mutant genes of IlvC were selected to replace the wild-type IlvC gene in plasmid pYX90. A Gibson assembly was applied to replace wild-type YqhD and IlvC with the corresponding mutant genes. Plasmids pYX97 and pYX90 with mutant genes, as well as pYX68 were co-transformed into strain YH40 for the bioconversion of algal protein hydrolysates into fusel butanol. All the primers used herein are listed in Table 1, above.

Addition of NADPH into fermentation media: Wild-type strain YH83 was cultured in 20 ml of LB media with 100 µg/ml ampicillin, 34 µg/ml chloramphenicol, and 25 µg/ml spectinomycin overnight. Then, 5 ml of culture was transferred into 150 ml of 1× M9 medium (see, e.g., Huo Y X et al., *Nat. Biotechnol.* 2011; 29(4):346-51; and Wu W, "Fuel ethanol production using novel carbon sources and fermentation medium optimization with response surface methodology," *Int. J. Agri. Biol. Eng.* 2013; 6(2):42-53) (in 160 ml serum bottle) containing 20 g/L of an amino acid mixture, 2 g/L of LB, and 150 µM NADPH with corresponding aforementioned antibiotics in a rotary shaker at 220 rpm, 37° C. The culture was induced by 1 mM IPTG at 37° C. when the OD reached 0.6 for the production of fusel butanol. Samples were tested at regular time intervals to determine the concentration of fusel butanol in each sample. Each run was performed in biological duplicate.

Investigation of the fusel butanol yields with an amino acid mixture: Engineered strains of YH83 containing various combinations of mutant YqhD and IlvC were cultured in 20 ml of LB media with corresponding aforementioned antibiotics, overnight. Then, 3 ml of culture was transferred into 30 ml of 1× M9 medium containing 20 g/L of an amino acid mixture (Sigma-Aldrich, Corp.), 5 g/L of LB, and antibiotics. Fermentation was performed as described above. Each run was performed in biological duplicate. Strains containing the details of the mutants are listed in Table 1, above.

Bioconversion of algal protein hydrolysates into fusel butanol: ATP algae biomass samples were pretreated with diluted acid, according to the protocol from the National Renewable Energy Laboratories (referenced hereinafter as "ATP3") or according to the protocol described previously (see, e.g., Garcia-Moscoso J L et al., "Kinetics of peptides and arginine production from microalgae (*Scenedesmus* sp.) by flash hydrolysis," *Ind. Eng. Chem. Res.* 2015; 54(7): 2048-58) through a thermal flash hydrolysis (referenced hereinafter as "ODU"). Hydrolyzed algal carbohydrate was converted into ethanol through alcoholic fermentation using an ethanogenic strain, E. coli KO11. The cell mass was removed through centrifugation (6,000 rpm, 4° C., 10 min.) at the end of KO11 fermentation. The supernatant containing ethanol and algal protein was air-bubbled at room temperature for 10 minutes to remove ethanol. Then, the resultant supernatant was concentrated and digested with 2 mg/mL Pronase® (Promega Corp., Madison, Wis.) following the manufacturer's protocol. The protease-digested, algal protein hydrolysate was sterilized through a 0.45 µm PTFE membrane and used as the fermentation media for fusel butanol production. This hydrolysate was incubated with mutant strain AY3 in the presence of the amino acid mixture. Samples were tested at regular intervals with GC-MS analysis. Each run was performed in biological duplicate.

Analytic determination of the presence of fusel butanol and amino acid: Concentrations of amino acids were analyzed using an amino acid analyzer (Hitachi Ltd., Tokyo, Japan) at the genome center of University of California, Davis, following their protocol. Fusel butanol was extracted using ethyl acetate at a ratio of 1:1 (ethyl acetate: fermentation broth), with 2-methyl-pentanol as an internal reference. The mixture was vortex at 1,200 rpm for 20 min. and centrifuged at 14,000 rpm, 5 min. The ethyl acetate layer was collected for further GC-MS analysis. Two μl of sample was inserted into the injection port (220° C.) of an Agilent 7890A Gas Chromatograph containing a 30 m×0.25 mm i.d. DB wax capillary column with a film thickness of 0.25 μm. The column was temperature programmed as follows: 40° C. for 4 min., increasing to 65° C. at 10° C./min. and holding for 10 min., then increasing to 120° C. at 10° C./min. and holding for 2 min., and then increasing to 220° C. at 20° C./min and holding for 5 min. The carrier gas was ultra-high purity helium at a constant flow rate of 1.8 ml/min. The initial column head pressure was 16.188 psi with a split ratio of 10. The gas chromatograph was coupled to a quadrupole mass selective detector (MSD), Agilent 5975C. The MSD parameters included EI at 70 eV, mass range at 10-650 Da, and scan speed at 2 scans/sec. Spectral components were searched against the NIST 2015 mass spectral library. Serial of dilutions of isobutanol and 2-methyl-butanol in ethyl acetate were analyzed to determine a standard curve. Concentrations of fusel butanol were calculated by referring samples to the standard curve.

Example 3: Cofactor Engineering of Ketol-Acid Reductoisomerase (IlvC) and Alcohol Dehydrogenase (YqhD)

Increasing concerns about diminishing fossil fuels and global environmental problems have attracted interest in sustainable biofuels obtained from renewable resources (see, e.g., Peralta-Yahya P P et al., "Microbial engineering for the production of advanced biofuels," *Nature* 2012; 488(7411): 320-8; and Keasling D, "Sustainable production of advanced biofuels," 241*st ACS National Meeting & Exposition*, held on 27-31 Mar. 2011 in Anaheim, Calif., Abstract 202). Algae-based biofuel is considered to be one sustainable alternative biofuel due to several benefits, including simplified pretreatment as compared to lignocellulosic biomass, higher biomass yields as compared to plants, possible cultivation on nonarable land, and possible reclamation of waste water (see, e.g., Razeghifard R, "Algal biofuels," *Photosynth. Res.* 2013; 117(1-3):207-19; and Luque R, "Algal biofuels: the eternal promise?," *Energy Environ. Sci.* 2010; 3:254-7). So far, algae biomass have been converted to versatile biofuel chemicals, such as bioethanol, biohydrogen, biogas, crude oil, and biodiesel (see, e.g., Li K et al., "An overview of algae bioethanol production," *Int. J. Energy Res.* 2014; 38(8):965-77; Melis A et al., "Hydrogen production: green algae as a source of energy," *Plant Physiol.* 2001; 127(3):740-8; Hernández D et al., "Biofuels from microalgae: lipid extraction and methane production from the residual biomass in a biorefinery approach," *Bioresour. Technol.* 2014; 170:370-8; Lopez Barreiro D et al., "Assessing microalgae biorefinery routes for the production of biofuels via hydrothermal liquefaction," *Bioresour. Technol.* 2014; 174:256-65; Sharma K K et al., "High lipid induction in microalgae for biodiesel production," *Energies* 2012; 5(5):1532-53; and Scott S A et al., "Biodiesel from algae: challenges and prospects," *Curr. Opin. Biotechnol.* 2010; 21(3):277-86).

Current state-of-the-art algal biofuels have primarily focused on producing biodiesel by boosting algal lipid yield under nutrient stress conditions. This strategy ignores another major component of algae: proteins. Under conditions that support robust algae growth, algal carbohydrate and proteins are two of the major components of biomass, including up to ~80% of the ash-free dry weight (AFDW) of microalgae biomass, in which up to 60% can be proteins (see, e.g., Luque R, *Energy Environ. Sci.* 2010; 3:254-7; Becker E W, "Microalgae: biotechnology and microbiology," Cambridge University Press, Cambridge, U.K., 1994 (293 pp.); and Singh J et al., "Commercialization potential of microalgae for biofuels production," *Renew. Sustain. Energy Rev.* 2010; 14(9):2596-610).

Recently, engineered *E. coli* strains have been employed to convert algal protein into fusel butanol. Modified strains can be selected to exhibit deamination of protein hydrolysates to C4 and C5 alcohols at 56% of the theoretical yield (see, e.g., Huo Y X et al., "Conversion of proteins into biofuels by engineering nitrogen flux," *Nat. Biotechnol.* 2011; 29(4):346-51). By combining the Ehrlich pathway with three exogenous transamination and deamination cycles, the engineered *E. coli* strain produced up to 0.183 g of fusel butanol/g of amino acids under aerobic or microaerobic fermentation conditions (see, e.g., Huo Y X et al., *Nat. Biotechnol.* 2011; 29(4):346-51). In some instances, anaerobic conditions can be preferred for large scale fermentation due to lower operating costs and higher theoretical yield.

In the Ehrlich pathway for isobutanol production, two enzymes use nicotinamide adenine dinucleotide phosphate (NADPH) as a cofactor: ketol-acid reductoisomerase (IlvC) and alcohol dehydrogenase (YqhD). Thus, bioconversion of protein hydrolysates requires at least two reducing equivalents of NADPH to convert glucose to isobutanol (see, e.g., Atsumi S et al., "Non-fermentative pathways for synthesis of branched-chain higher alcohols as biofuels," *Nature* 2008; 451(7174):86-9). Under anaerobic fermentation, glycolysis can only produce nicotinamide adenine dinucleotide (NADH) as an available reducing equivalent, while the pentose phosphate pathway (PPP) and the tricarboxylic acid (TCA) cycle are not functional due to the lack of oxygen. This may result in a cofactor imbalance during anaerobic fermentation or oxygen limited fermentation conditions (e.g., microaerobic conditions). Thus, although anaerobic or microaerobic fermentation is preferred to minimize processing costs and to increase theoretical yields, these very fermentation conditions can result in an inhibitory cofactor imbalance that can limit alcohol production.

NADPH limitation can result in cofactor imbalance, as reported previously for isobutanol production from glucose (see, e.g., Shi A et al., "Activating transhydrogenase and NAD kinase in combination for improving isobutanol production," *Metab. Eng.* 2013; 16:1-10; and Bastian S et al., "Engineered ketol-acid reductoisomerase and alcohol dehydrogenase enable anaerobic 2-methylpropan-1-ol production at theoretical yield in *Escherichia coli*," *Metab. Eng.* 2011; 13(3):345-52). Therefore, we hypothesized that fusel butanol yield can be improved through resolving the cofactor imbalance present in anaerobic fermentation of algal protein.

To achieve this, we first tested our hypothesis that lack of NADPH affects fusel alcohol production. Thus, we performed experiments by adding NADPH in the fermentation media and observing the effect of NADPH on alcohol yield. Then, we designed two isobutanol biosynthesis pathway enzymes (IlvC and YqhD) to switch cofactor specificity from NADPH to NADH through directed evolution. Upon combining the beneficial mutations of two enzymes in the isobutanol biosynthesis pathway, the resultant engineered *E. coli* strain improved fusel butanol yield by about 60%, as compared to wild-type, under anaerobic fermentation conditions with an amino acid mixture as the feedstock. When applied to algal protein hydrolysates, the mutant strain with best performance produced 38% to 100% more fusel butanol, as compared to wild-type.

Figure 10A:
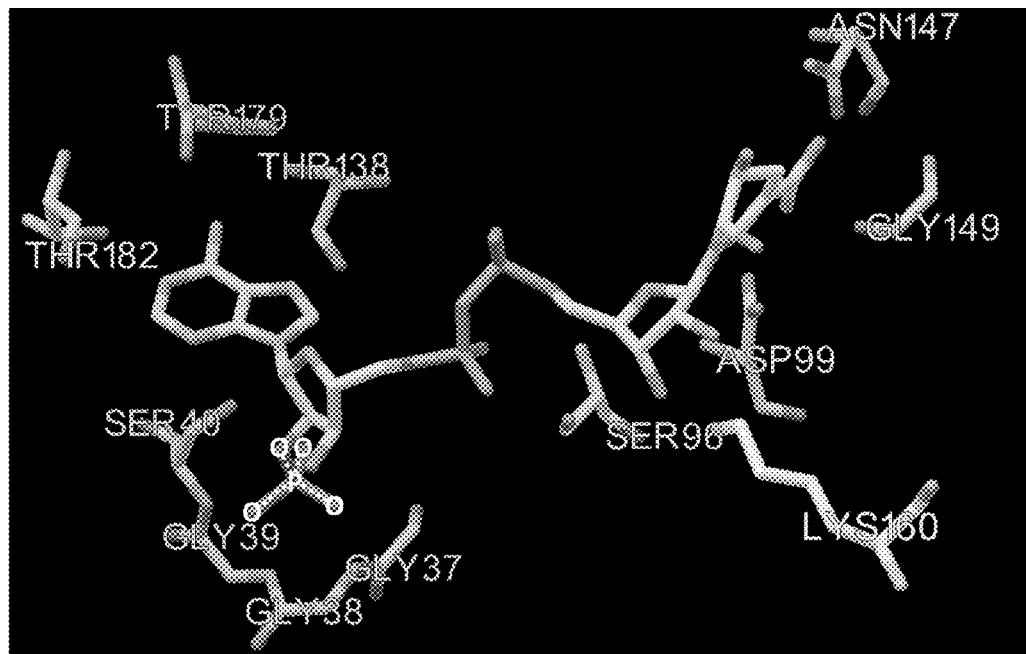

Engineering the cofactor specificity of E. coli IlvC and YqhD to switch to NADH: The x-ray crystal structure of YqhD had been reported previously (see, e.g., Sulzenbacher G et al., "Crystal structure of E. coli alcohol dehydrogenase YqhD: evidence of a covalently modified NADP coenzyme," J. Mol. Biol. 2004; 342(2):489-502). This structure contained cofactor $NADP^+$ as a ligand. The protein possesses a GGGS (residues 37-40) motif, which binds the 2'-phosphate groups of NADP through hydrogen bonds, as shown in FIG. 10A (phosphorous and oxygen atoms of the 2'-phosphate is indicated by P, O, and dashed lines). These hydrogen bonds provide a preference for binding NADPH over NADH, making the motif GGGS a major cofactor binding site. Therefore, two amino acids (Gly39Ser40) were chosen to identify mutations that would confer cofactor switching from NADPH to NADH through site-saturation mutagenesis.

Figure 10B:
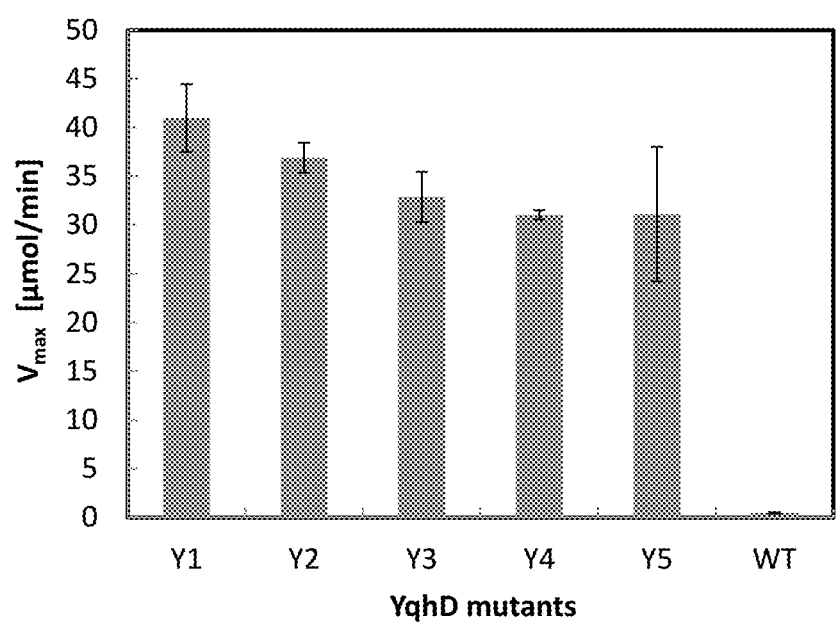

Two mutant libraries (G39S40 and S40) were generated and screened for NADH activity using a cell free extract. More than 20 positive mutants showed various activities with cofactor NADH. Five mutants showed 60-80 times higher activity with NADH (as shown in FIG. 10B), as compared to wild-type YqhD (FIG. 10C). The five mutants were selected to replace wild-type YqhD in plasmid pYX97, including two single mutations of S40 (Y1, Y2) (see, e.g., FIGS. 10D-10E) and three double mutations of G39S40 (Y3, Y4, Y5) (see, e.g., FIG. 10F).

E. coli IlvC has been engineered to switch cofactor from NADPH to NADH for isobutanol production under anaerobic fermentation (see, e.g., Bastian S et al., Metab. Eng. 2011; 13(3):345-52). Two mutants of IlvC (A71S, R76D, S78D, Q110V/A) with higher activity with NADH were chosen to replace wild-type IlvC in plasmid pYX90 (see, FIGS. 11A-11B).

Figure 12A:
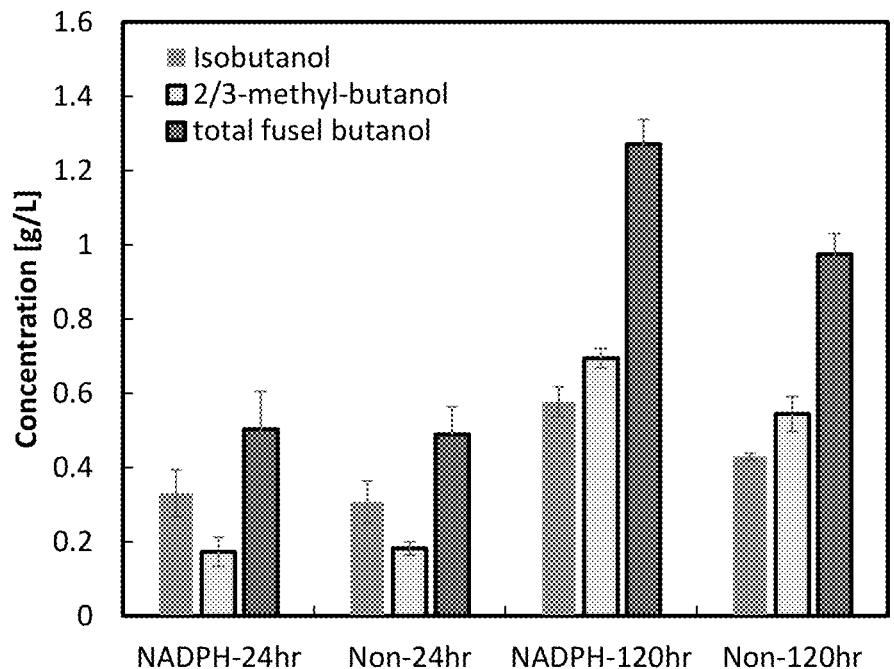
FIGS. 12A-12B shows the effect of adding native cofactor NADPH on yield of butanol for protein bioconversion. Provided are (A) a graph showing the effects of NADPH addition on the produced concentration fusel butanol under anaerobic fermentation conditions and (B) a graph showing the improvement of fusel butanol yield after 24 hours and 120 hours.
Figure 12B:
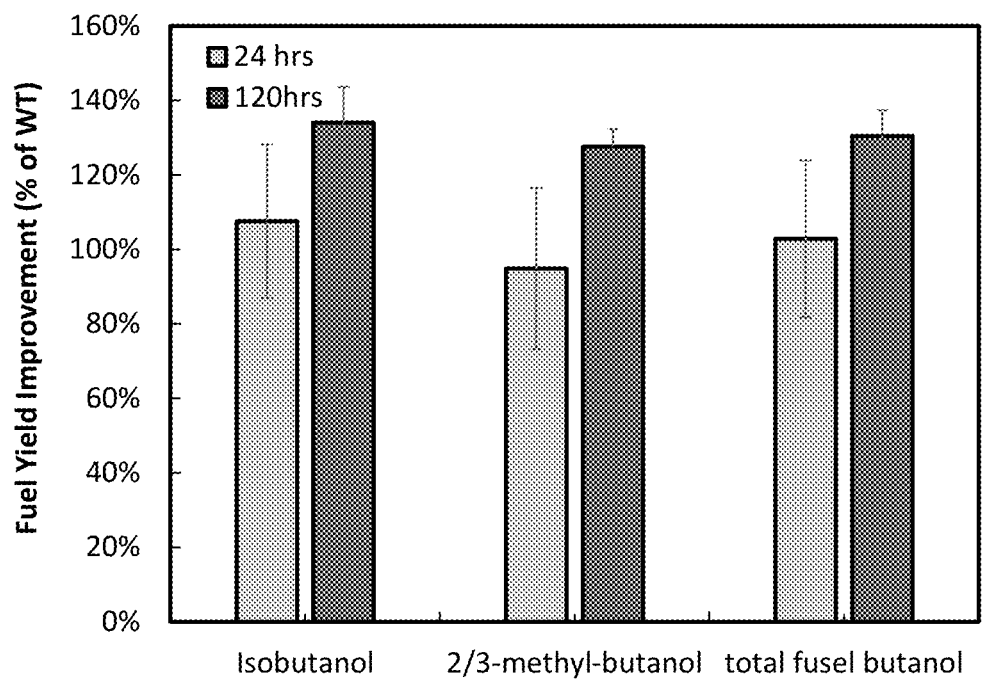

Improved fusel butanol yield under anaerobic fermentation with NADPH: We hypothesized that cofactor imbalance compromised fusel butanol yield during protein bioconversion. To test this hypothesis, the native cofactor NADPH of YqhD and IlvC was added into the fermentation medium as an external source of NADPH. FIGS. 12A-12B show that addition of NADPH significantly improved yields of isobutanol and ⅔-methyl-butanol during protein bioconversion. Within 5 days of cultivation, yields of isobutanol, ⅔-methyl-butanol, and total fusel butanol increased by about 34%, 28%, and 30%, respectively, confirming that cofactor imbalance can be one factor affecting fusel butanol production.

Figure 13A:
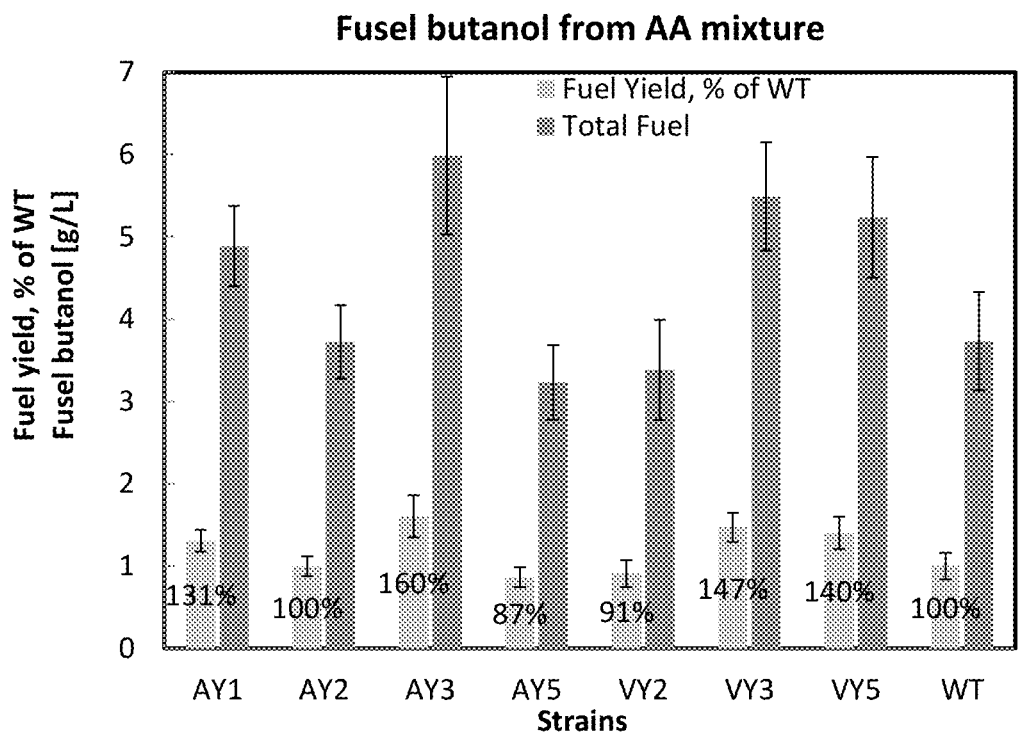
FIGS. 13A-13C shows bioconversion of algal protein hydrolysates into fusel butanol by engineered mutant strains. Provided are (A) a graph showing fermentation performance of engineered mutant strains on an amino acid mixture; (B) a graph showing bioconversion of two algal protein hydrolysates (ATP3 or ODU) into fusel butanol employing either an engineered mutant strain AY3 or a wild-type strain YH83 ("WT"); and (C) a graph showing consumption of two algal protein hydrolysates (ATP3 or ODU) by engineered mutant strain AY3 after 72 hours.

Bioconversion of amino acid mixtures and algal protein into fusel butanol: The fusel butanol yields of the engineered YH83 strains, which contained both IlvC and YqhD mutants, were initially investigated through bioconversion of amino acid mixtures in the 1× M9 medium. As seen in FIG. 13A, the mutant strains produced various amounts of fusel butanol in the fermentation broth. Among the seven mutant strains, four strains (AY1, AY3, VY3, and VY5) yielded at least 30% higher concentrations of fusel butanol, as compared to wild-type. In particular, the AY3 strain produced more than 60% higher amount of fusel butanol than wild-type, i.e., up to 6 g/L fusel butanol from 20 g/L amino acids. The wild-type produced 3.7 g/L fusel butanol.

Further studies were conducted with pretreated algal protein hydrolysates. Two hydrolysates were used as medium to investigate fermentation performance of mutant strain AY3. As shown in the FIG. 13B, mutant strain AY3 produced higher titers of isobutanol, ⅔-methyl-butanol, and total fusel butanol with both pretreated algal protein hydrolysates (ATP3 and ODU), as compared to wild-type strain YH83.

Figure 13B:
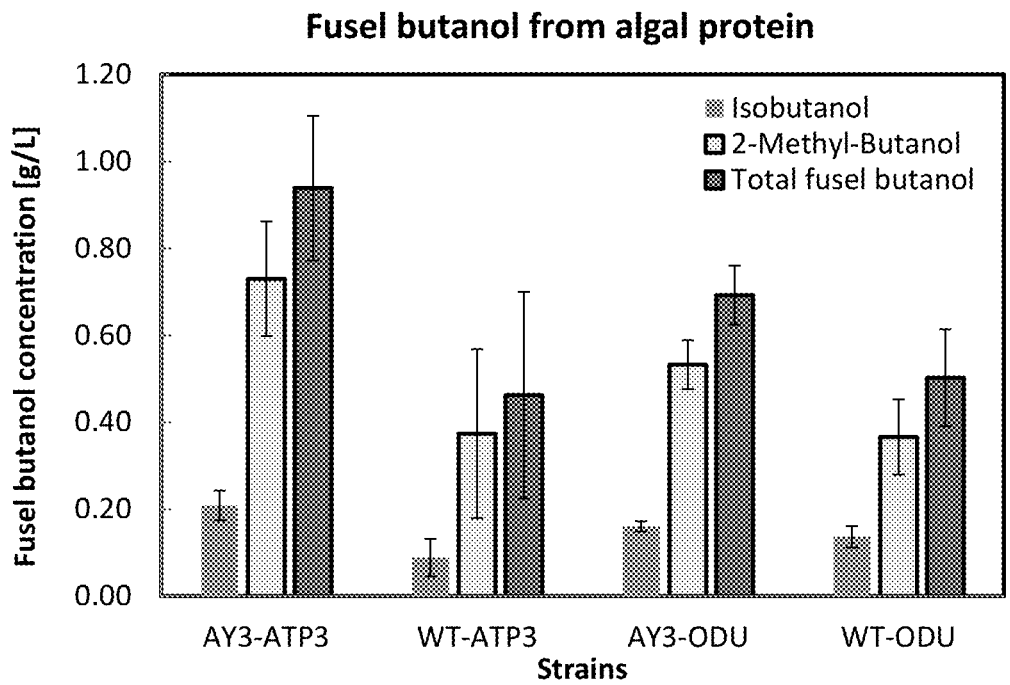

Within 3 days of fermentation, the mutant strain AY3 yielded more than 100% and 38% higher total fusel butanol titers than wild-type with ATP3 and ODU, respectively, as shown in FIG. 13B. Yields using algal hydrolysates were lower than that observed with amino acid mixtures. Yields can be optimized, e.g., by providing supplemental nutrients with the algal hydrolysates, adjusting the ionic strength of the hydrolysate, neutralizing the hydrolysate, etc.

Figure 13C:
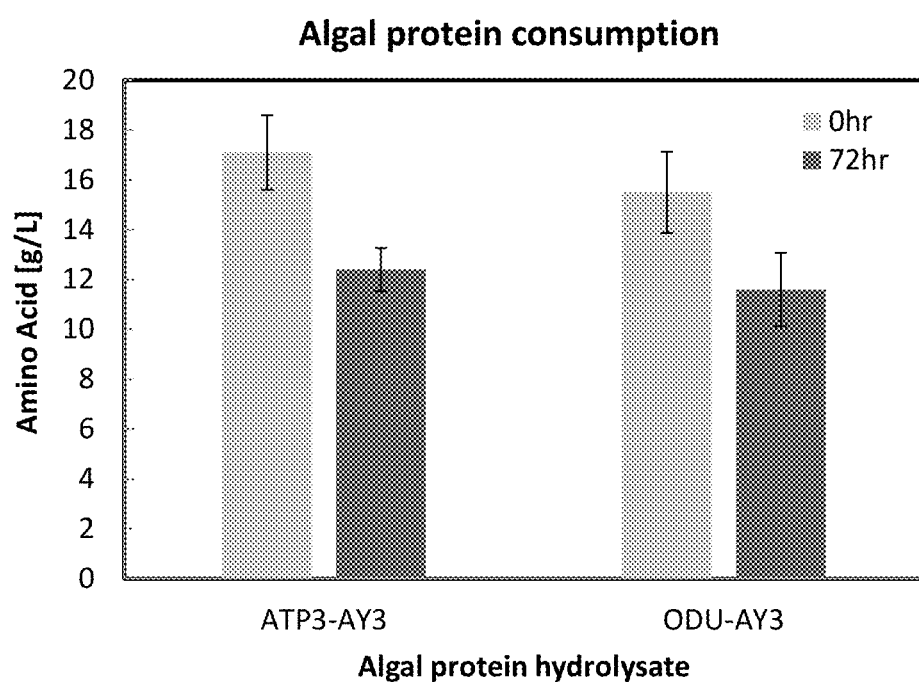

As shown in FIG. 13C, only about 25% of algal protein hydrolysates were consumed after 3 days of fermentation. Based on substrate consumption, the strain AY3 yielded 0.2 to 0.18 g fusel butanol/g amino acid for converting algal hydrolysates AY3 and ODU, respectively. Yields could be optimized in any useful manner, e.g., by increasing incubation times, increasing protease digestion times, repeating and recycling separated fractions, etc.

Here, we engineered two enzymes (IlvC and YqhD) in the isobutanol biosynthesis pathway to resolve cofactor imbalance during fermentation. By combining beneficial mutations of these two enzymes, the engineered AY3 strain improved fusel butanol yield with an algal hydrolysate, as compared to the wild-type strain. Fusel butanol possess the higher energy density, lower vapor pressure, lower hygroscopicity than fuel ethanol and has been considered as an advanced fuel compounds (see, e.g., Lan E I et al., "Microbial synthesis of n-butanol, isobutanol, and other higher alcohols from diverse resources," Bioresour. Technol. 2013; 135:339-49; and Smith K M et al., "An evolutionary strategy for isobutanol production strain development in Escherichia coli," Metab. Eng. 2011; 13(6):674-81). Recently, algal protein hydrolysates were reported into fusel butanol but at a relative low titer (see, e.g., Huo Y X et al., Nat. Biotechnol. 2011; 29(4):346-51). One of possible factors that results in the lower fusel titer could be the co-factor imbalance during the fermentation, in which strategies to address these factors are described herein.

Other Embodiments

All publications, patents, and patent applications mentioned in this specification are incorporated herein by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are within the claims.

The invention claimed is:

1. An isolated nucleic acid comprising the nucleotide sequence of any one of SEQ ID NOs: 14-25;
    wherein the isolated nucleic acid encodes a polypeptide sequence having at least 90% sequence identity to the amino acid sequence of any one of SEQ ID NOs: 2-5;
    wherein in SEQ ID NO: 4, the Xaa at position 39 is Ile, Tyr, Val, Leu, Phe, or any other conservative amino acid substitution; and the Xaa at position 40 is Pro, Arg, His, Lys, Trp or any other conservative amino acid substitution; and
    wherein the isolated nucleic acid encodes a modified alcohol dehydrogenase having increased reactivity with nicotinamide adenine dinucleotide (NADH), as compared to a wild-type alcohol dehydrogenase.

2. A vector comprising the nucleic acid sequence of claim 1.

3. A vector comprising:
    a first nucleic acid sequence encoding a modified alcohol dehydrogenase, wherein the first nucleic acid comprises the nucleotide sequence of any one of SEQ ID NOs: 14-25; and
    a second nucleic acid sequence encoding a modified ketol-acid reductoisomerase wherein the second nucleic acid has at least 90% sequence identity to the nucleotide sequence of any one of SEQ ID NOs: 26-31.

4. The vector of claim 3, wherein the second nucleic acid has at least 95% sequence identity to the nucleotide sequence of any one of SEQ ID NOs: 26-31.

5. The vector of claim 3, wherein the second nucleic acid comprises the nucleotide sequence of any one of SEQ ID NOs: 26-31.

6. The isolated nucleic acid of claim 1, wherein the isolated nucleic acid encodes a polypeptide sequence comprising the amino acid sequence of any one of SEQ ID NOs: 2-5.

7. The isolated nucleic acid of claim 1, wherein the isolated nucleic acid encodes a polypeptide sequence that has at least 90% sequence identity to the amino acid sequence of SEQ ID NO: 2.

8. The isolated nucleic acid of claim 1, wherein the isolated nucleic acid encodes a polypeptide sequence that has at least 90% sequence identity to the amino acid sequence of SEQ ID NO: 3.

9. The isolated nucleic acid of claim 1, wherein the isolated nucleic acid encodes a polypeptide that has at least 90% sequence identity to the amino acid sequence of SEQ ID NO: 5.

10. The isolated nucleic acid of claim 1, wherein the isolated nucleic acid encodes a polypeptide sequence that has at least 90% sequence identity to the amino acid sequence of SEQ ID NO: 4, wherein in SEQ ID NO: 4 the Xaa at position 39 is Ile, Tyr, Val, Leu, or Phe; and the Xaa at position 40 is Pro, Arg, His, Lys, or Trp.

* * * * *